United States Patent
Berkland et al.

(10) Patent No.: US 9,402,861 B2
(45) Date of Patent: Aug. 2, 2016

(54) POLYAMINE-DIHYDROXYBENZOIC ACID CONJUGATE HYDROGELS AS IRON CHELATORS

(75) Inventors: Cory Berkland, Douglas, KS (US); Zahra Mohammadi, Travis, TX (US)

(73) Assignee: THE UNIVERSITY OF KANSAS, Lawrence, KS (US)

( * ) Notice: Subject to any disclaimer, the term of this patent is extended or adjusted under 35 U.S.C. 154(b) by 768 days.

(21) Appl. No.: 13/603,125

(22) Filed: Sep. 4, 2012

(65) Prior Publication Data

US 2013/0056211 A1 Mar. 7, 2013

Related U.S. Application Data

(63) Continuation-in-part of application No. PCT/US2011/026872, filed on Mar. 2, 2011.

(60) Provisional application No. 61/309,790, filed on Mar. 2, 2010.

(51) Int. Cl.
C08F 8/00 (2006.01)
A61K 31/785 (2006.01)
C08F 26/02 (2006.01)

(52) U.S. Cl.
CPC .............. *A61K 31/785* (2013.01); *C08F 8/00* (2013.01); *C08F 26/02* (2013.01); *C08F 2810/20* (2013.01)

(58) Field of Classification Search
None
See application file for complete search history.

(56) References Cited

U.S. PATENT DOCUMENTS

| | | | |
|---|---|---|---|
| 3,758,540 A | 9/1973 | Martell | |
| 4,442,305 A | 4/1984 | Weitl | |
| 5,300,628 A | 4/1994 | Honda | |
| 5,385,997 A | 1/1995 | Buchan | |
| 5,487,888 A | 1/1996 | Mandeville | |
| 5,534,611 A | 7/1996 | Huddleston | |
| 5,616,497 A | 4/1997 | Strickland | |
| 5,643,456 A * | 7/1997 | Smith et al. | 210/651 |
| 5,702,696 A | 12/1997 | Mandeville | |
| 5,777,129 A | 7/1998 | Juneau | |
| 5,834,525 A | 11/1998 | Fish | |
| 7,342,083 B2 | 3/2008 | Chang | |
| 2005/0008570 A1 | 1/2005 | Raymond | |
| 2005/0288398 A1 * | 12/2005 | Messersmith et al. | 524/17 |
| 2006/0065604 A1 | 3/2006 | McKenna | |
| 2007/0274945 A1 | 11/2007 | Scott | |
| 2009/0036611 A1 * | 2/2009 | Wilker et al. | 525/328.5 |
| 2009/0123652 A1 * | 5/2009 | Messersmith | B05D 7/52 427/352 |
| 2009/0252780 A1 | 10/2009 | Pacetti | |

FOREIGN PATENT DOCUMENTS

| | | |
|---|---|---|
| EP | 0401833 | 12/1990 |
| WO | 2005023310 | 3/2005 |
| WO | 2007127225 | 11/2007 |

* cited by examiner

*Primary Examiner* — Robert C Boyle
(74) *Attorney, Agent, or Firm* — Matthew S. Gibson; Reed Smith LLP

(57) ABSTRACT

Compositions and methods for making a composition comprising a polymer and one or more chelators covalently coupled to polymer, wherein the one or more chelators has a benzene ring with more than one hydroxyl group at any position that is free, or a derivative of the chelator, or a salt of the chelator and methods of use.

11 Claims, 60 Drawing Sheets

FIGURE 3
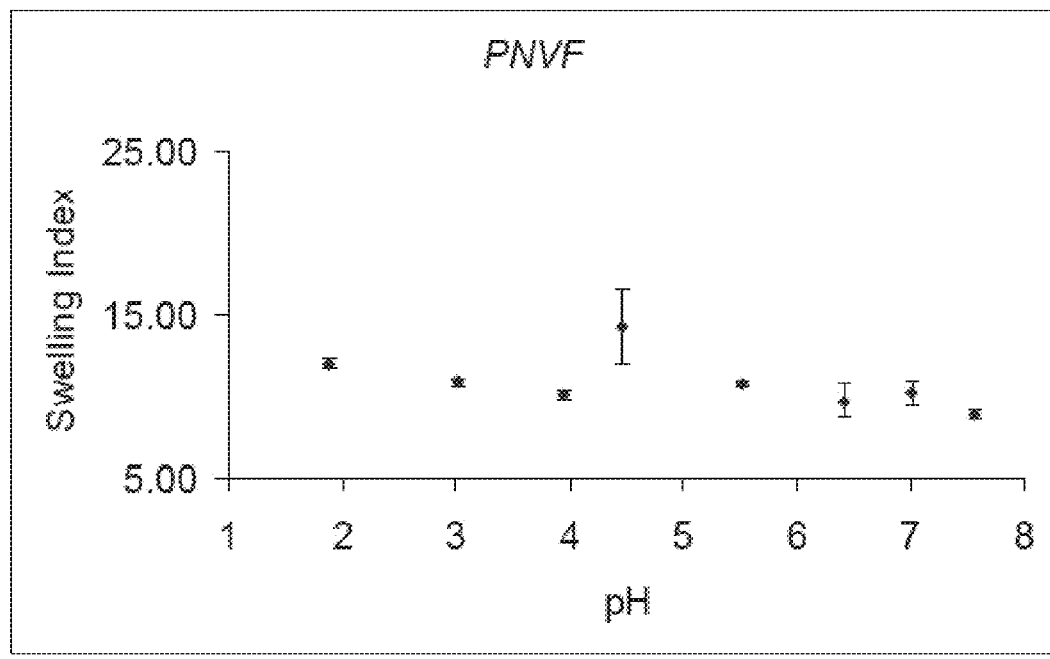
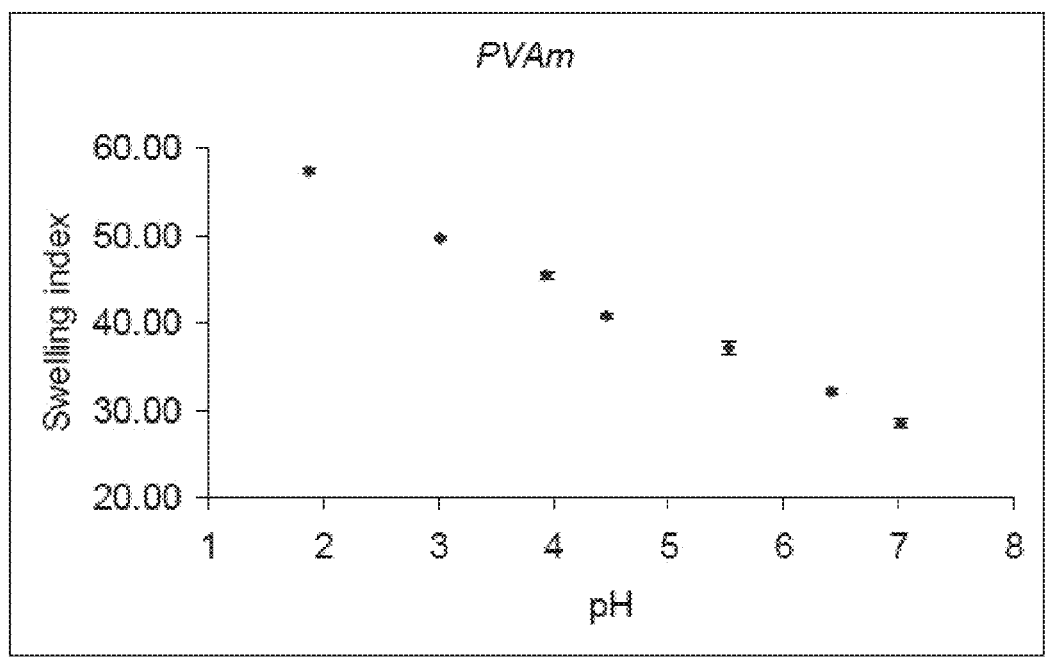

FIGURE 4
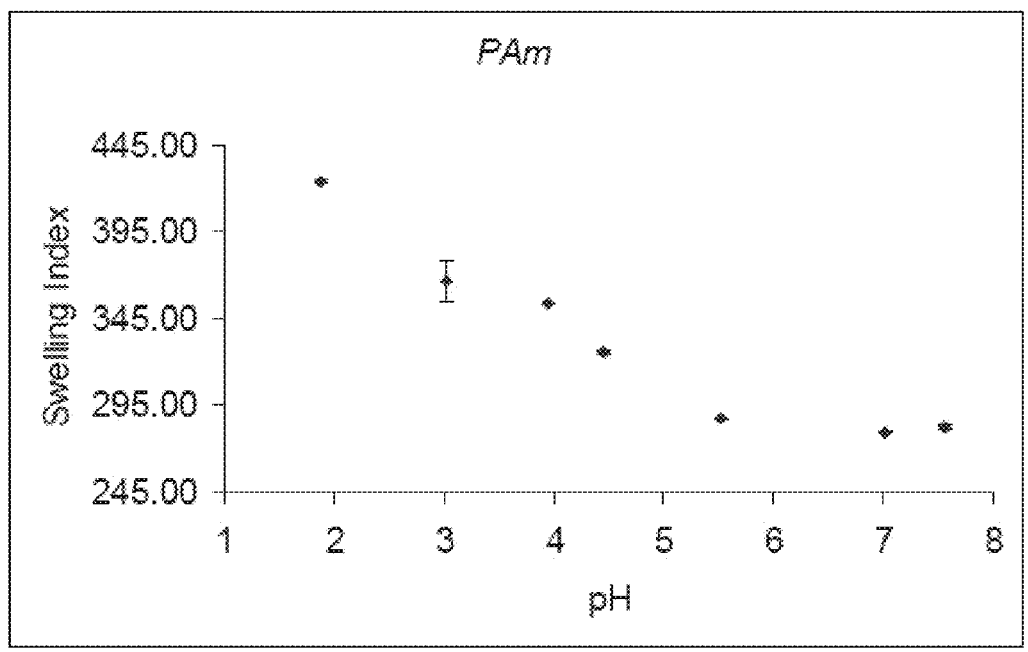
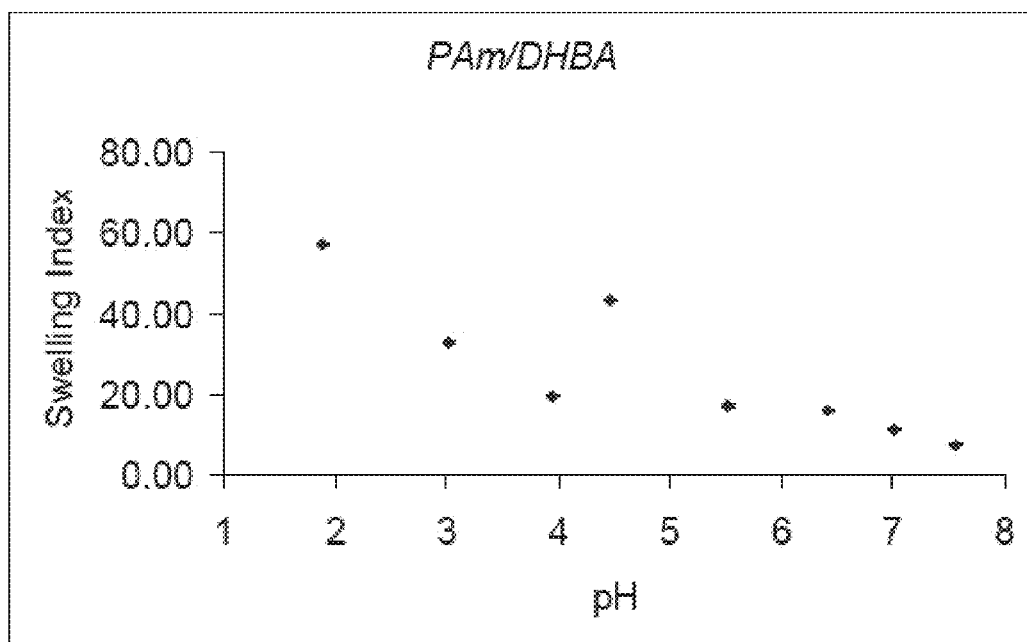

FIGURE 5
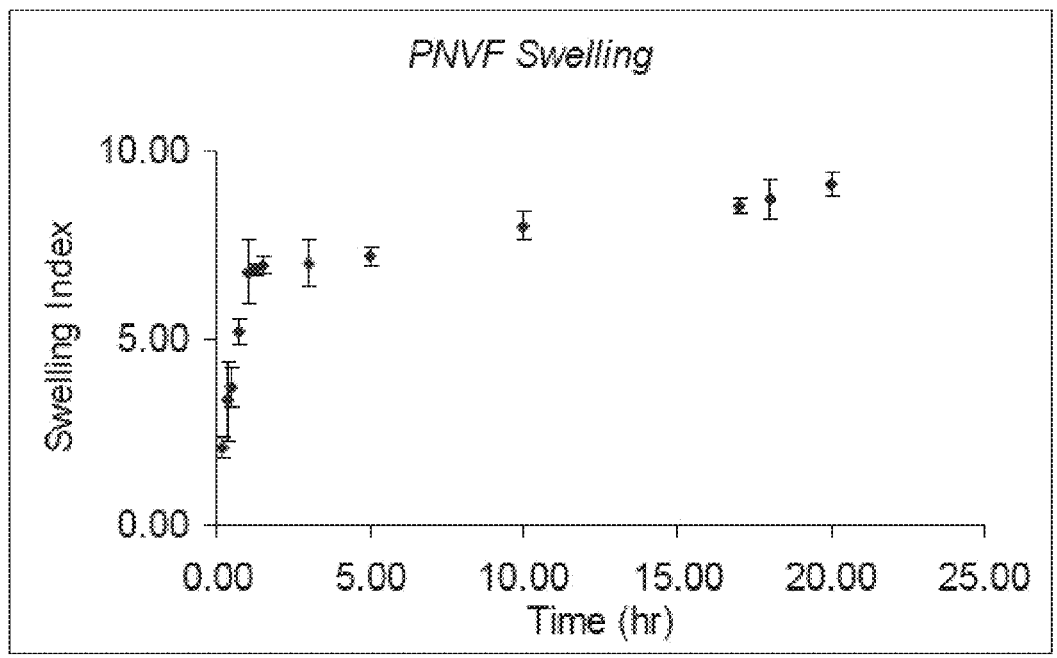
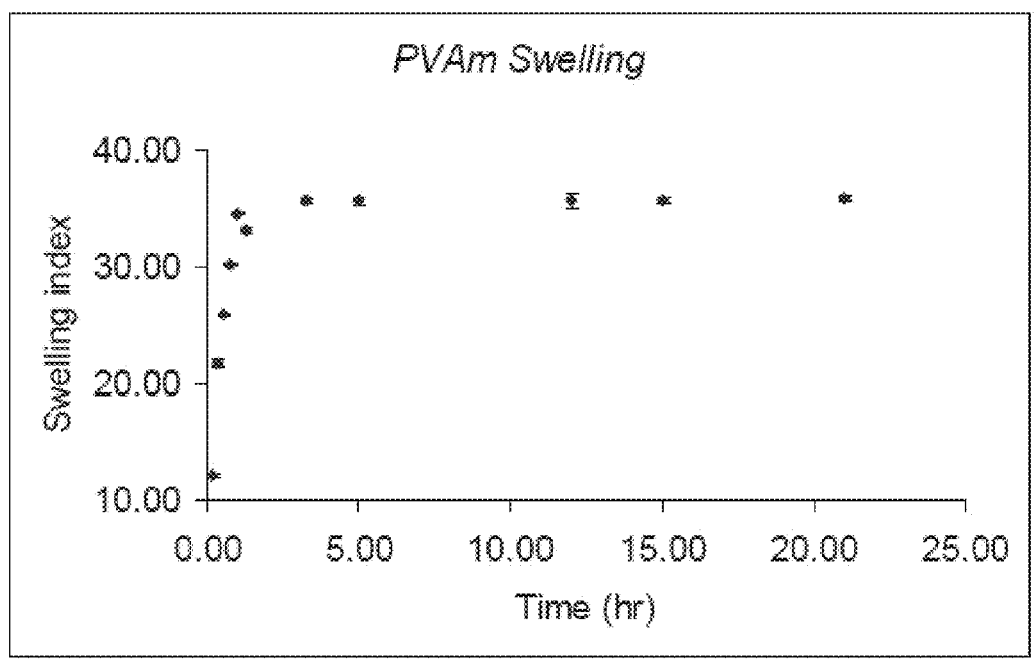

FIGURE 6
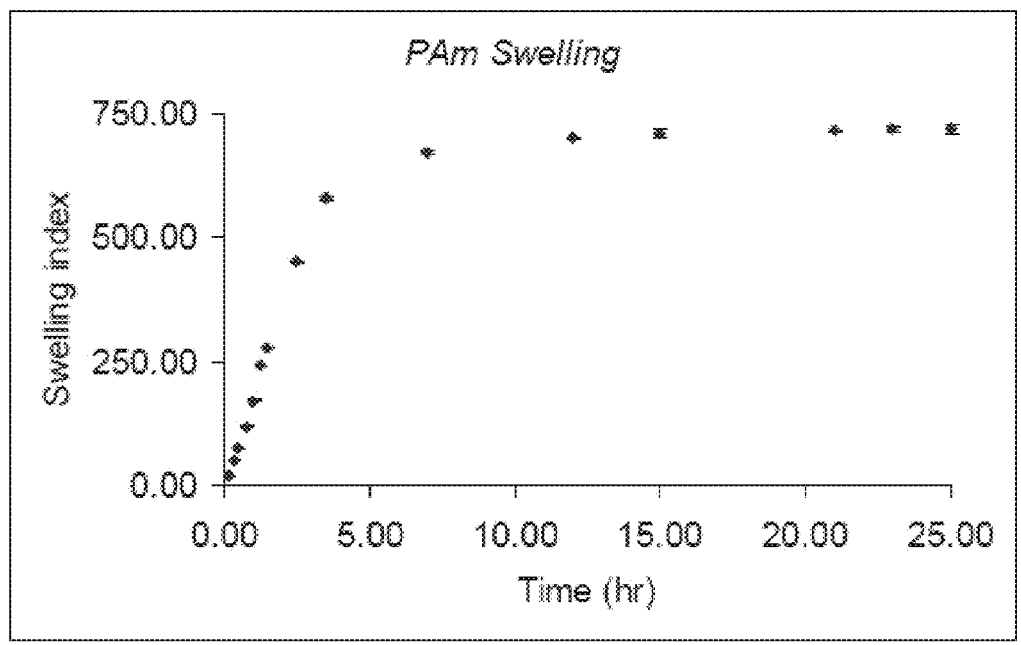
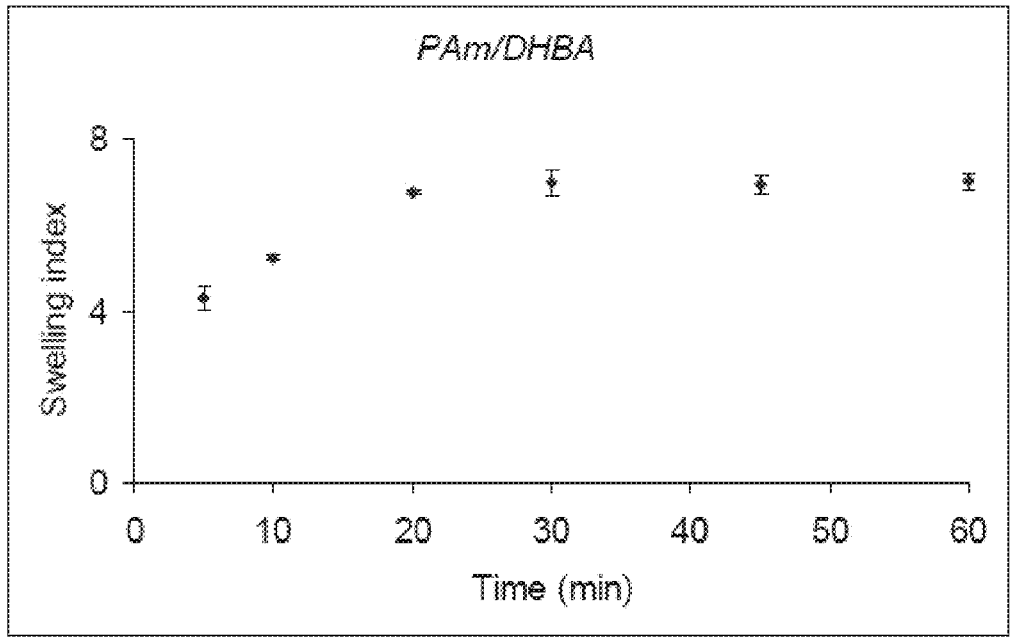

FIGURE 7
*PVAm*
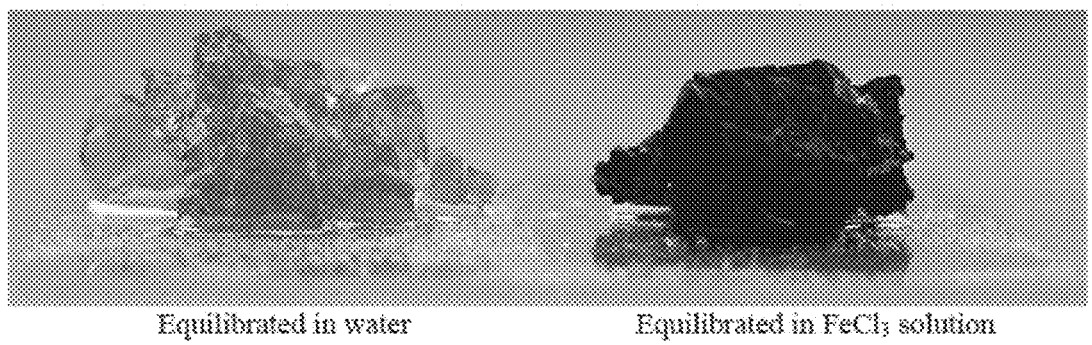
Equilibrated in water        Equilibrated in FeCl₃ solution
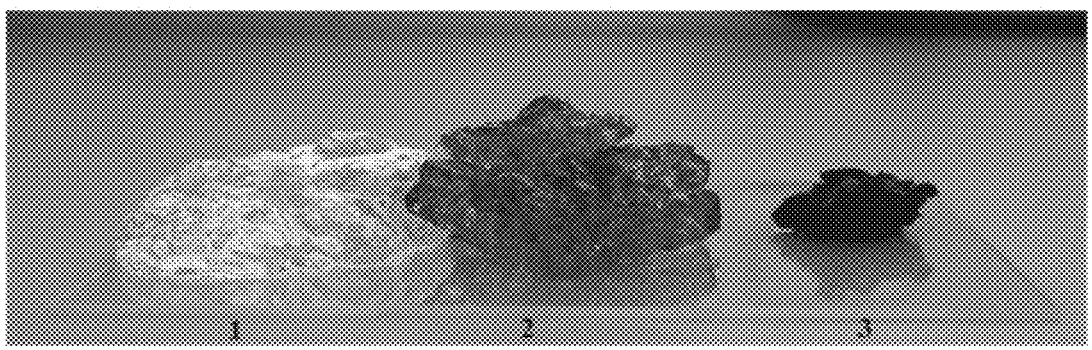
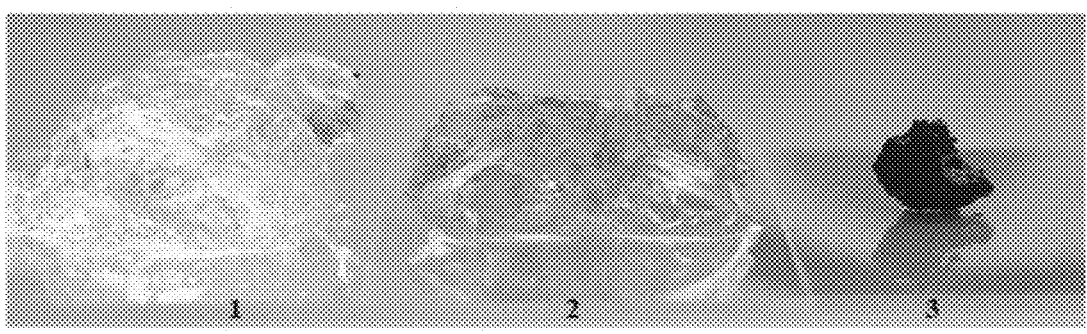

Swelling Index at pH=7.29

FIGURE 21

*Fe III at pH 2-3*

| PAAm/DHBA (Langmuir), $r^2=0.9916$ | | PAAm (Langmuir), $r^2=0.8858$ | |
|---|---|---|---|
| 555.56 | Max Absorbed dry gel (mg/Kg) | 1000.00 | Max Absorbed dry gel (mg/Kg) |
| 60000.00 | K | 3333.33 | K |
| 4.78 | Log K | 3.52 | Log K |

| PAAm/DHBA (Freundlich), $r^2=0.9982$ | | PAAm (Freundlich), $r^2=0.8812$ | |
|---|---|---|---|
| 3.08 | n | 1.53 | n |
| 775.53 | K | 1116.09 | K |
| 2.89 | Log K | 3.05 | Log K |

*Fe III at pH 5-6*

| PAAm/DHBA (Langmuir), $r^2=0.9824$ | | PAAm (Langmuir), $r^2=0.9735$ | |
|---|---|---|---|
| 0.12 | Max Absorbed dry gel (mg/Kg) | 0.10 | Max Absorbed dry gel (mg/Kg) |
| 0.56 | K | 0.81 | K |
| 0.25 | Log K | 0.09 | Log K |

| PAAm/DHBA (Freundlich), $r^2=0.9902$ | | PAAm (Freundlich), $r^2=0.9705$ | |
|---|---|---|---|
| 1.51 | n | 1.64 | n |
| 3454.02 | K | 2243.58 | K |
| 3.54 | Log K | 3.05 | Log K |

| PAAm/DHBA (Langmuir), r²=0.9294 | | PAAm (Langmuir), r²=0.8866 | |
|---|---|---|---|
| 2500.00 | Max Absorbed/dry gel (mg/Kg) | 909.09 | Max Absorbed/dry gel (mg/Kg) |
| 2000.00 | K | 13751.38 | K |
| 3.30 | Log K | 4.14 | Log K |

| PAAm/DHBA (Freundlich), r²=0.8912 | | PAAm (Freundlich), r²=0.8345 | |
|---|---|---|---|
| 1.58 | n | 3.11 | n |
| 2229.46 | K | 1084.43 | K |
| 3.35 | Log K | 3.05 | Log K |

*Fe II at pH 2-3*

| PAAm/DHBA (Langmuir), r²=.9583 | | PAAm (Langmuir), r²=0.8492 | |
|---|---|---|---|
| 2000.00 | Max Absorbed/dry gel (mg/Kg) | 3333.33 | Max Absorbed/dry gel (mg/Kg) |
| 10000.00 | K | 750.01 | K |
| 4.00 | Log K | 2.88 | Log K |

| PAAm/DHBA (Freundlich), r²=0.9927 | | PAAm (Freundlich), r²=0.8162 | |
|---|---|---|---|
| 4.77 | n | 0.96 | n |
| 3133.29 | K | 3593.35 | K |
| 3.50 | Log K | 3.05 | Log K |

| PAAm/DHBA (Langmuir), $r^2$=0.9841 | | PAAm (Langmuir), $r^2$=0.9817 | |
|---|---|---|---|
| 1250.00 | Max Absorbed/dry gel (mg/Kg) | 1250.00 | Max Absorbed/dry gel (mg/Kg) |
| 88888.89 | K | 40000.00 | K |
| 4.95 | Log K | 4.60 | Log K |

| PAAm/DHBA (Freundlich), $r^2$=0.9895 | | PAAm (Freundlich), $r^2$=0.952 | |
|---|---|---|---|
| 2.15 | n | 1.97 | n |
| 4384.30 | K | 3608.90 | K |
| 3.64 | Log K | 3.05 | Log K |

FIGURE 34
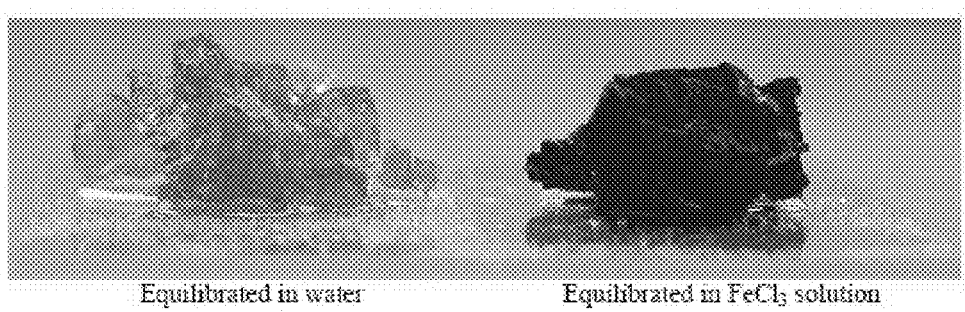
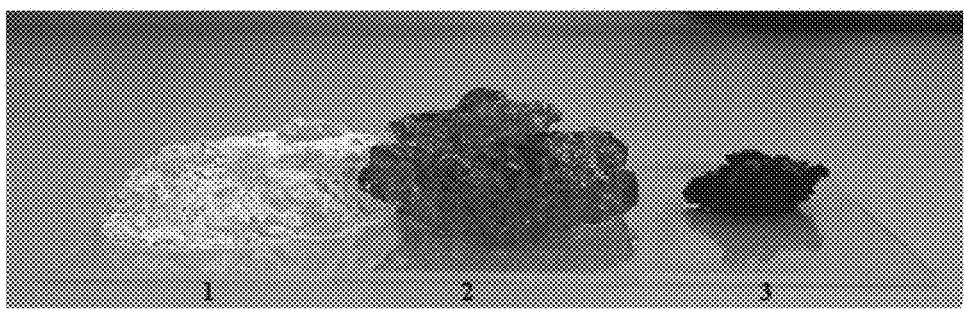
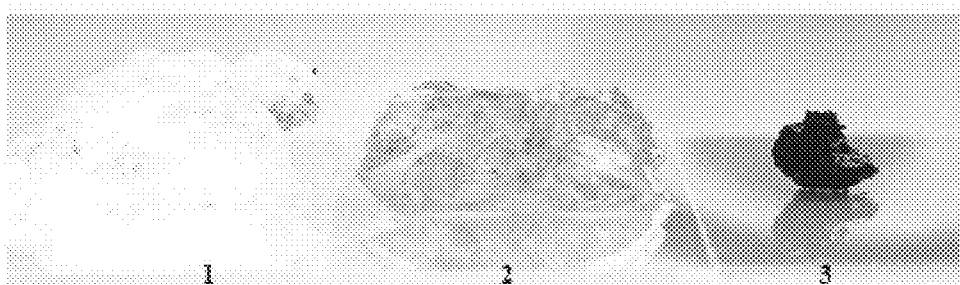

FIGURE 40 A AND B

FIGURE 41 A AND B

FIGURE 42 A, B, C AND D

FIGURE 46
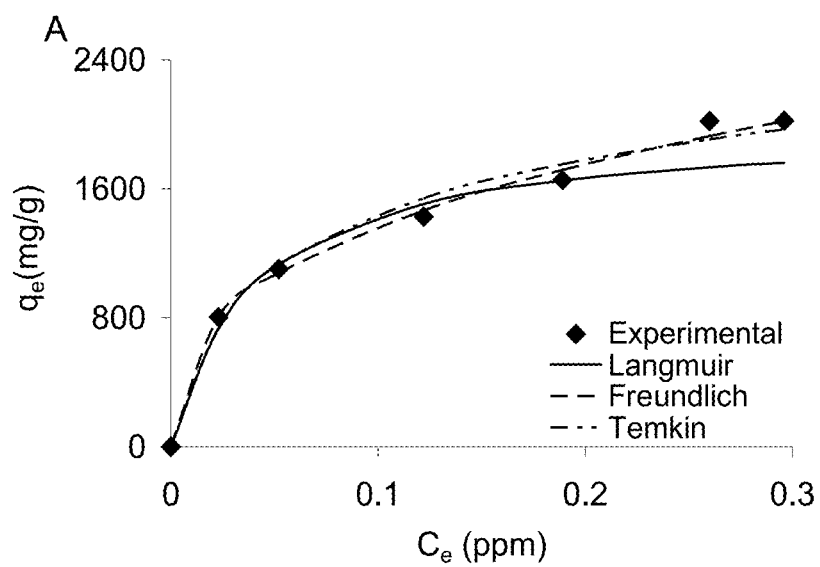
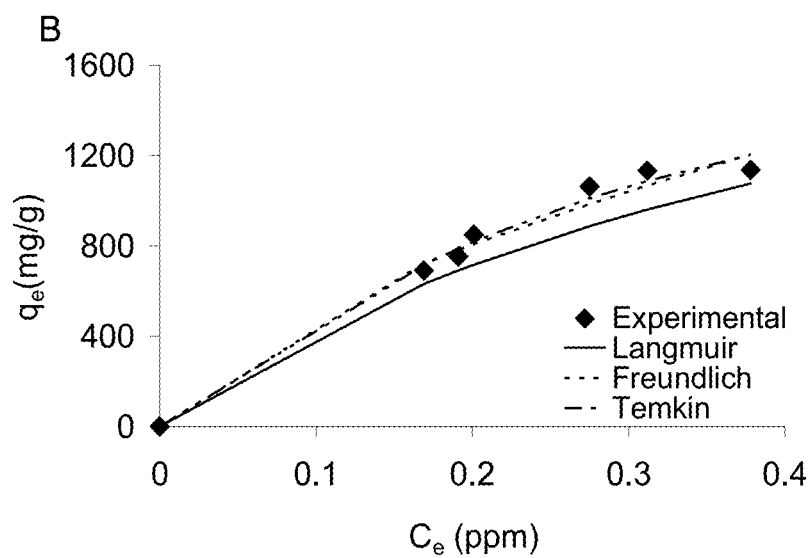

FIGURE 47 (CONT.)
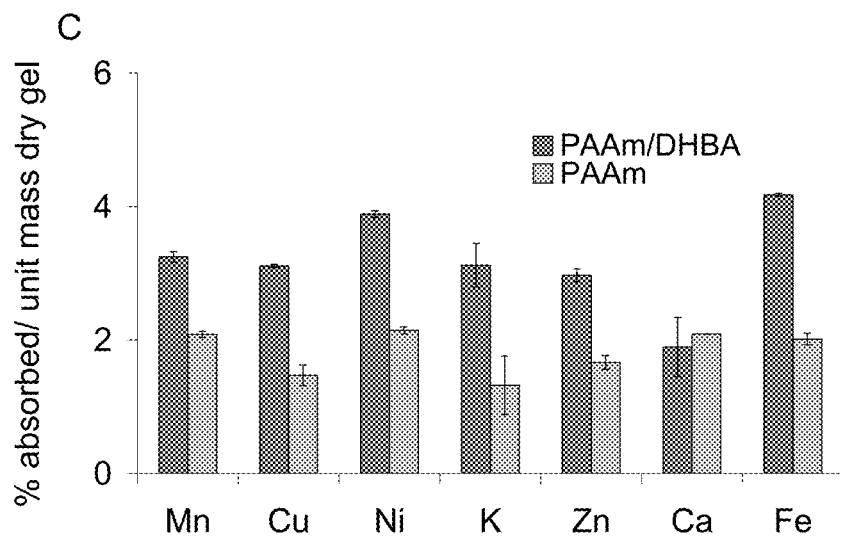
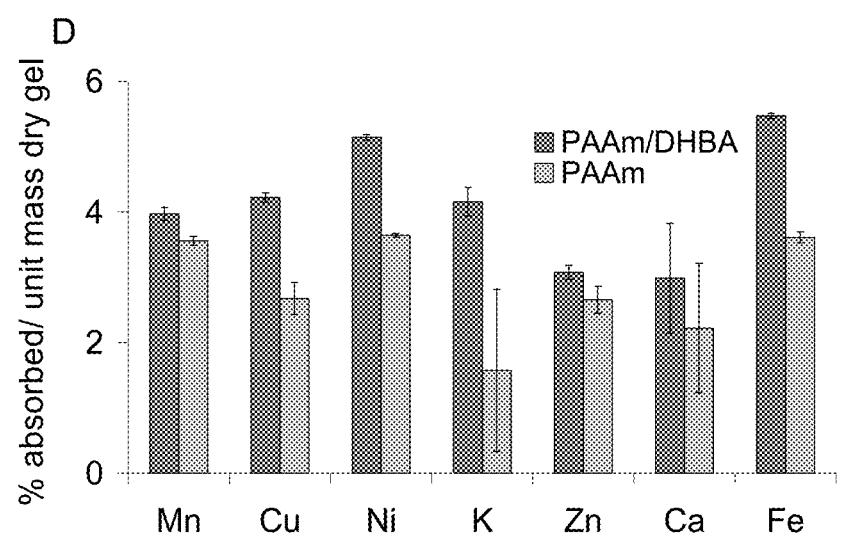

FIGURE 50
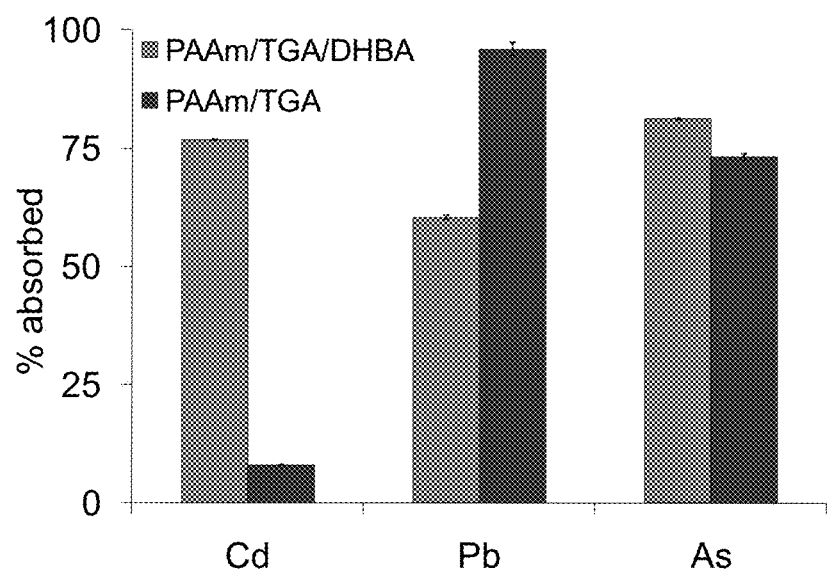
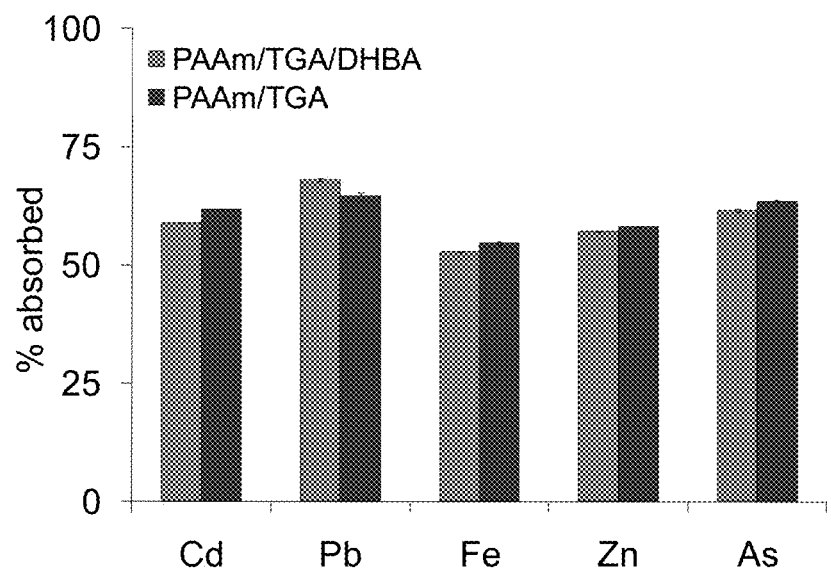

FIGURE 59
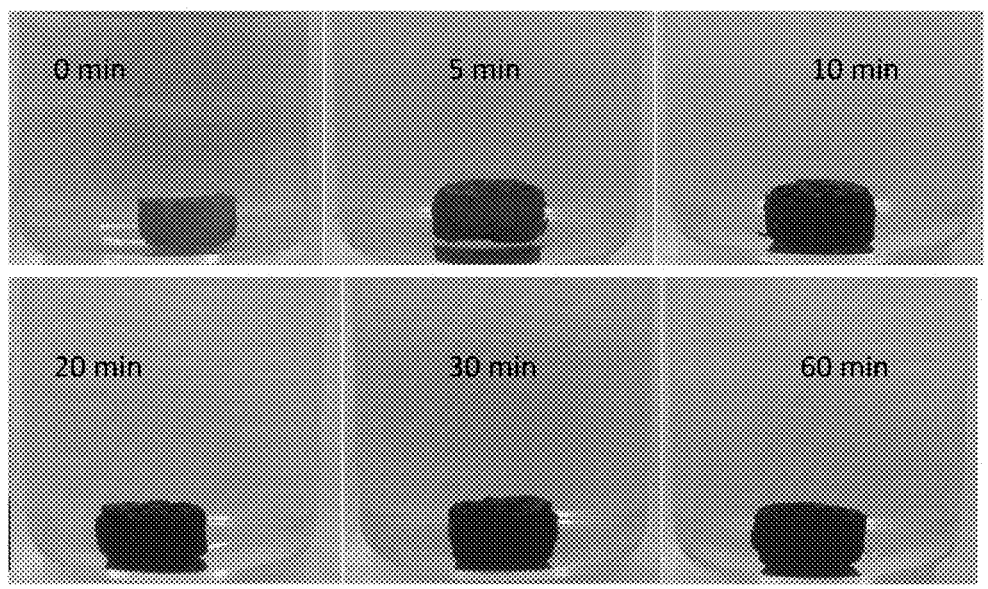
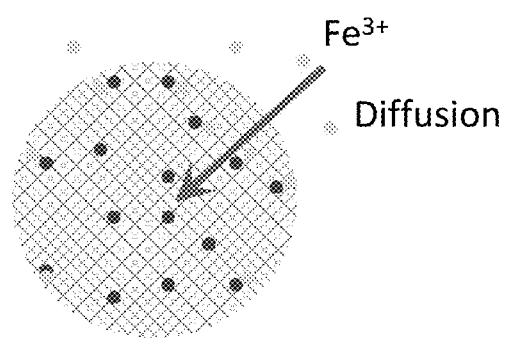
$Fe^{3+}$
Diffusion

POLYAMINE-DIHYDROXYBENZOIC ACID CONJUGATE HYDROGELS AS IRON CHELATORS

CROSS-REFERENCE TO RELATED APPLICATIONS

This application is a continuation-in-part of International Patent Application No. PCT/US2011/26872, filed Mar. 2, 2011, which claims the benefit of U.S. Provisional Patent Application Ser. No. 61/309,790, filed on Mar. 2, 2010, the entire disclosures of which is hereby incorporated by reference.

BACKGROUND

Metals such as cadmium, lead, and arsenic are highly toxic to living organisms. Wastewater discharge may be a primary source of heavy metal release into the environment. The removal of heavy metal ions from industrial wastewater has been given much attention in the last decade, because such components can accumulate in living organisms. Upon their accumulation in the human body, these toxic metals may cause kidney failure, nerve system damage, and bone damage, as well as other serious diseases. The necessity to reduce the amount of heavy metal ions from the environment has led to an increasing interest in technologies that selectively remove such toxic metals.

There are 35 metals that are of concern because of occupational or residential exposure; 23 of these are the heavy elements or "heavy metals." Heavy metals are chemical elements with a specific gravity that is at least 5 times the specific gravity of water. Small amounts of these elements are common in our environment and diet and in some cases are actually necessary for good health, but large amounts of any of them may cause acute or chronic toxicity. Heavy metal toxicity can result in damaged or reduced mental and central nervous function, lower energy levels, and damage to blood composition, lungs, kidneys, liver, and other vital organs. Long-term exposure may result in slowly progressing physical, muscular, and neurological degenerative processes that mimic Alzheimer's disease, Parkinson's disease, muscular dystrophy, and multiple sclerosis. Allergies are not uncommon and repeated long-term contact with some metals or their compounds may even cause cancer.

A particular heavy metal of concern is iron. Iron is an essential and ubiquitous element in all forms of life involved in a multitude of biological processes and essential for many critical human biological processes. Yet, the presence of excess iron in the body may lead to toxic effects.

Iron overload is a serious complication in patients that have β-thalassemia and is the focal point of its management. In patients that do not receive transfusions, abnormal iron absorption can produce an increase in the body iron burden, which is evaluated to be in the 2-5 gram per year range. Patients that receive treatments that include regular blood transfusions can lead to double this amount of iron accumulation. Iron accumulation introduces progressive damage in liver, heart, and in the endocrine system if left untreated. The available iron is deposited in parenchymal tissues and in reticuloendothelial cells. When the iron load increases, the iron binding capacity of serum transferrin is exceeded and a non-transferrin-bound fraction of plasma iron (NTBI) appears. The NTBI can generate free hydroxyl radicals and induces dangerous tissue damage. Iron accumulates at different rates in various organs, each of which react in a characteristic way to the damage induced by NTBI and by the intracellular labile iron pool (LIP). Current treatments for iron overload diseases include chelation therapy to chelate the iron and reduce its bioavailability. In one example, chelation therapy can be performed with desferoxamine (DFO), which is administered by subcutaneous infusion. Drugs that can be administered orally include deferiprone and Exjade. DFO therapy has reportedly been associated with several drawbacks including a narrow therapeutic window and lack of oral bioavailability. As a result, it requires administration for 8-12 hours per day by infusion. DFO can not be readily absorbed through the intestine and must be injected intravenously thus, is not an ideal chelator since systemic side effects are likely. Furthermore, concerns have arisen over its use due to numerous significant drug-related toxicities. Serious adverse effects such as neutropenia, agranulocytosis, hypersensitivity reactions, and blood vessel inflammation have also been reported upon the oral application of deferiprone and Exjade.

One possible method of avoiding the use of systemic iron chelators is to inhibit iron absorption from the gastrointestinal tract by orally available, non-absorbed iron chelators that selectively sequester and remove excess dietary iron from the GI tract. Non-absorbed polymer therapies that act by sequestering a number of undesired ionic species in the gastrointestinal tract have been successful clinically. Using non-absorbed polymer therapies is particularly relevant to thalassemia intermedia and hemochromatosis. Iron binding polymers have considerable potential in this therapeutic approach as they can effectively bind iron irreversibly to form nontoxic, inert complexes that are not absorbed by the gastrointestinal tract, thereby reducing the absorption of iron from the intestine.

Microorganisms have developed a sophisticated Fe(III) acquisition and transport systems involving siderophores. Siderophores are low molecular weight chelating agents that bind Fe(III) ion with high specificity. The iron binding affinity of siderophores dramatically exceeds that of iron chelating therapeutics currently available. Enterobactin, a naturally occurring tris-catechol siderophore, is the most powerful Fe(III) chelator known with a relative iron binding constant of 35.5. Since nearly all iron is bound in vivo, next generation iron chelators must achieve significantly higher iron binding and selectivity with low toxicity and side effects. Researchers have synthesized small molecule siderophore mimetics; however, compounds that directly mimic siderophores would be expected to enhance bacterial recruitment of iron. What is needed is a novel iron chelator that binds iron tightly and removes it from the body.

DRAWINGS

Some specific example embodiments of the disclosure may be understood by referring, in part, to the following description and the accompanying drawings.

FIG. 3 is a chart depicting swelling properties of a hydrogel.

FIG. 4 is a chart depicting swelling properties of a polymer.

FIG. 5 is a chart depicting swelling properties of a polymer.

FIG. 6 is a chart depicting swelling properties of a polymer.

FIG. 7 are photographs of hydrogels.

Figure 17:
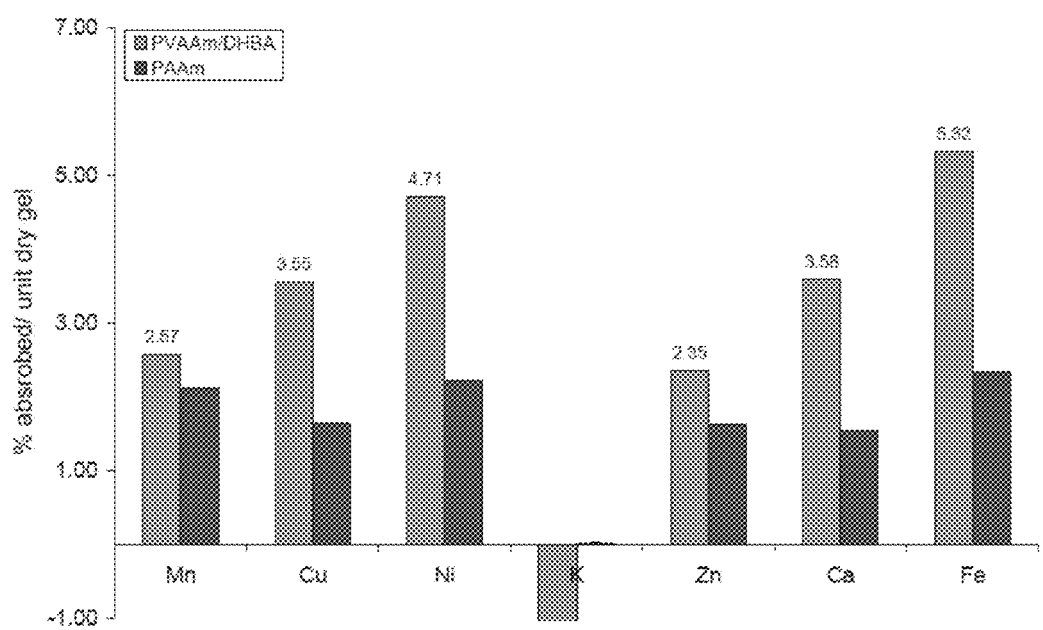
Figure 18:
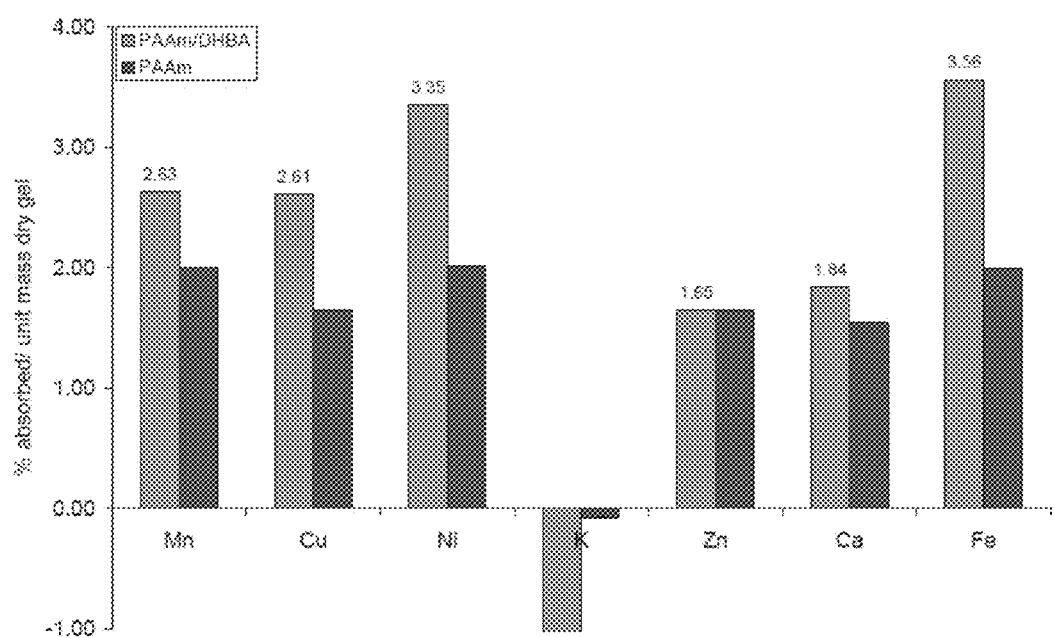
Figure 19:
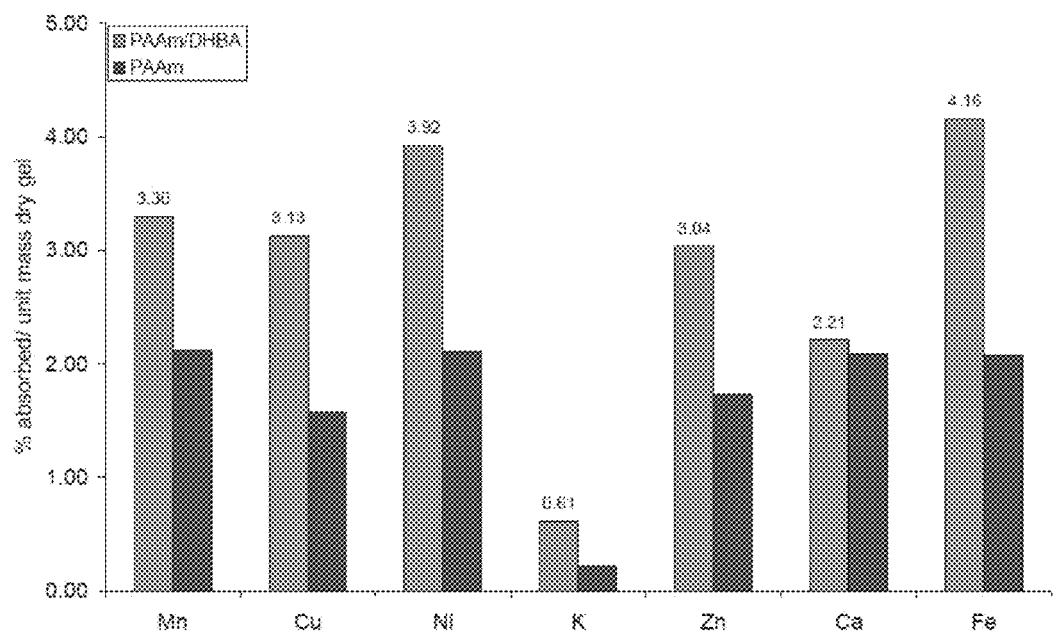
Figure 20:
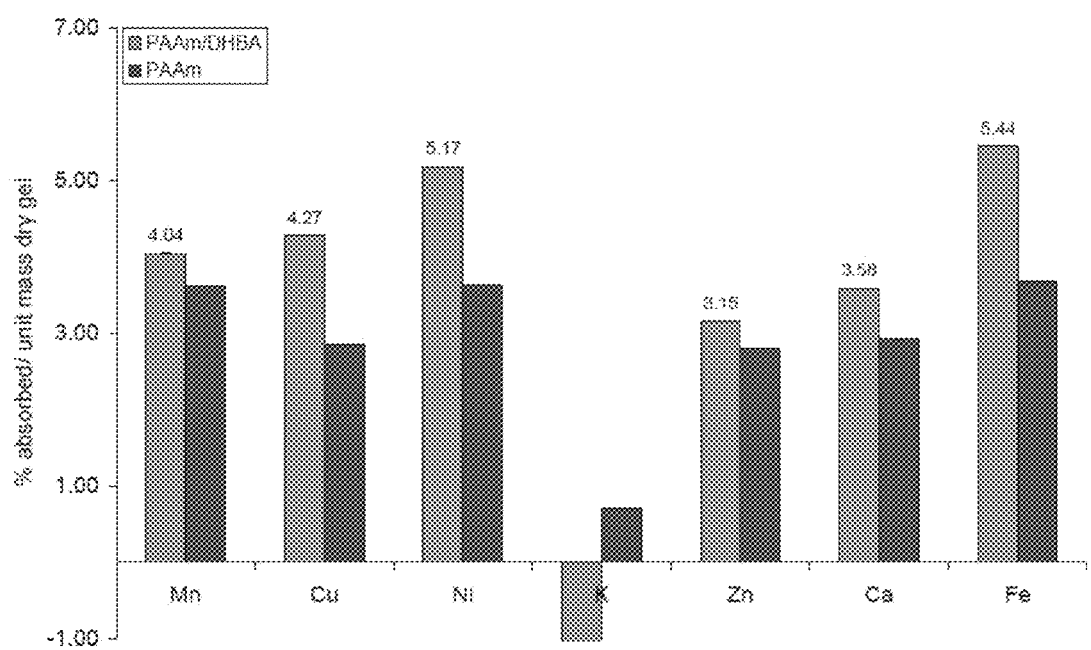
Figure 24:
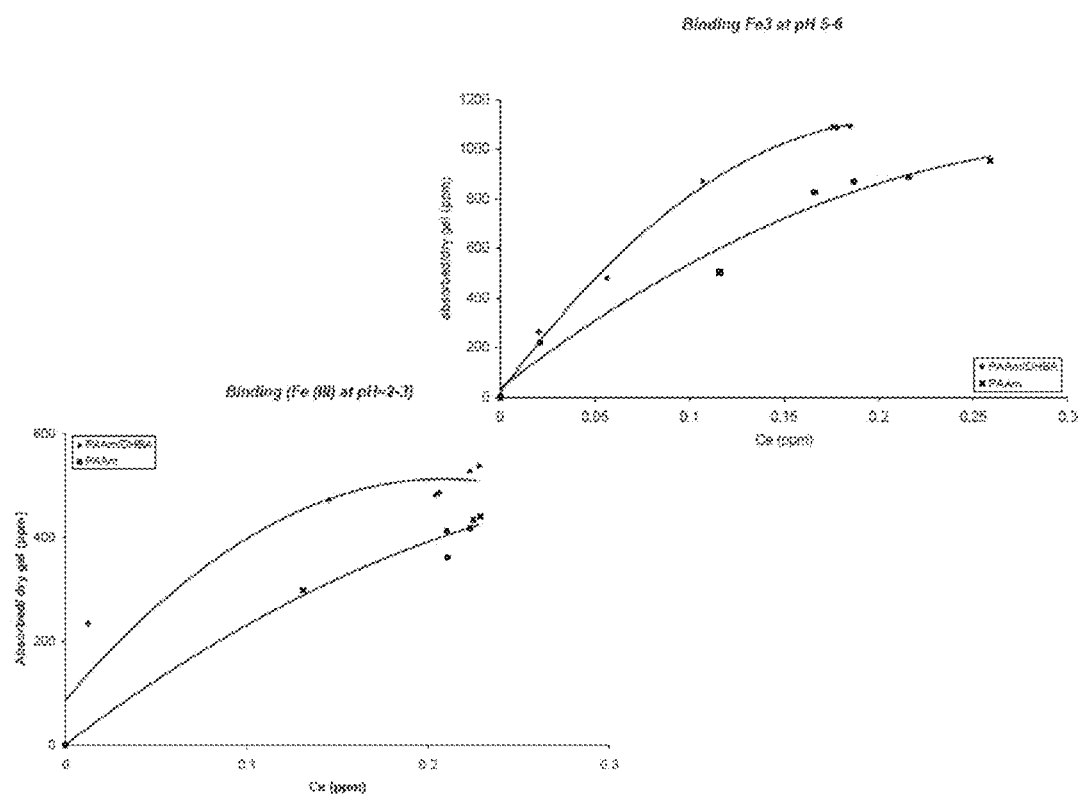

FIG. 17 is a chart depicting the selectivity of a polymer.
FIG. 18 is a chart depicting the selectivity of a polymer.
FIG. 19 is a chart depicting the selectivity of a polymer.
FIG. 20 is a chart depicting the selectivity of a polymer.
FIG. 21 is a table depicting the selectivity of a polymer.
FIG. 22 is a table depicting the selectivity of a polymer.
FIG. 23 is a table depicting the selectivity of a polymer.
FIG. 24 is a chart depicting the binding properties of a polymer.

Figure 25:
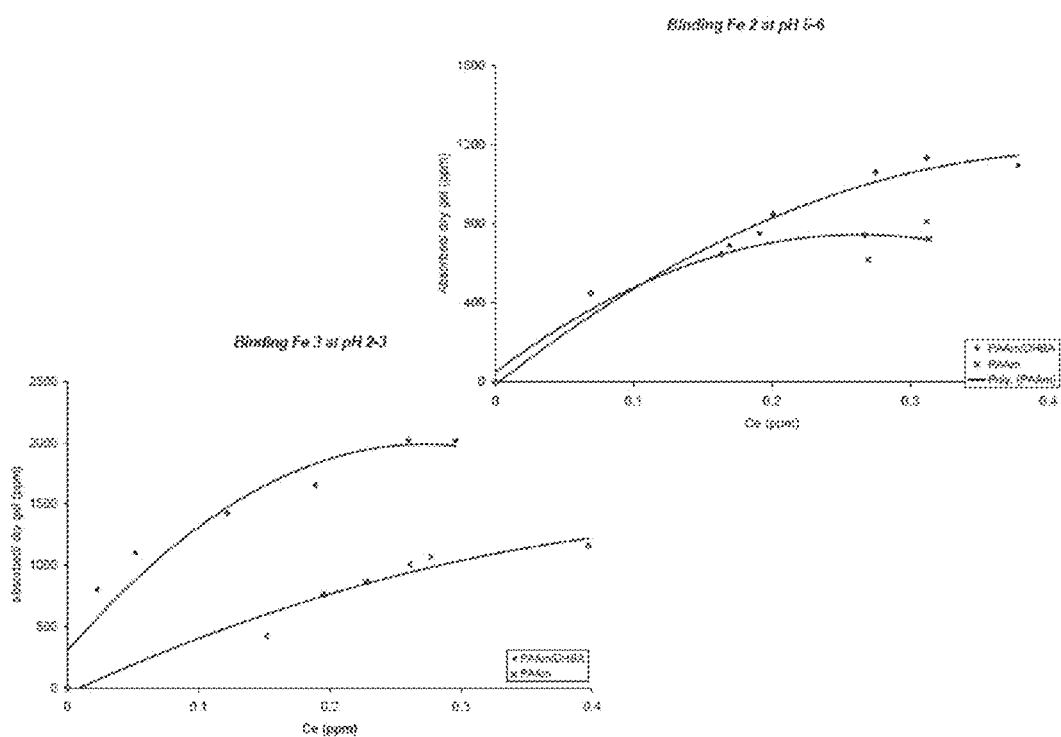

FIG. 25 is a chart depicting the binding properties of a polymer.

Figure 26:
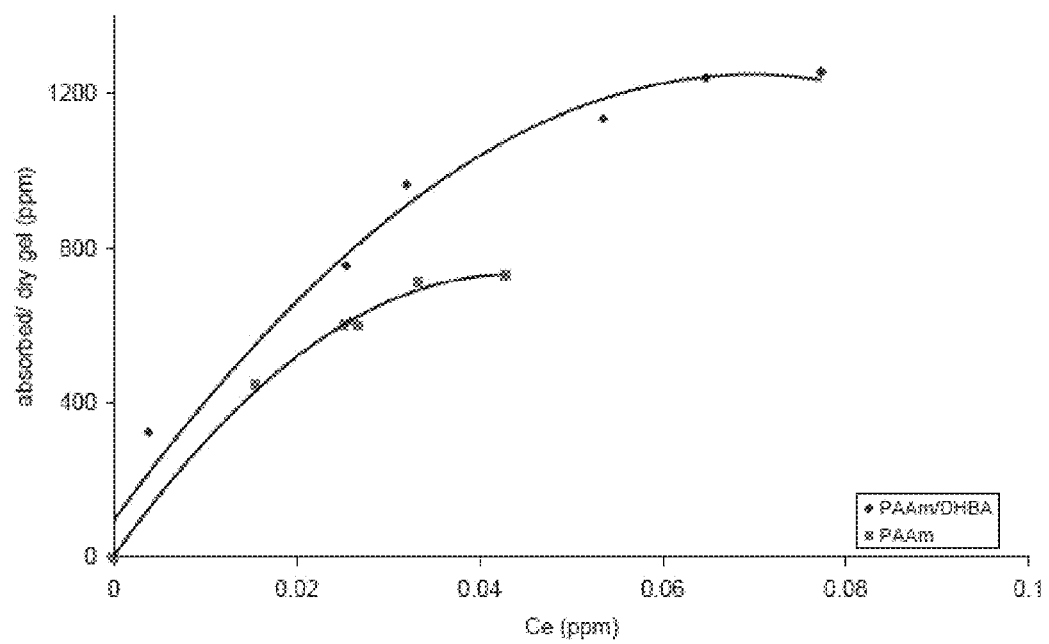

FIG. 26 is a chart depicting the binding properties of a polymer.

Figure 27:
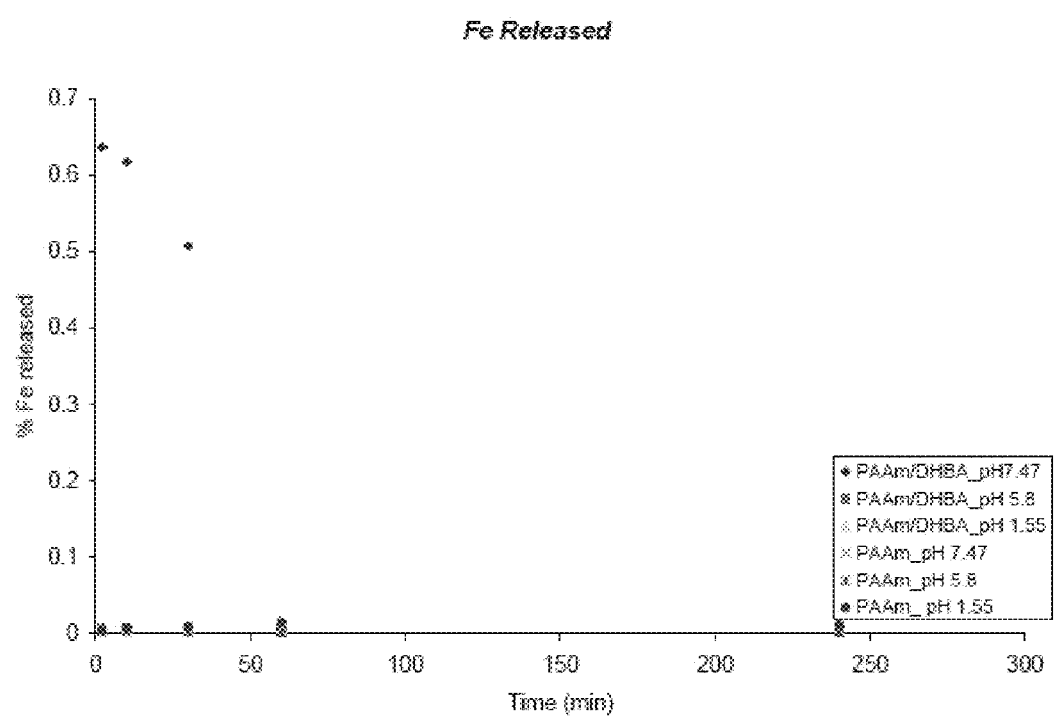

FIG. 27 is a chart depicting the binding properties of a polymer.

Figure 28:
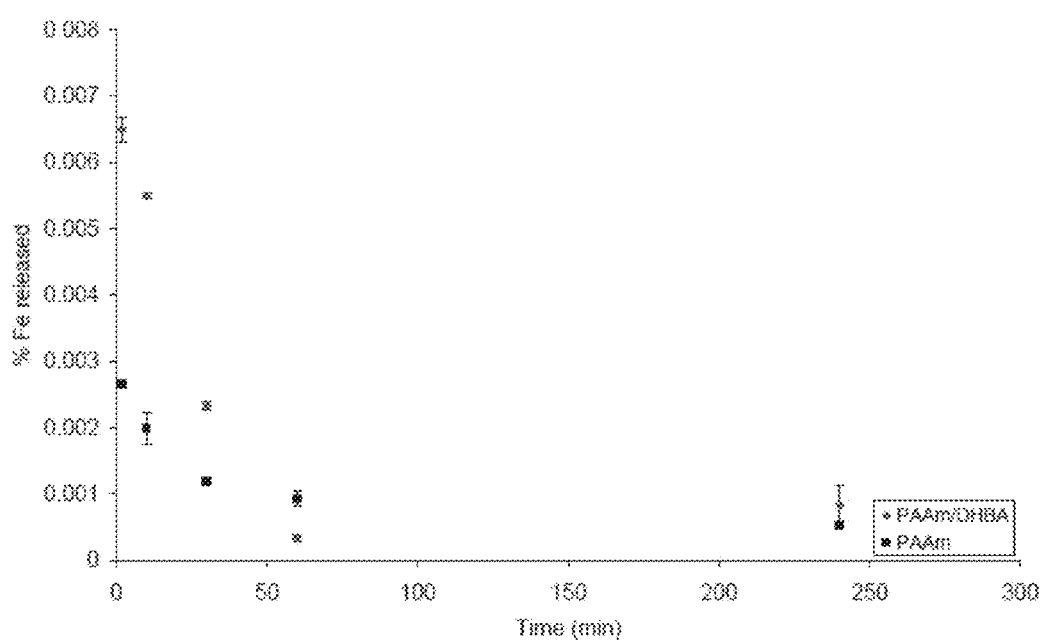

FIG. 28 is a chart depicting the binding properties of a polymer.

Figure 29:
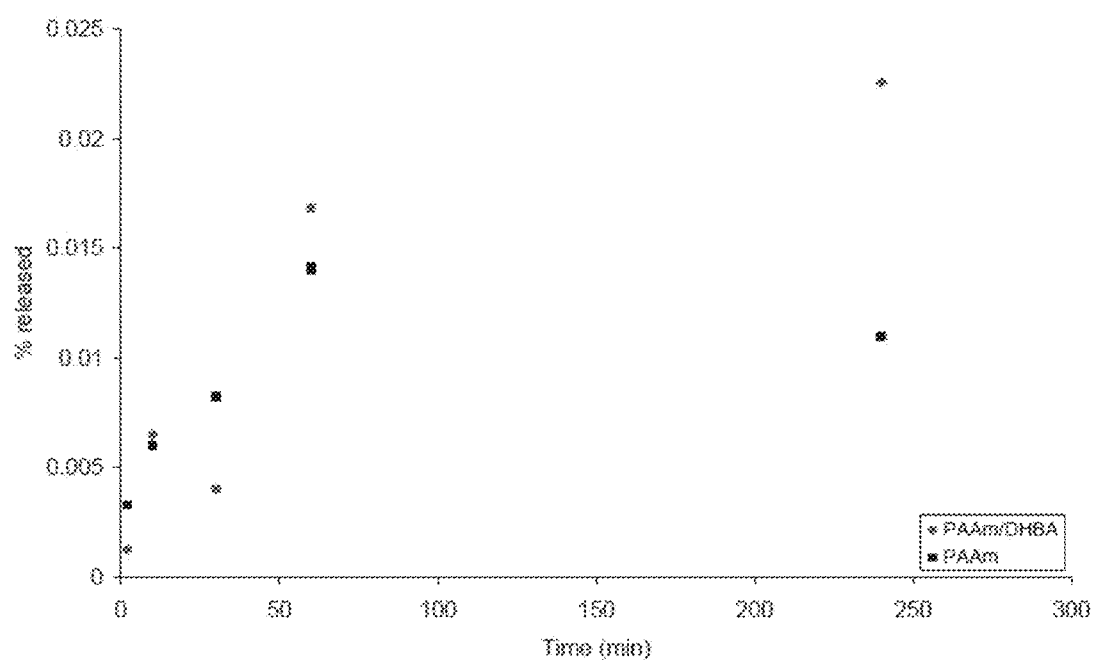

FIG. 29 is a chart depicting the binding properties of a polymer.

Figure 30:
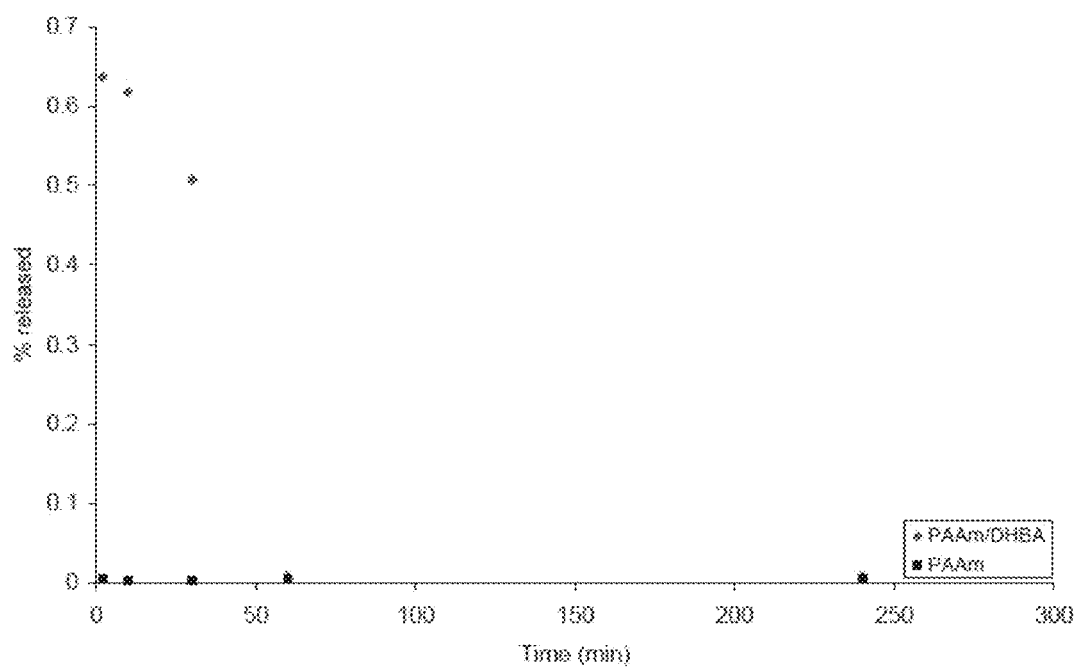

FIG. 30 is a chart depicting the binding properties of a polymer.

Figure 31:
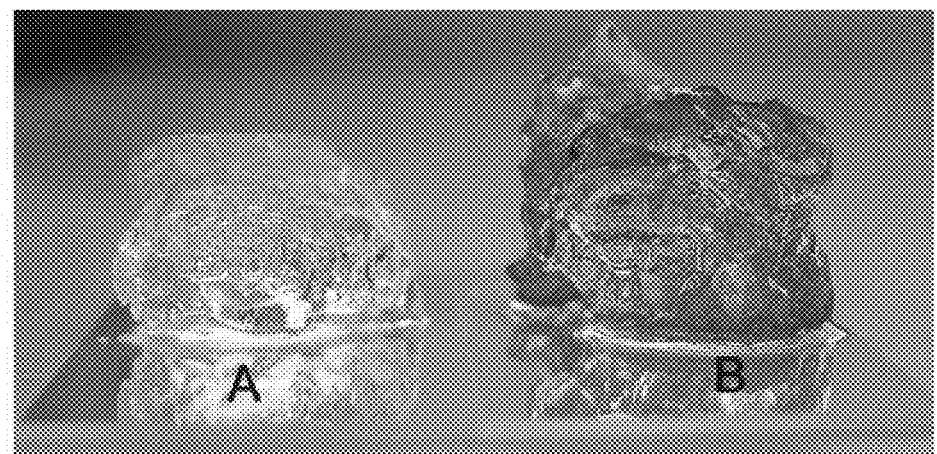

FIG. 31 includes photographs demonstrating the swelling properties of polymers.

Figure 32:
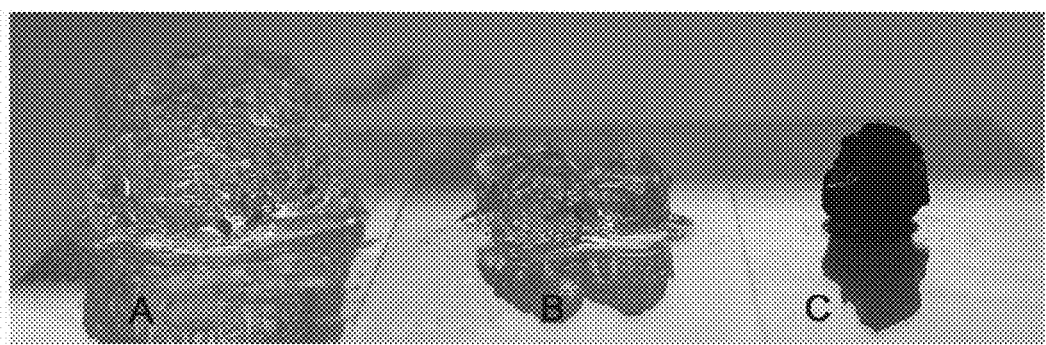

FIG. 32 includes photographs demonstrating the swelling properties of polymers.

Figure 33:
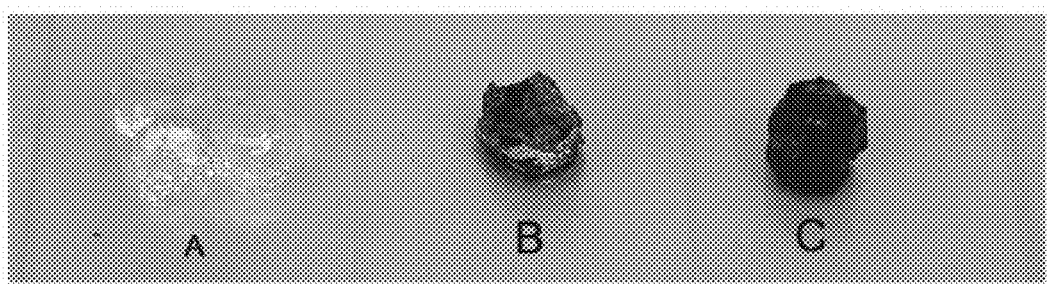

FIG. 33 includes photographs demonstrating the swelling properties of polymers.

FIG. 34 includes photographs demonstrating the swelling properties of polymers.

Figure 35:
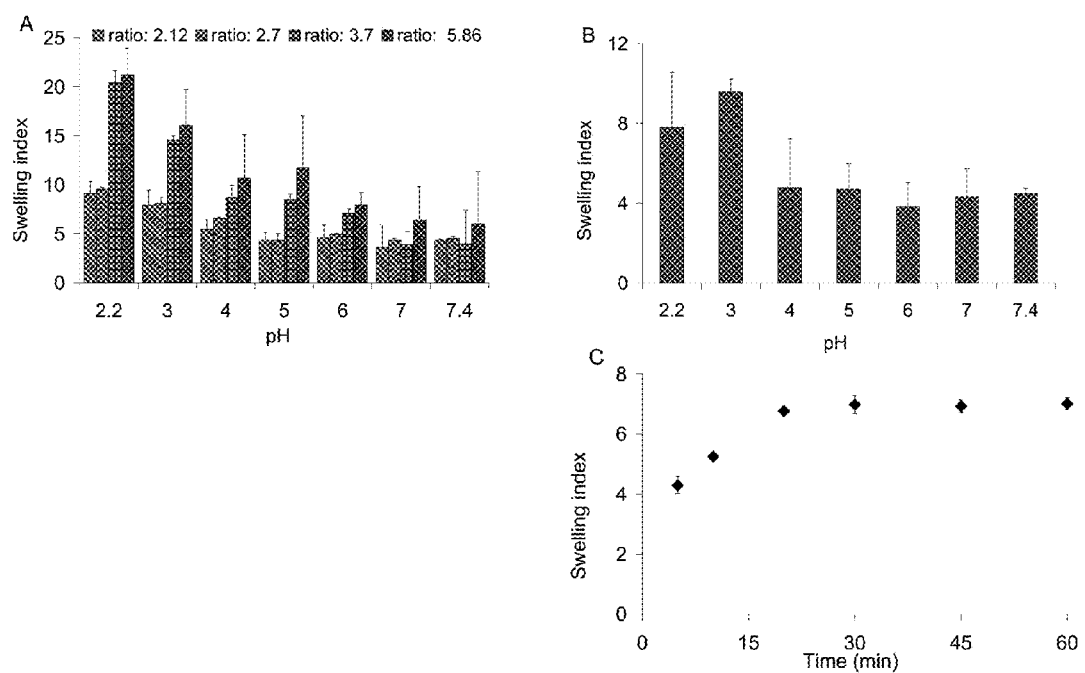
Figure 36:
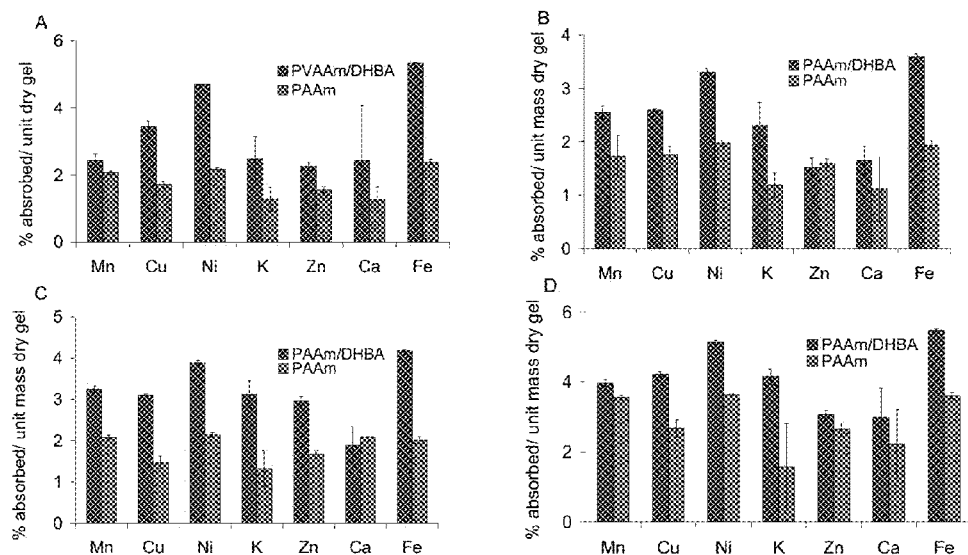

FIGS. 35A-C are charts depicting the swelling index of siderophore mimetic gels.

FIGS. 36A-D are charts depicting the results of selectivity studies for PAAm/DHBA and PAAm hydrogels.

Figure 37:
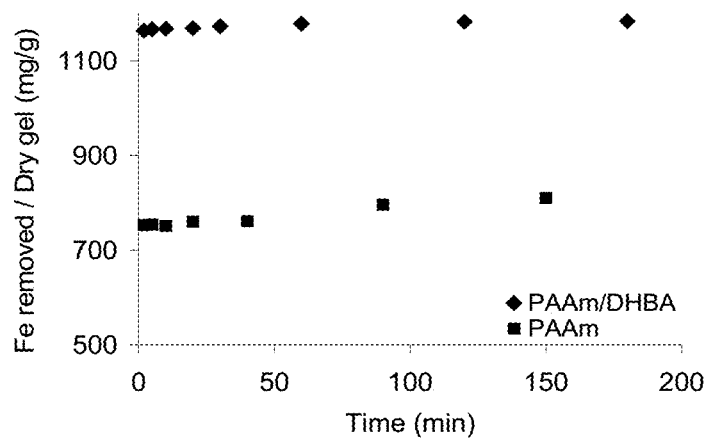

FIG. 37 is a chart depicting ion binding by chelating gels.

Figure 38:
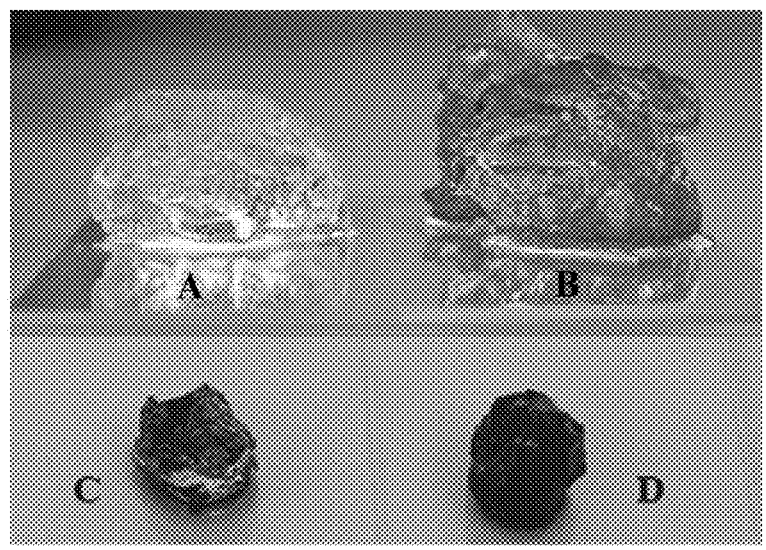

FIG. 38 includes photographs of chelating gels.

Figure 39:
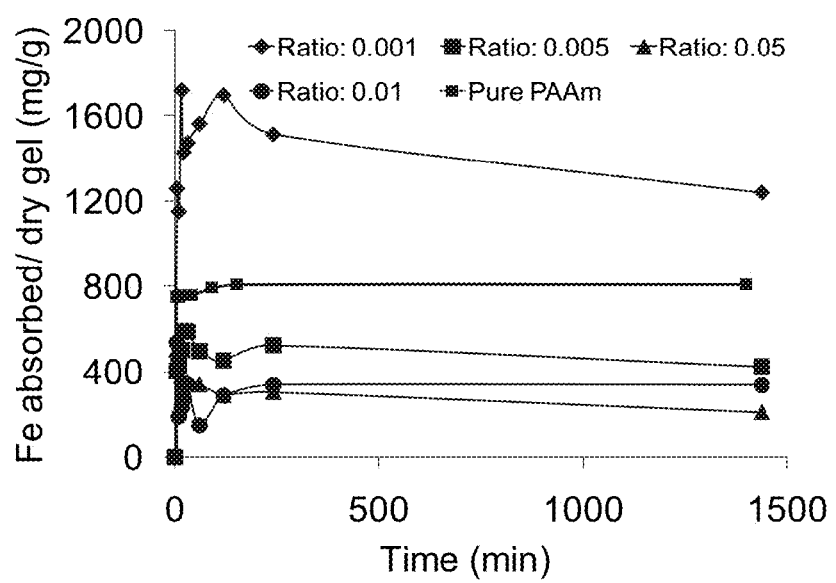

FIG. 39 is a chart depicting the results of kinetic studies of PAAm-DHBA hydrogels.

Figure 40:
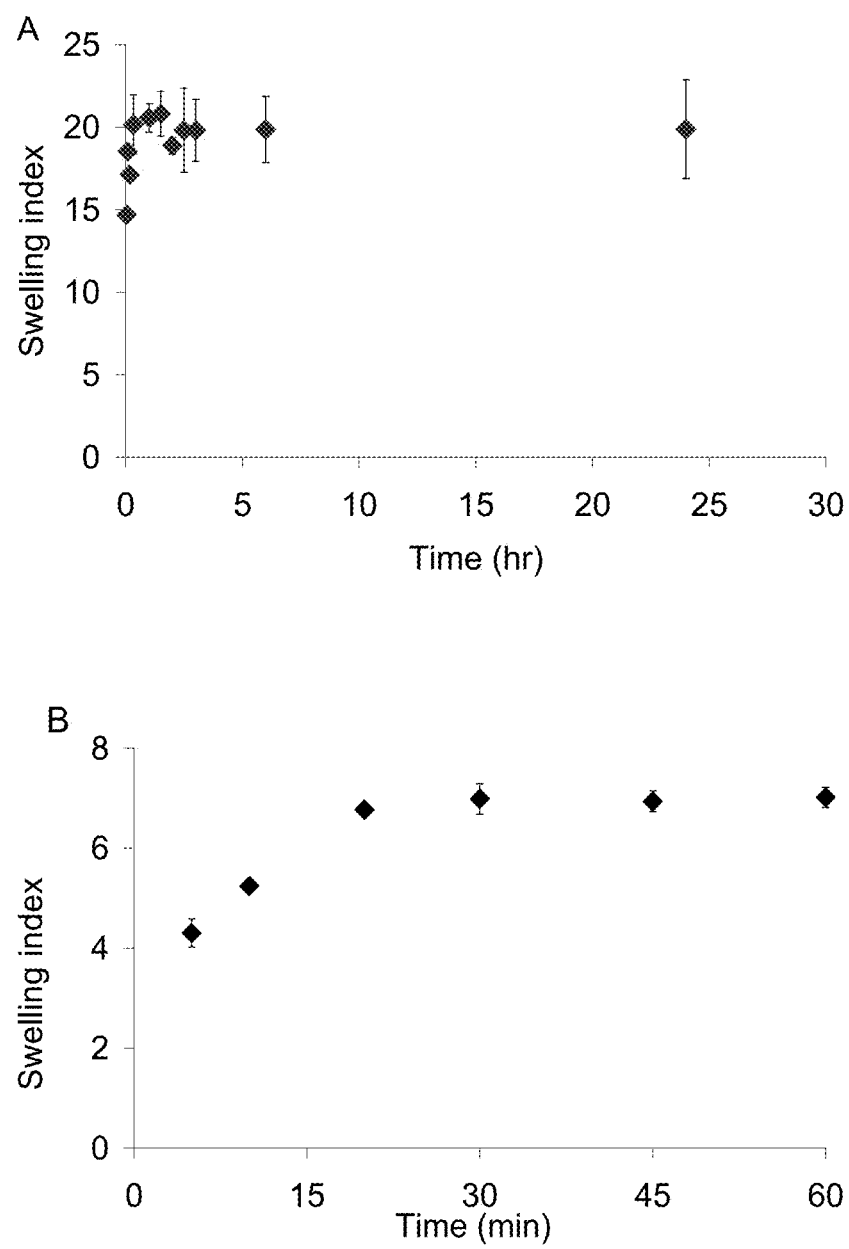

FIGS. 40A and 40B are charts depicting kinetic swelling data for PAAm and PAAm/DHBA hydrogels.

Figure 41:
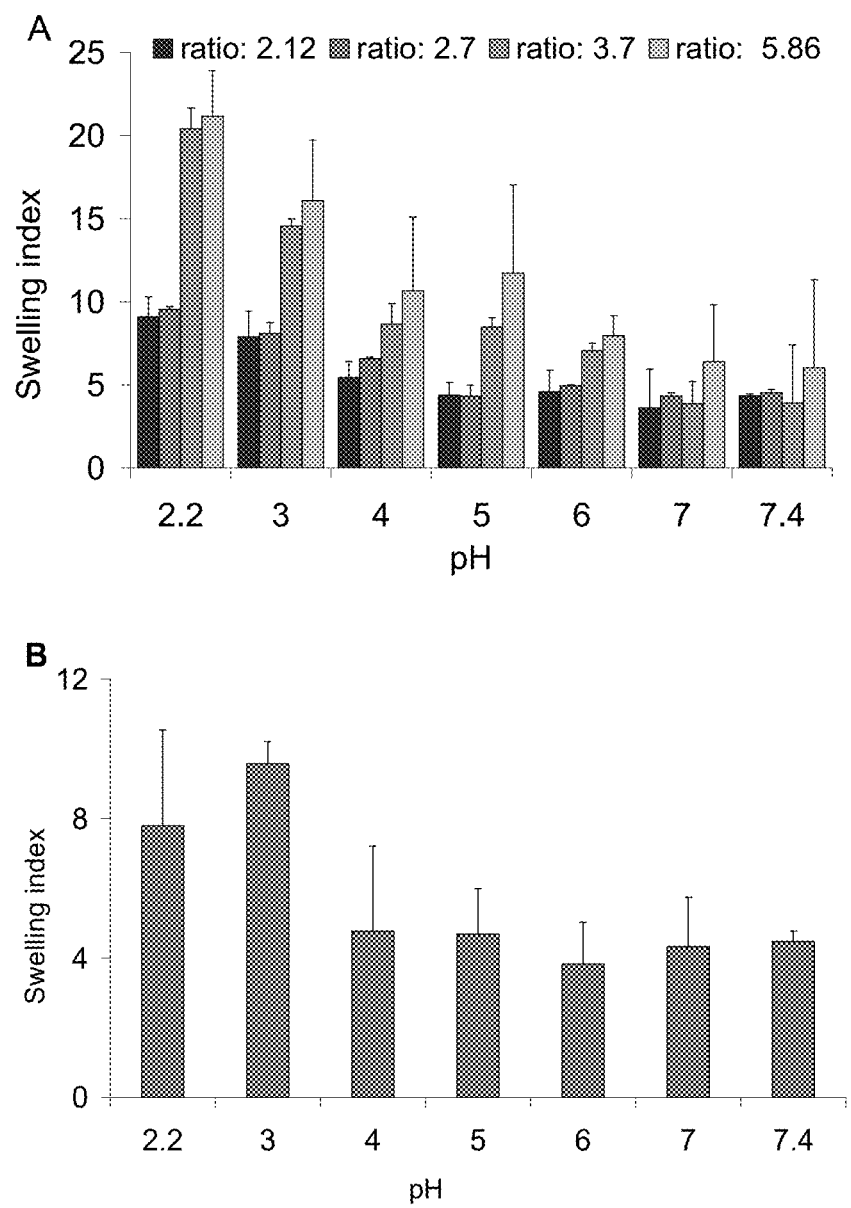

FIGS. 41A and 41B are charts depicting the swelling index of PAAm hydrogels.

FIGS. 42A-D includes photographs of chelating gels.

Figure 43:
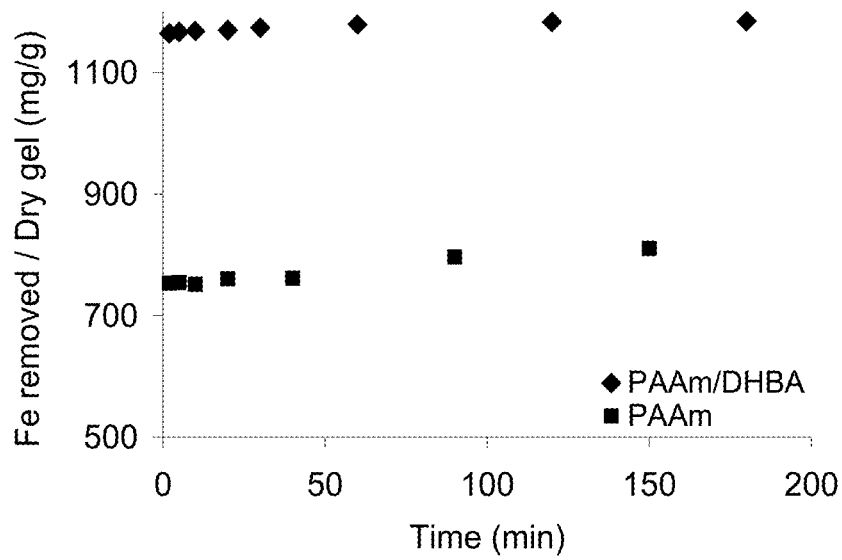

FIG. 43 is a chart depicting ion binding by PAAm/DHBA hydrogels.

Figure 44:
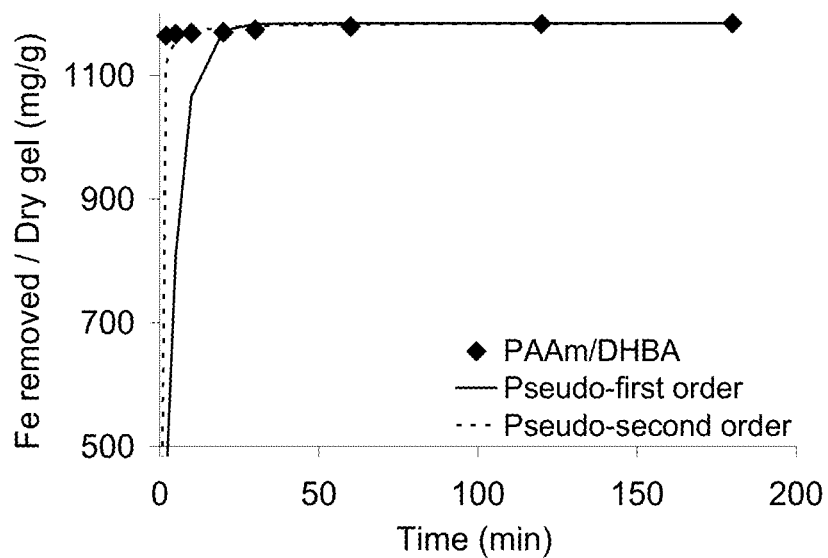

FIG. 44 is a chart depicting kinetic models fitted for PAAm/DHBA hydrogel.

Figure 45:
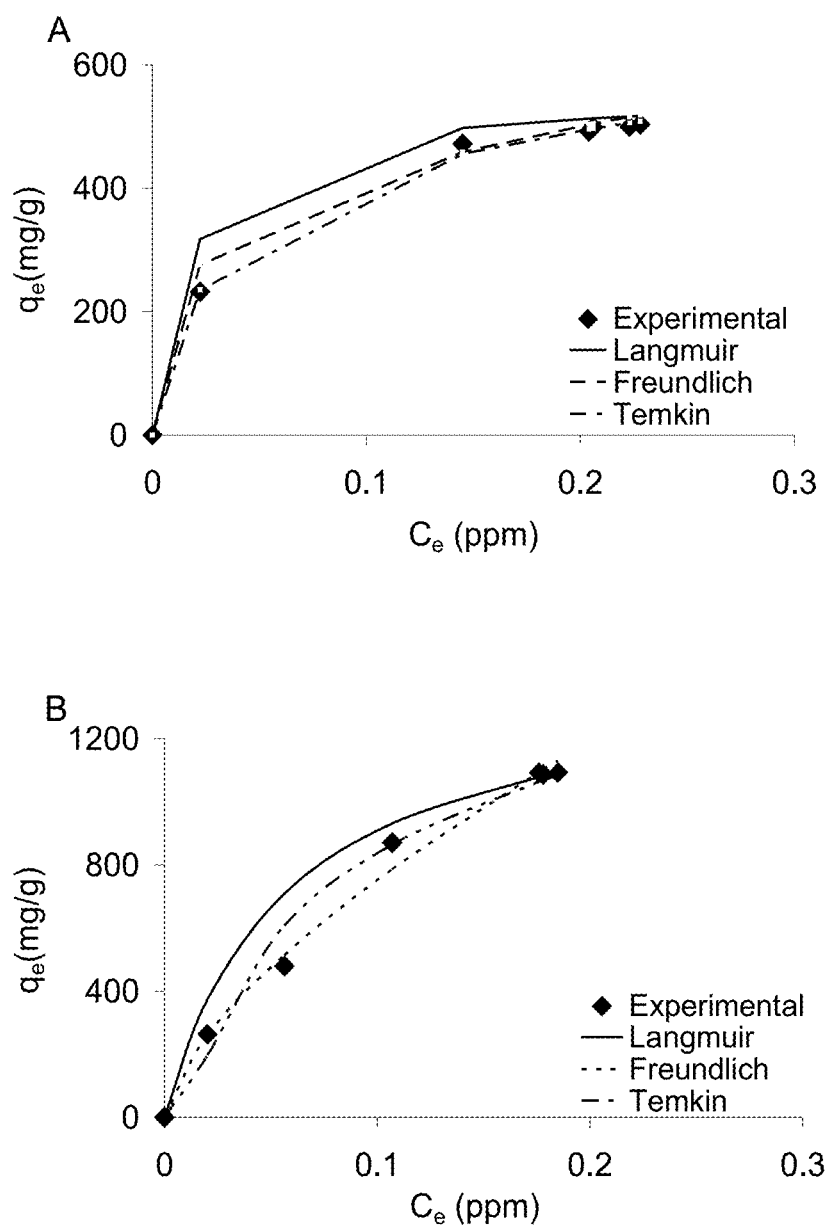

FIG. 45 is a chart depicting binding isotherms for ferric ions.

Figure 46:
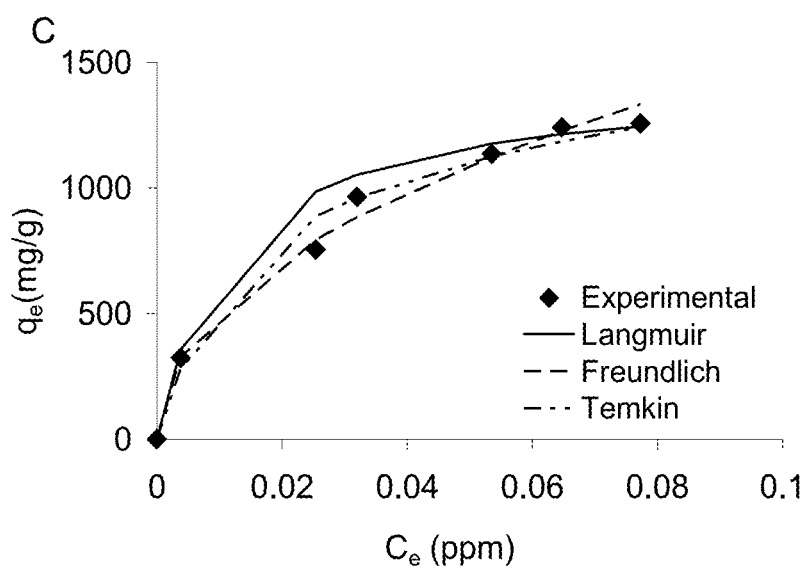

FIG. 46 is a chart depicting binding isotherms for ferric ions.

Figure 47:
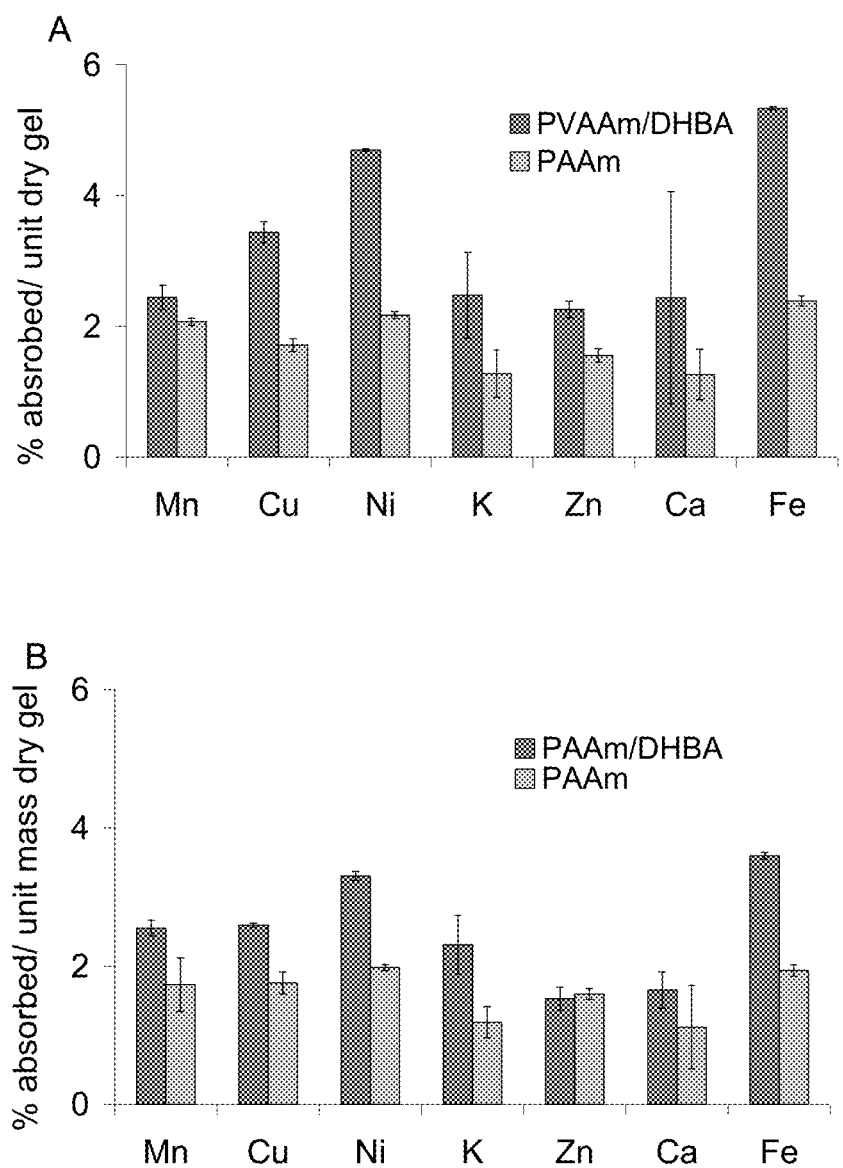

FIG. 47 is a chart depicting the results of a selectivity study for PAAm/DHBA and PAAm hydrogels toward ferric ion.

Figure 48:
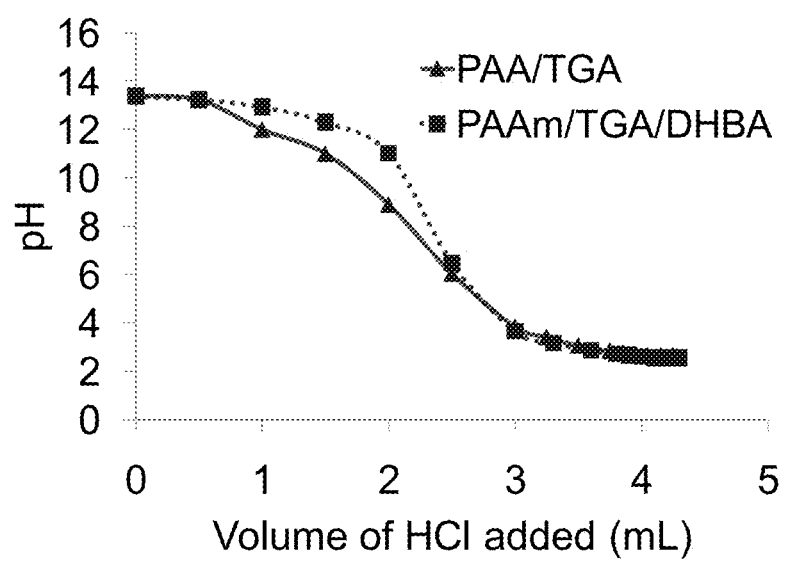

FIG. 48 is a chart depicting titration data collected for PAAm/TGA and PAAm/TGA/DHBA.

Figure 49:
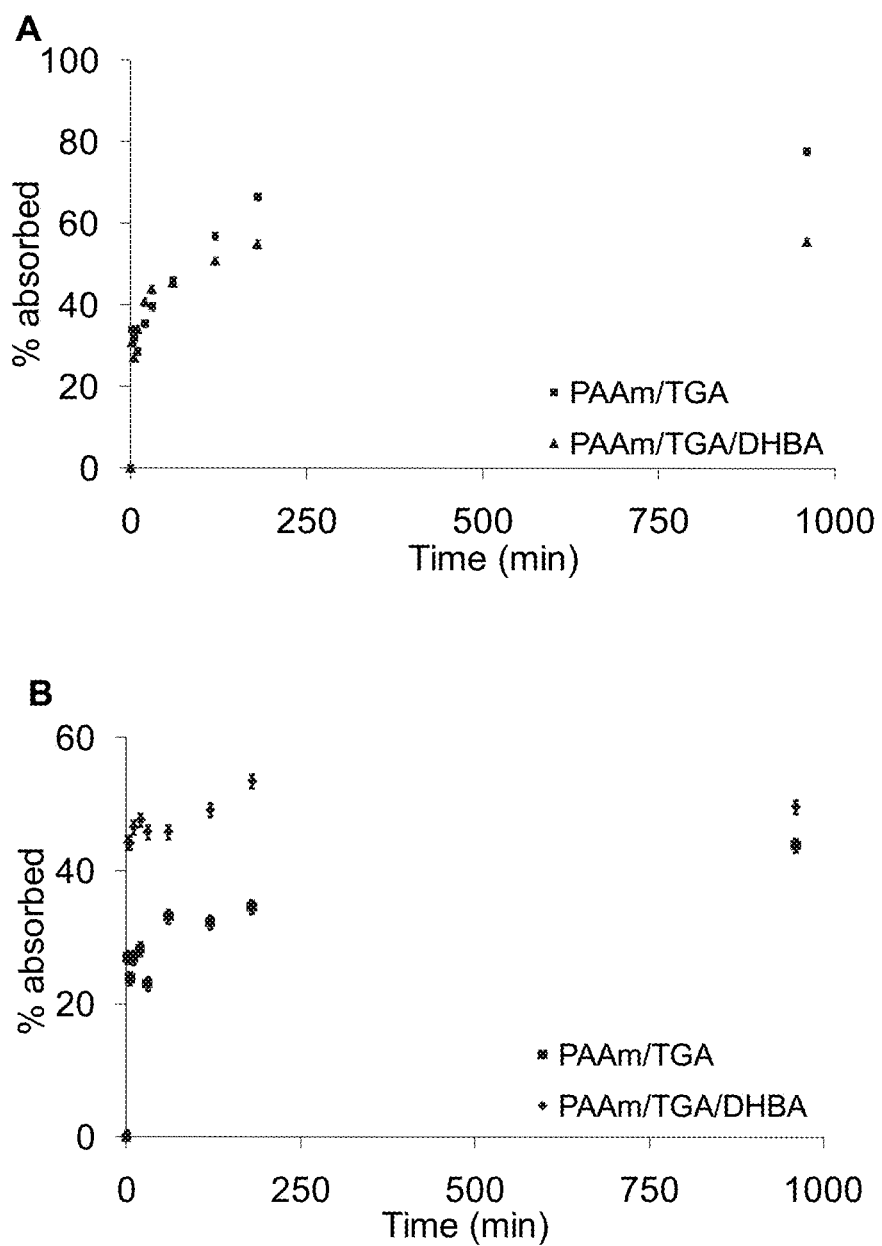
Figure 49:
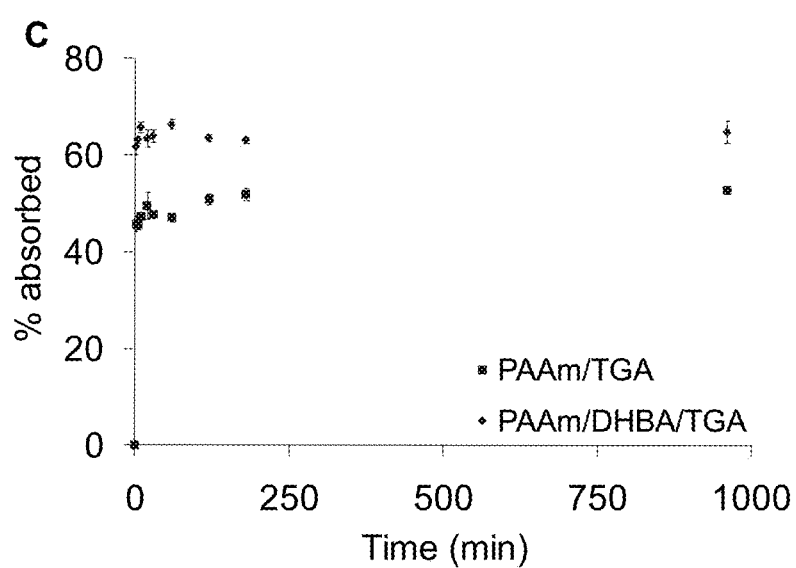

FIG. 49 includes charts depicting ion binding by functionalized hydrogels.

FIG. 50 includes charts depicting selectivity studies of functionalized hydrogels toward toxic metal ions.

Figure 51:
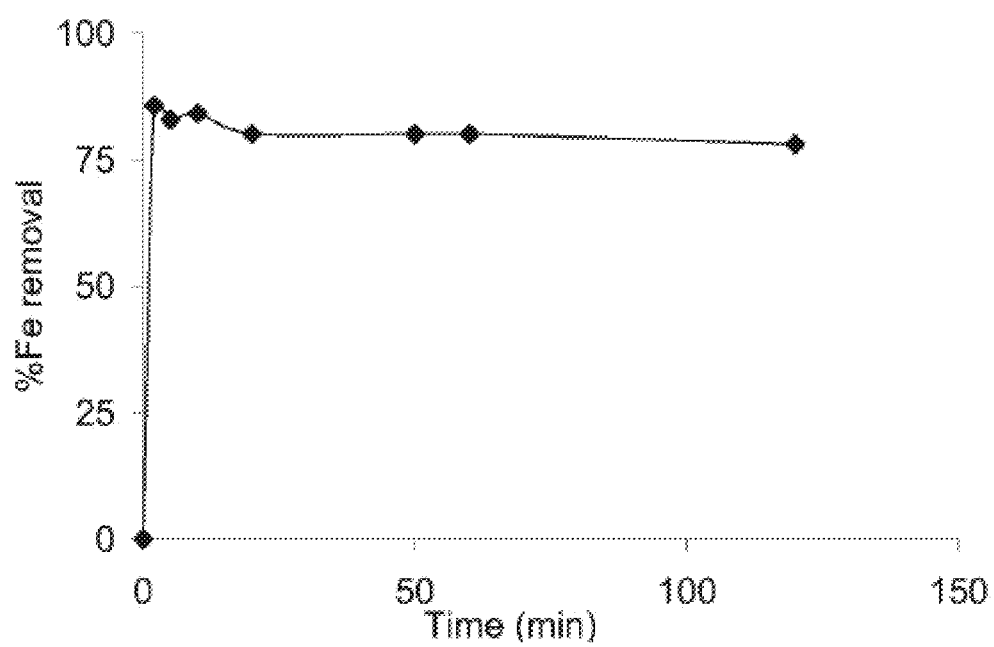

FIG. 51 is a chart depicting kinetic data.

Figure 52:
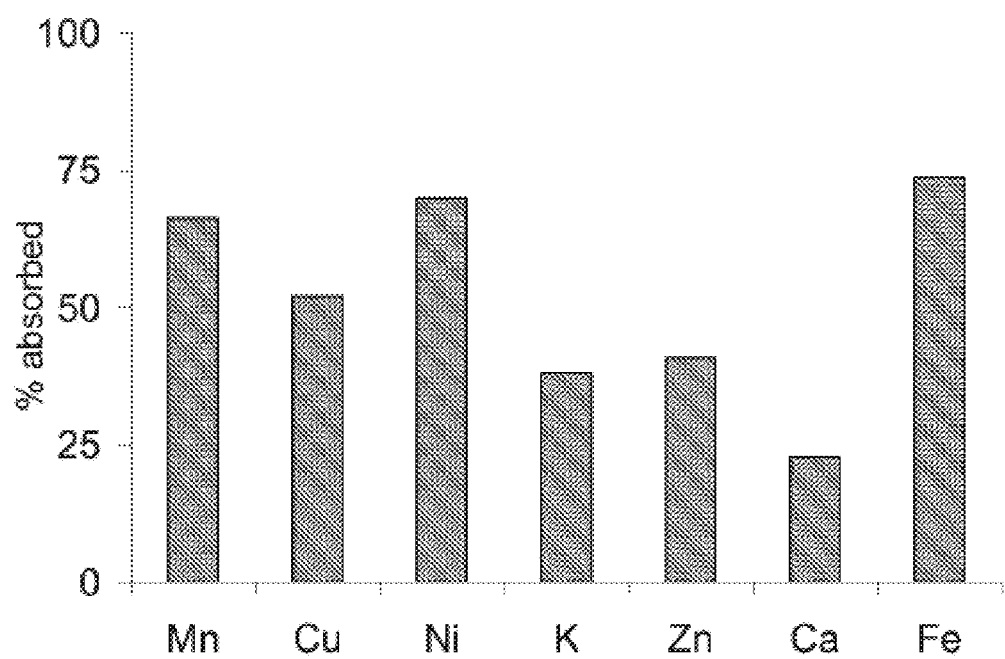

FIG. 52 is a chart depicting the results of a selectivity study.

Figure 53:
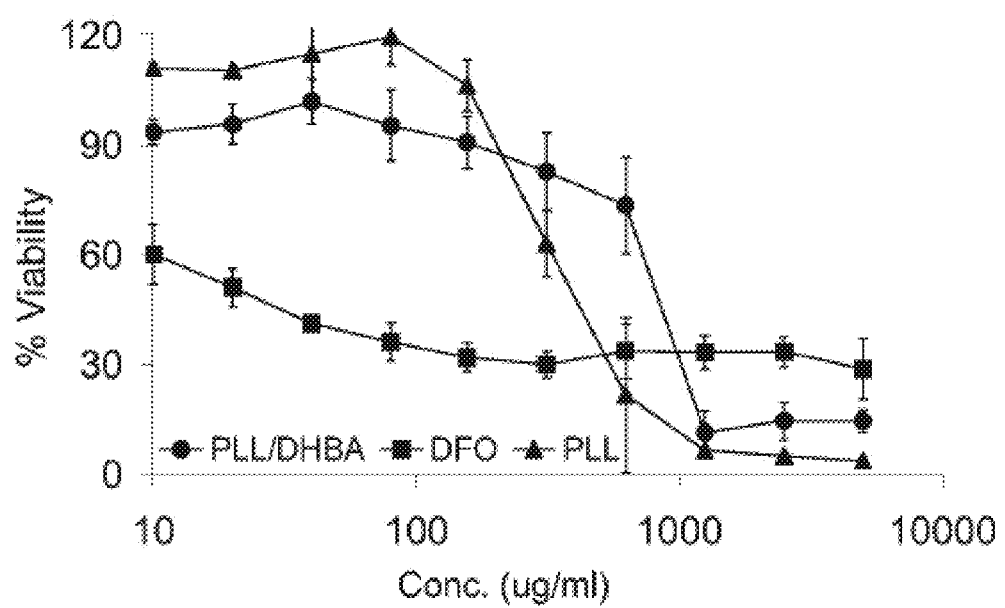

FIG. 53 is a chart depicting the results of a cytotoxicity study conducted on HUVEC cell.

Figure 54:
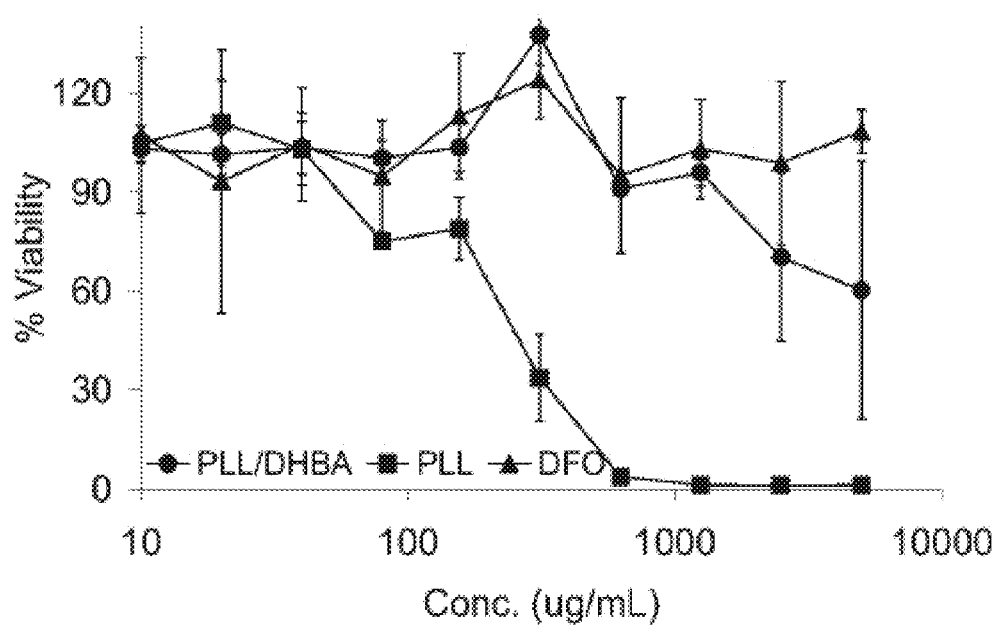

FIG. 54 is a chart depicting the results of a cytotoxicity study conducted on A549 cell.

Figure 55:
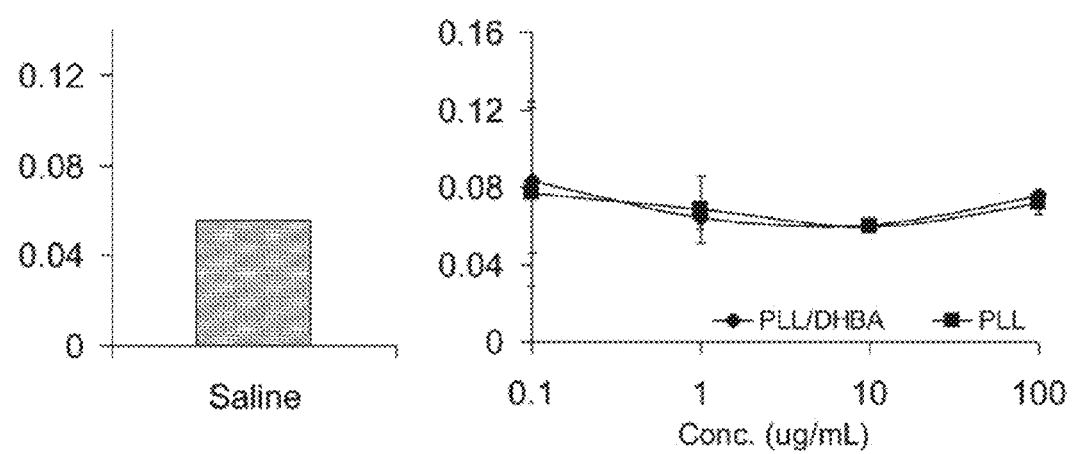

FIG. 55 is a chart depicting the hemolytic activities of PLL and PLL/DHBA.

Figure 56:
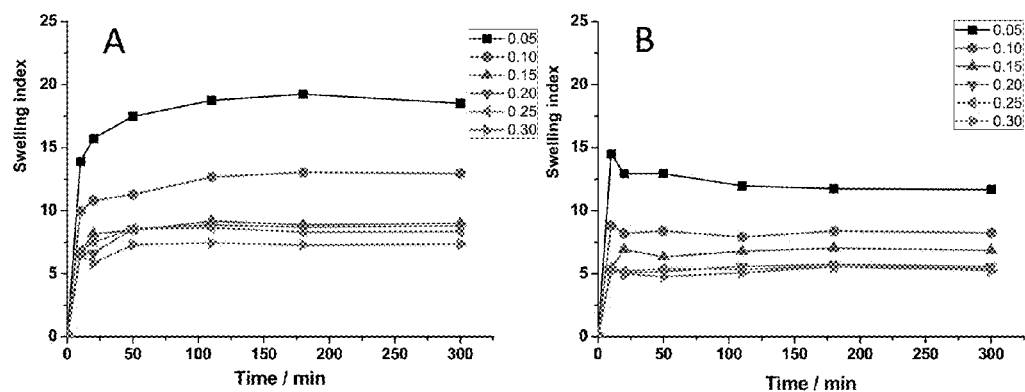

FIG. 56 are charts depicting kinetic swelling data for PAAm-DHBA gels with various DHBA content (0.05-0.30) in pH 2 buffer (A) and pH 7.4 buffer (B). Increasing DHBA reduces swelling.

Figure 57:
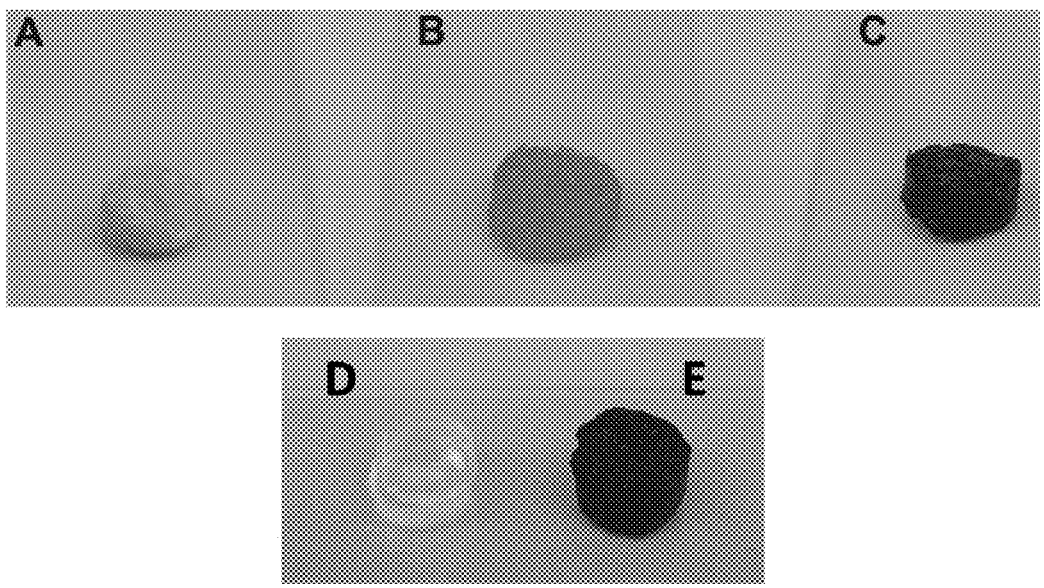

FIG. 57 are photographs showing (A) PAAm-DHBA dry gel; (B) PAAm-DHBA gel equilibrated in pH 2 buffer; (C) PAAm-DHBA gel equilibrated in 0.5 mM Ferric solution (pH 2); (D) PAAm gel equilibrated in 0.5 mM Ferric solution and washed with water; and (E) PAAm-DHBA gel equilibrated in 0.5 mM Ferric solution and washed with water. The color of the gel is due to the oxidation of phenol groups.

Figure 58:
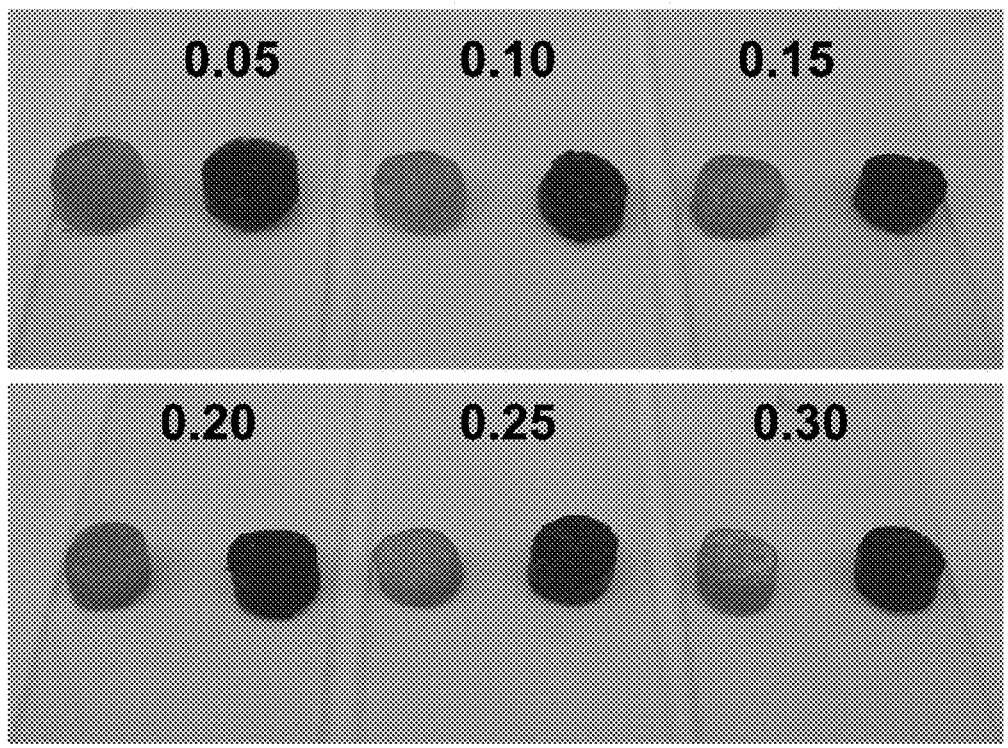

FIG. 58 are photographs showing PAAm-DHBA gels with different concentrations of DHBA equilibrated in PBS buffer (pH 7.4). The gel on the right contains 0.5 mM $Fe^{3+}$.

FIG. 59 are photographs and a schematic showing color changes of PAAm gel in PBS buffer (pH 7.4) containing 1.0 mM $Fe^{3+}$ over time.

Figure 60:
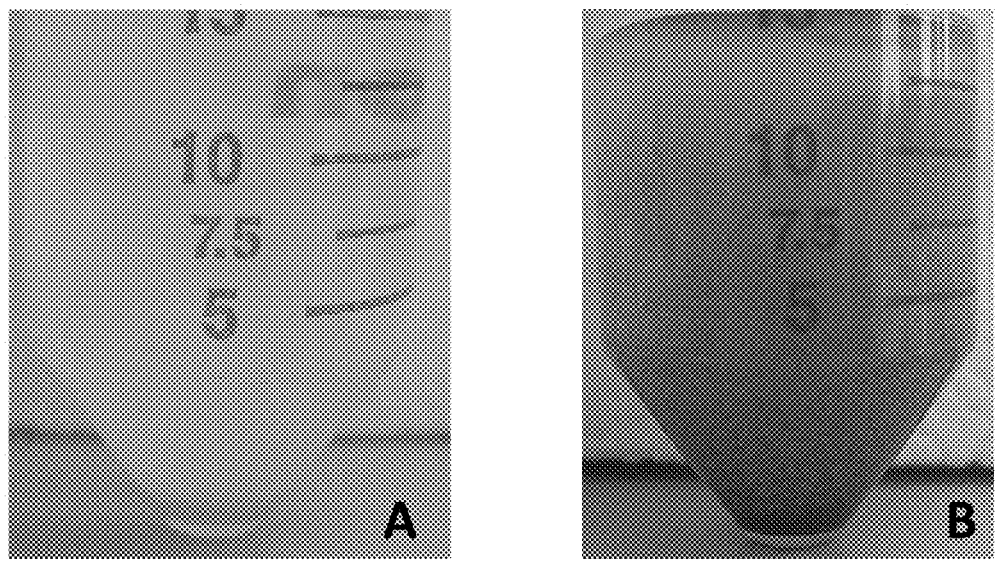

FIG. 60 are photographs showing (A) Ground PAAm-DHBA gel in pH 7.4 buffer without $Fe^{3+}$ and (B) ground PAAm-DHBA gel in pH 7.4 buffer with adding $Fe^{3+}$ for 30 sec.

Figure 61:
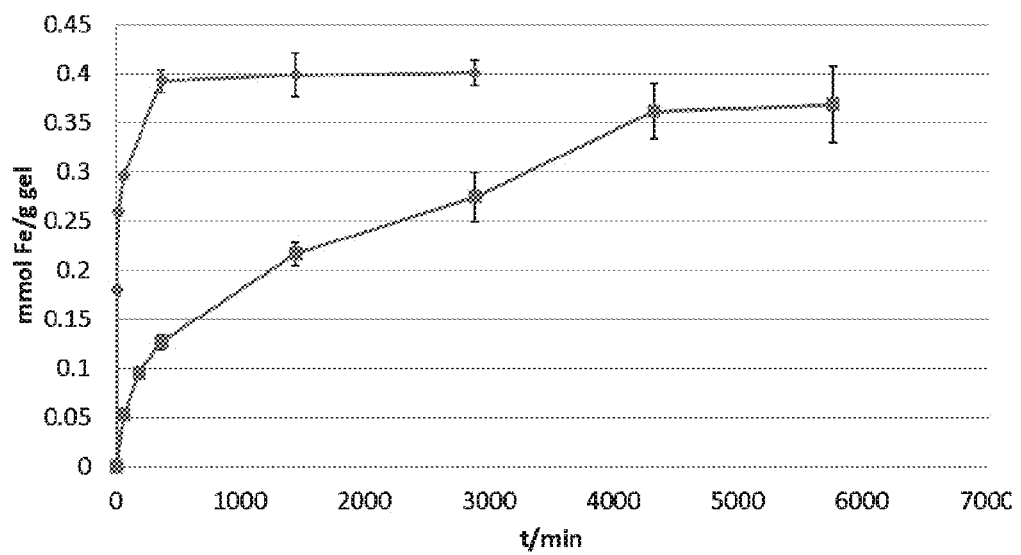

FIG. 61 is a graph depicting a kinetic study of iron adsorption by tablets and ground tablets. The ground powders only take less than 10 min to reach 50% of maximum iron adsorption; while the tablet takes about 15 h.

Figure 62:
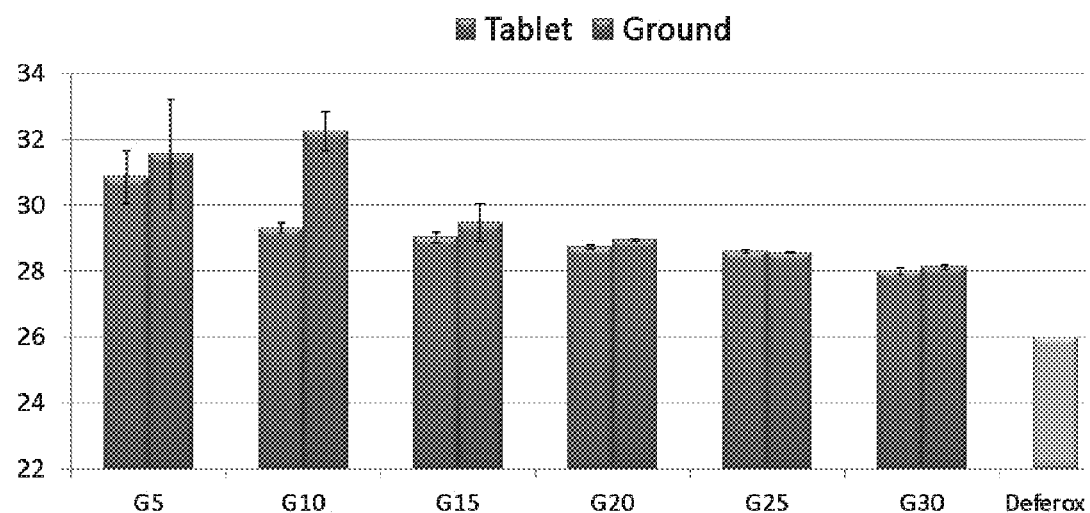

FIG. 62 is a chart showing iron binding constant for DHBA gels is higher than deferoxamine.

Figure 63:
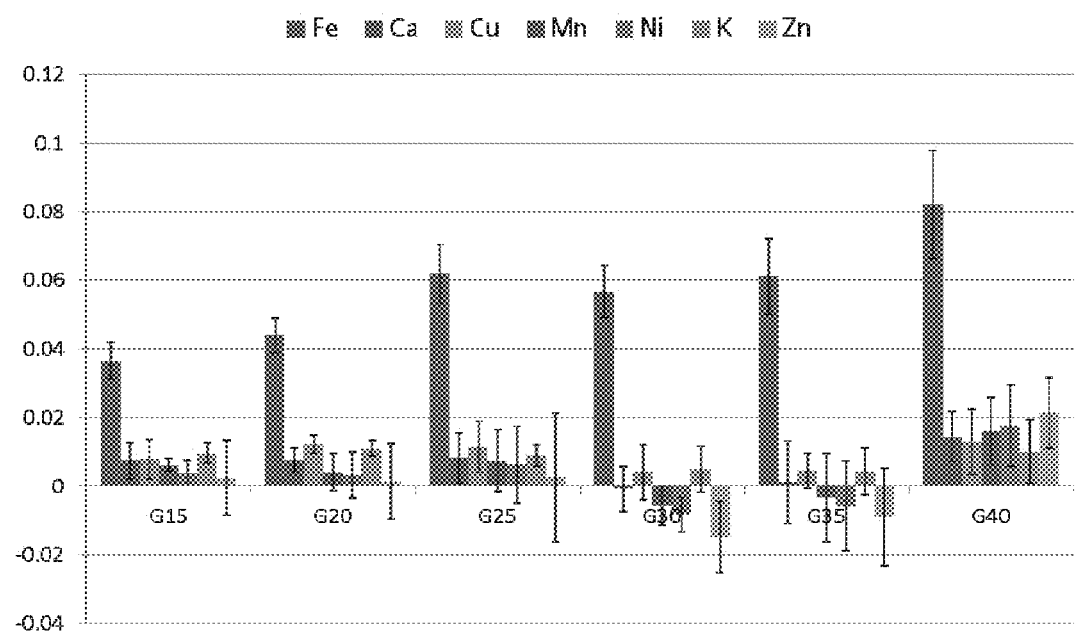

FIG. 63 is a chart showing metal selectivity studies for PAAm-DHBA gels with various DHBA content (0.15-0.40) in pH 2 buffer. All the metals have the same initial concentration (0.4 mM) for the study. All the samples tested showed excellent selectivity of Fe over other metals.

Figure 64:
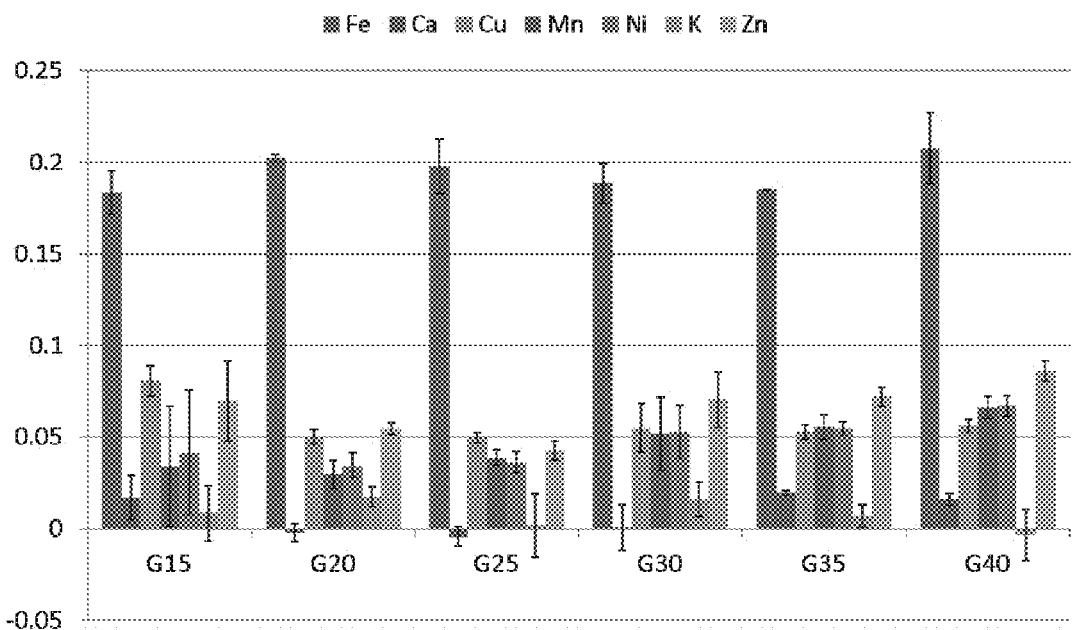

FIG. 64 is a chart showing Metal selectivity studies for PAAm-DHBA gels with various DHBA content (0.15-0.40) in pH 7.2 buffer. All the metals have the same initial concentration (0.4 mM) for the study. EDTA (3 mM) was added to maintain the $Fe^{3+}$ in solution. All the samples tested showed excellent selectivity of Fe over other metals.

Figure 65:
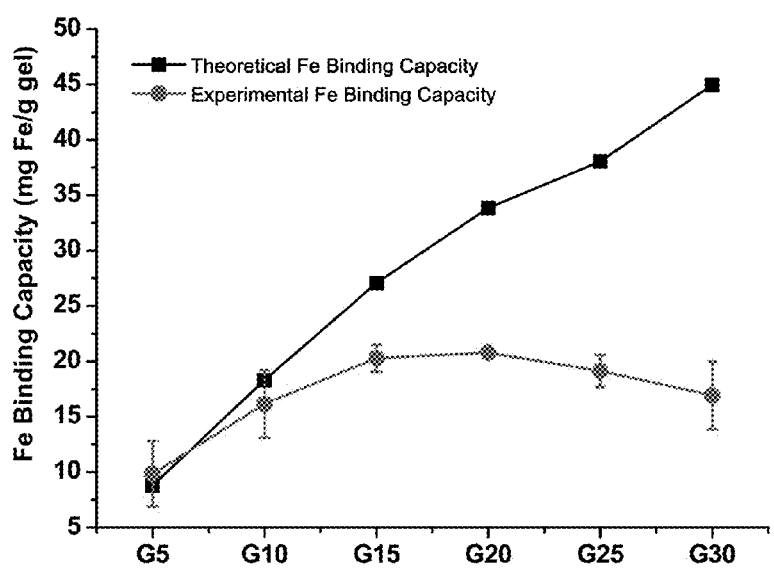

FIG. 65 is a graph showing iron binding capacity of PAAm-DHBA gels as a function of DHBA content.

DESCRIPTION

Generally, the present invention includes new compositions and systems for chelation of metals. In some embodiments, the present invention provides a composition comprising a polymeric chelator. The polymeric chelator can include a polymer coupled with a metal chelator. The system can include a polymer and a metal chelator that can be coupled together or otherwise linked so as to combine the properties of the polymer and the ability to chelate a metal.

In some embodiments, the polymer that is coupled with a metal chelator may include any polyamine polymer such as polyallylamine (PAA), polyvinyl formamide (PVF), polyvinylamide (PVA), polylysine (PLL), polyethylenimine (PEI), or the like. The polymer may also include amino acids, and the polymer can include polypeptides and proteins.

In some embodiments, any polymer may be used that is capable of being coupled to a chelator, such as an iron chelator, which can be used for chelation so as to combine the properties of the polymer with the ability to chelate. The polymers can be any type of polymer that is linear, branched, crosslinked, hydrogel, or the like or a soluble polymer, a non-soluble polymer, a cross-linked polymer, an un-cross-linked polymer, or the like. The polymers can include polyamines that have amine functional groups capable of participating in reactions with chelators. In some examples the polymer may comprise polyamine polymers such as PVAm and PAAm. PVAm and PAAm are polycation hydrogels consisting of reactive primary amine side groups for the conjugation of the chelator. In some embodiments, the cross-linked PVAm hydrogel may be synthesized by hydrolyzing a precursor polymer, PNVF, in a basic medium. In some embodiments, cross-linked PAAm hydrogel may be synthesized by cross-linking the precursor PAAm chains. Both hydrogels may demonstrate a high affinity and selectivity for iron at pHs similar to those found in the GI tract.

Figures 1A, 1B:
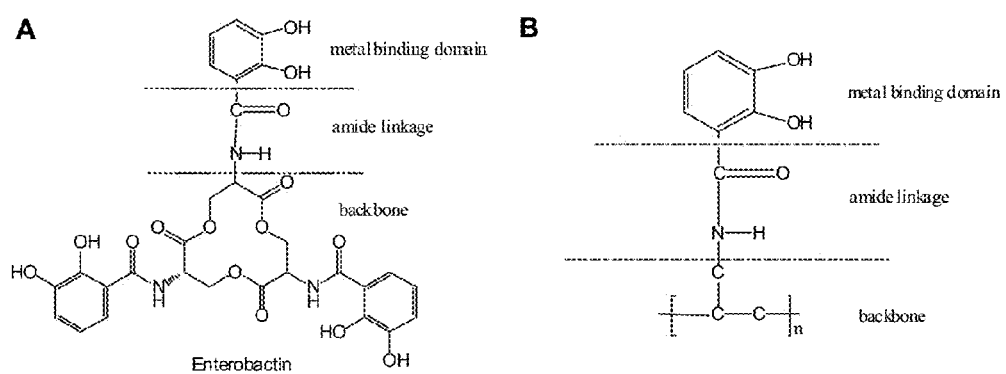
FIGS. 1A and 1B depict structural diagrams of Enterobactin and a polymeric chelator.

In some embodiments, the chelator coupled to the polymer may include 2,3 dihydrobenzoic acid (DHBA) and other iron chelators. 2,3 DHBA acid is a fraction of the well known natural iron chelator Enterobactin (Log K=52) which is a high affinity siderophore that acquires iron for microbial systems. FIG. 1A depicts a structural diagram of Enterobactin. Chelators of other metals that can be coupled to a polymer may also be included.

In some embodiments, the chelator may be coupled to the polymer via a carboxyl group of the chelator. In some embodiments, the chelator may be coupled to the polymer via a peptide bond. In some embodiments, the chelators can include a feature for coupling with the polymer, such as carboxy groups that can be coupled to the amines of the polymer through amide bonds. Other crosslinking or coupling reagents can be included in the polymer and chelator system in order to prepare a polymeric chelator having the ability to chelate iron. Examples of iron chelating small molecules are referenced in U.S. Pat. No. 3,758,540. Examples of chelator schemes may be found in U.S. Pat. Nos. 7,342,083, 5,702,696, and 5,487,888.

In some embodiments, the present disclosure provides a polymeric chelator, polymer or hydrogel, made by reacting 2,3 dihydroxybenzoic acid (DHBA), a known iron chelator, to a polyamine polymer. FIG. 1B depicts a structural diagram of such a polymeric chelator formed by reacting a chelator with a polyamine polymer.

In some embodiments, the polymeric chelators, in polymer or hydrogel form, can be fabricated as solids or equilibrated in aqueous solution as a solution or suspension. The polyamine conjugates have exceptional binding affinity and selectivity for iron. In some examples the polyamine polymer may comprise PVAm and PAAm. PVAm and PAAm are polycation hydrogels consisting of reactive primary amine side groups for the conjugation of 2,3 DHBA. 2,3 DHBA acid is a fraction of the well known natural iron chelator Enterobactin (Log K=52) which is a high affinity siderophore that acquires iron for microbial systems. Cross-linked PVAm hydrogel may be synthesized by hydrolyzing a precursor polymer, PNVF, in a basic medium. Cross-linked PAAm hydrogel mat be synthesized by cross-linking the precursor PAAm chains. Both types of polymeric chelator hydrogels may demonstrate a high affinity and selectivity for iron at pHs similar to the GI tract.

In some embodiments, conjugation of 2,3 dihydroxybenzoic acid may facilitate the iron binding affinity and iron selectivity of the final hydrogel conjugates, the polymeric chelator. In some embodiments, the primary amine groups in both polymers may be used as a conjugation site. The non-degradable PVAm and PAAm hydrogels conjugated to 2,3 DHBA can be used as oral therapeutics in iron overload disease patients. This therapeutic agent can selectively bind iron and remove it from the GI tract before it is being absorbed into the blood stream.

In other embodiments, thioglycolic acids (TGA) in combination with the siderophore moiety dihydroxybenzoic acid (DHBA) may be introduced onto PAAm and PVA to from the polymeric chelator.

In one embodiment, the present invention provides for a composition comprising a monomer having the DHBA coupled thereto. The monomer can be coupled to the DHBA by the monomer having an amine group which reacts and couples with the carboxyl group of the DHBA. The monomer having the DHBA can be used in composition similarly to that which is described in connection with the polymer coupled to DHBA. Examples of suitable monomers include any monomer that is capable of being coupled to a chelator, such as an iron chelator. The monomer can be any type of monomer. The monomer can include amines that have amine functional groups capable of participating in reactions with chelators. In some examples the monomer may comprise amine monomers.

In one embodiment, a polymeric chelator can be made by reacting 2,3 DHBA to a polyamine polymer through the formation of an amide bond. The polyamine-DHBA chelating polymer has exceptional binding affinity and selectivity for iron.

The polymeric chelators can be fabricated as solids, gels, pastes, liquids, such as being equilibrated in aqueous solution as a solution or suspension.

In some embodiments, the polymeric chelators can be crosslinked through the chelated metal. This can occur with separate chelation moieties of two or more polymers chelating the same metal.

In some embodiments, the non-degradable PVA-DHBA and PAA-DHBA polymers can be administered orally to treat, inhibit, or prevent iron overload. As such, the polymeric chelators can be included in oral therapeutics for use in iron overload disease patients. The chelating polymers can selectively bind iron and remove it from the GI tract before it is being absorbed into the blood stream. Chelating polymers can be deposited in tissues or administered systemically for iron chelation.

The polymeric chelators may be used as metal chelators to remove metals from a wide range of substance and can have applications in a wide range of diverse fields. Polycations have been employed in industrial applications such as water treatment and ion exchange resins (for separation-purification purposes). The high affinity and selectivity for iron provides important features for the application of these gels.

The polymeric chelators can be highly effective metal (e.g., iron) chelators that selectively bind metals in the GI tract and prevent the metal from being absorbed into the blood stream. The chelated metal can be passed from the GI tract as waste.

In some embodiments, the present disclosure provides a siderophore mimetic gel polymer therapeutic that either may be injected or ingested. In some embodiments, dosage form design may aid patient compliance. The gel format may retain chelators in the gastrointestinal tract to enable self-dosing of the compound as necessary and to mitigate systemic side effects that plague current iron chelators. The injectable siderophore-mimetic polypeptide may improve safety compared to DFO and the polymer molecular weight may be optimized to extend circulation half-life.

In one embodiment, the polymeric chelator can be configured to include a polymer or monomer that is soluble in water. The composition can be configured to be injected and to be relatively non-toxic or have reduced toxicity. In one embodiment, the polymeric chelator can be configured to have an appropriate molecular weight for injection. In another embodiment, the polymeric chelator can be configured to have an appropriate molecular weight for ingestion. Also, the composition having a polymeric chelator can be configured for inhalation or for topical application.

In one embodiment, a polymeric chelator can be ingested and can block metal absorption by chelating the metal. The composition can include a cross-linked polymer configured for ingestion. Some embodiments can be ingested and be configured to be absorbed from the intestine such that the chelator can chelate metals that have already been absorbed into the body.

In some embodiments, the polymeric chelator disclosed herein may more accurately mimic the Enterobactin side chain shown. Polymeric chelators that mimic the structure of siderophore may be considered as a desirable parenterally administered iron chelator. The plasma half-life of these polymeric agents can be optimized based on the initial molecular weight of the polymer. Moreover, the toxic side effect of these polymeric chelators may be significantly reduced because they consist of polypeptide units. Polymeric forms of siderophore mimetics offer several therapeutic advantages. These compounds can disable bacterial recruitment of iron. Also, polymeric chelators can localize the compounds to the GI tract (oral gel material) and/or extend the circulation half-life by increasing molecular weight (injected material).

Figure 2:
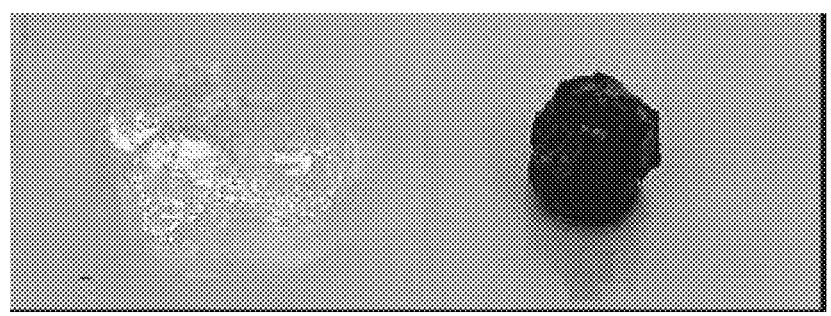
FIG. 2 is a picture of an iron chelating gel of the present invention before and after exposure to iron.
Figure 8:
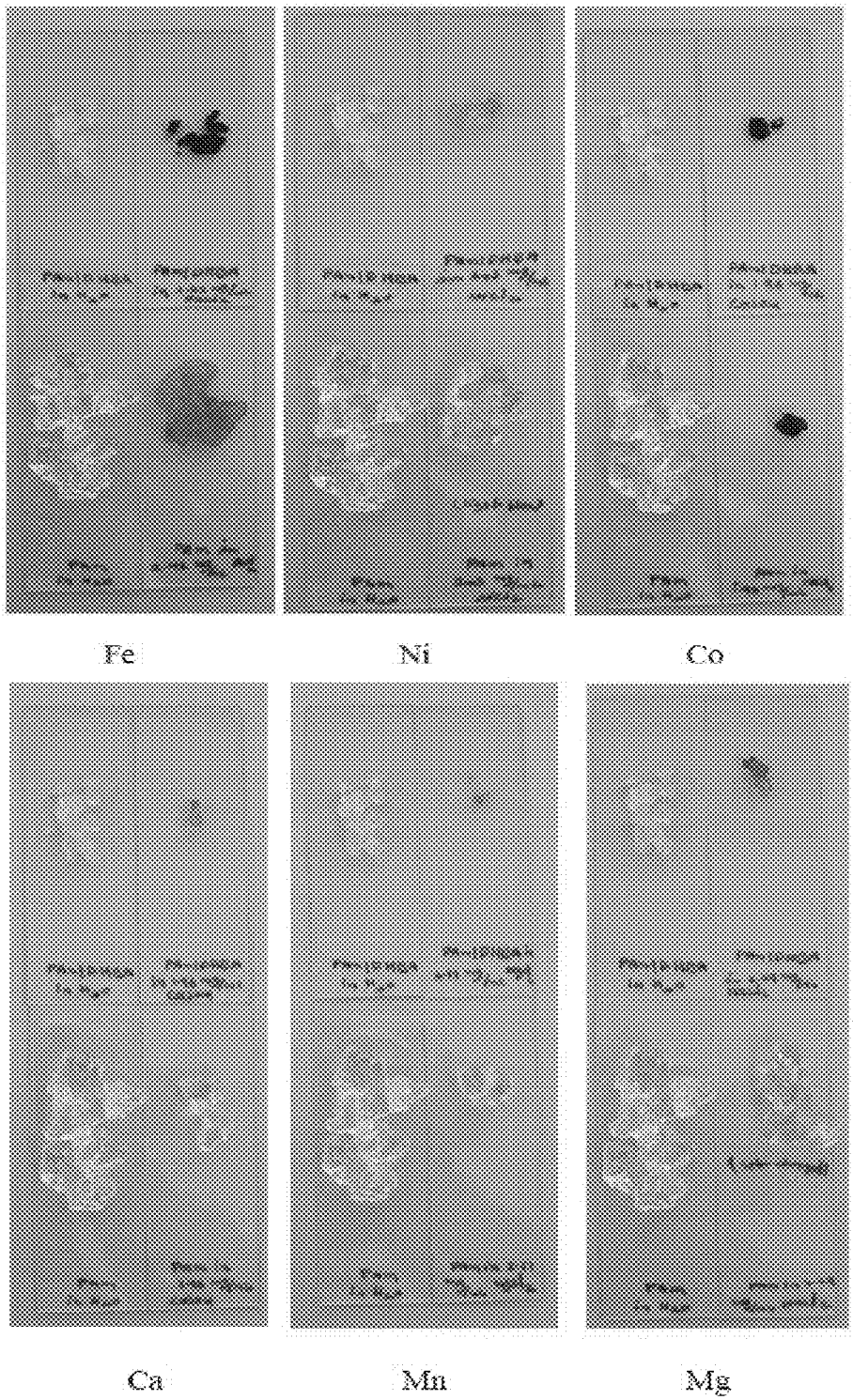
FIG. 8 are photographs of hydrogels.
Figure 9:
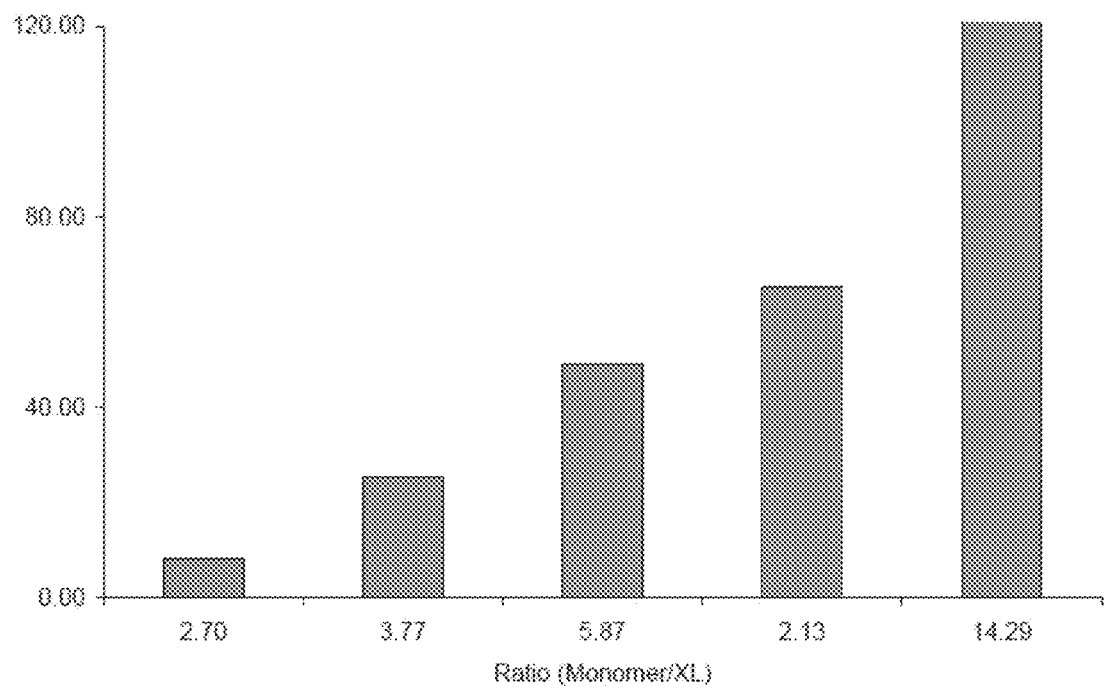
FIG. 9 is a chart depicting swelling properties of a polymer.
Figure 10:
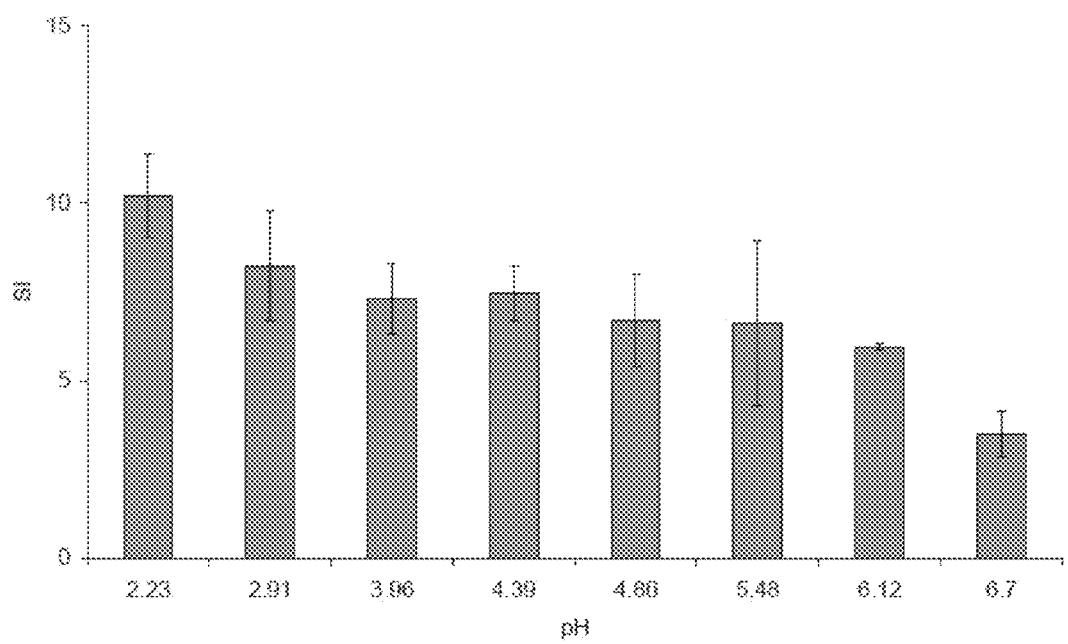
FIG. 10 is a chart depicting swelling properties of a polymer.
Figure 11:
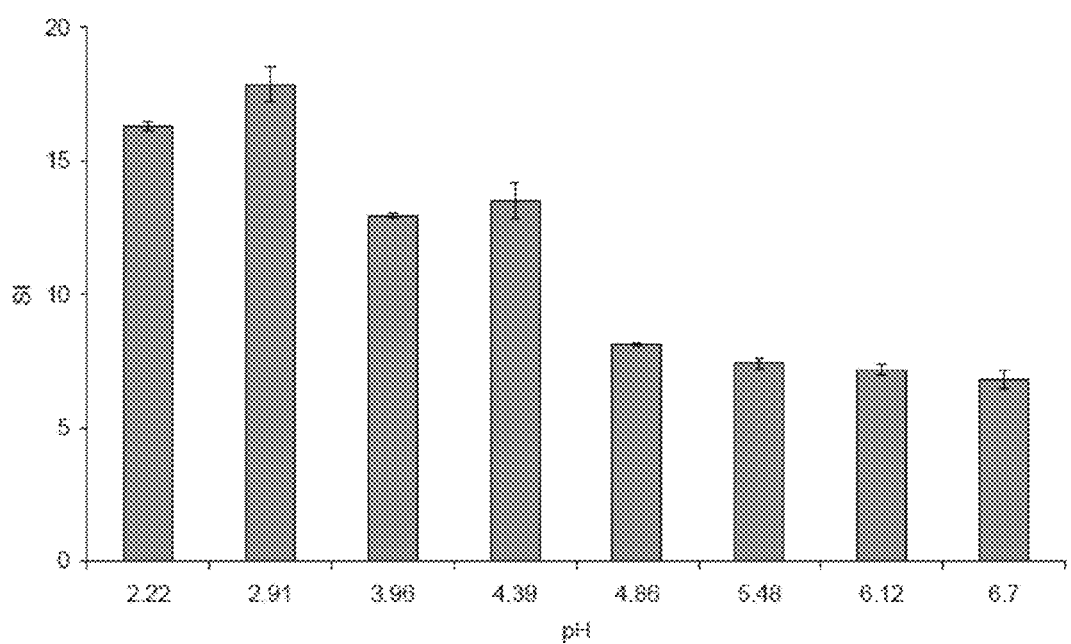
FIG. 11 is a chart depicting swelling properties of a polymer.
Figure 12:
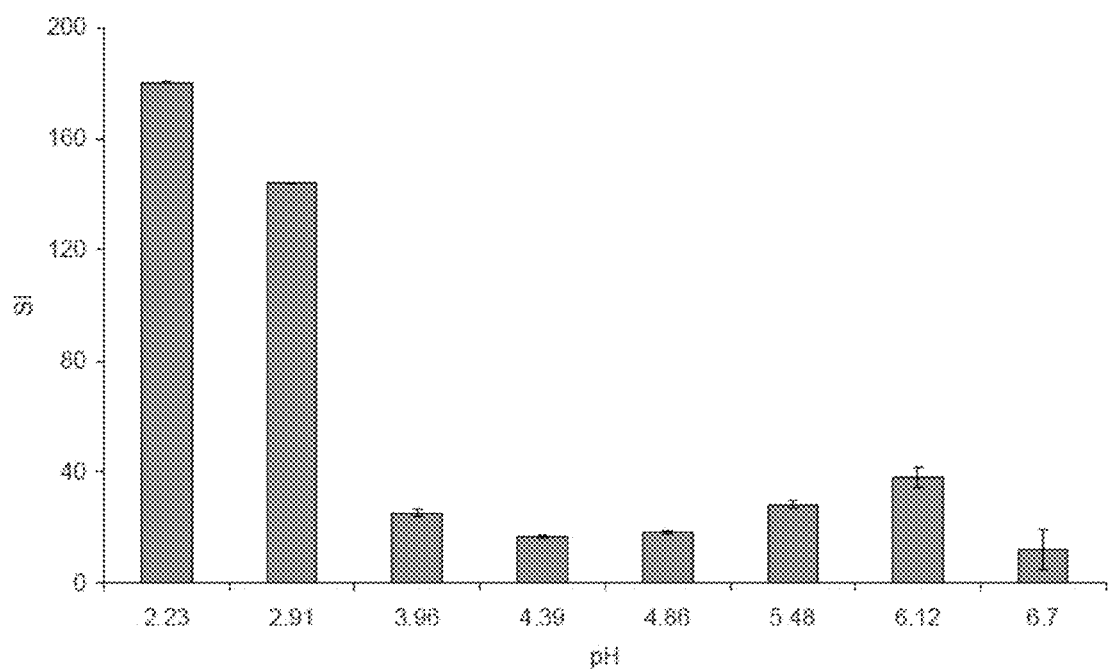
FIG. 12 is a chart depicting swelling properties of a polymer.
Figure 13:
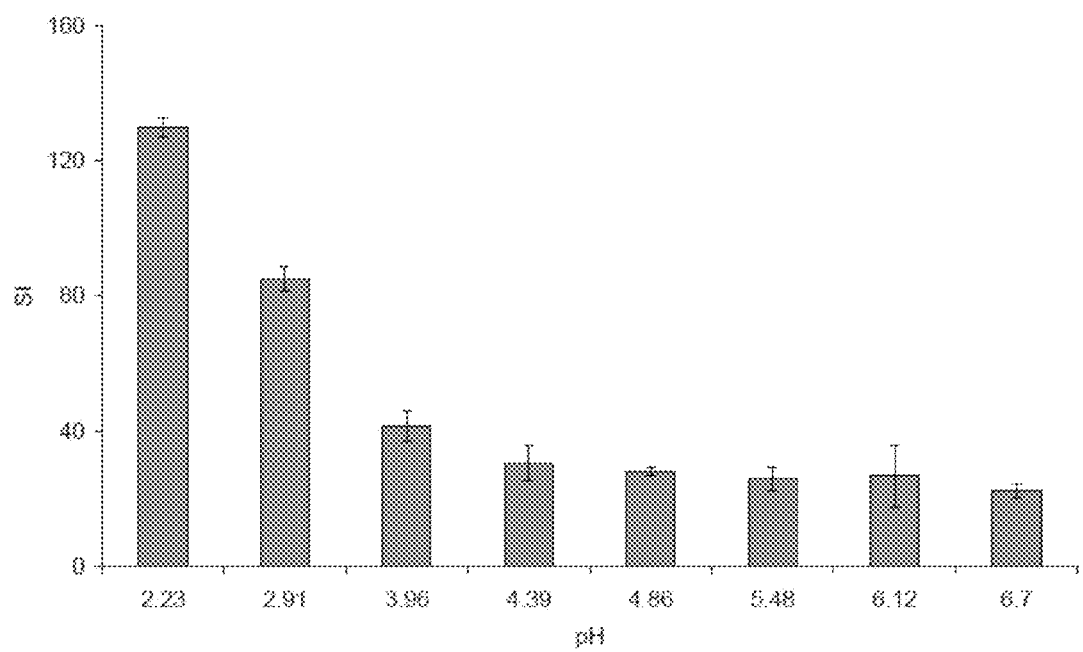
FIG. 13 is a chart depicting swelling properties of a polymer.
Figure 14:
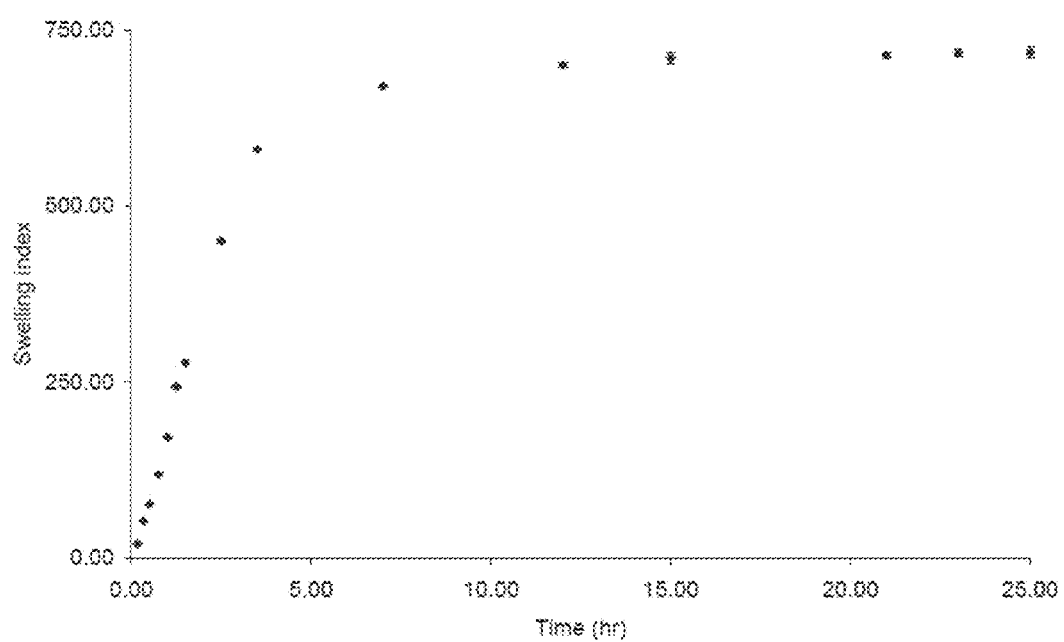
FIG. 14 is a chart depicting swelling properties of a polymer.
Figure 15:
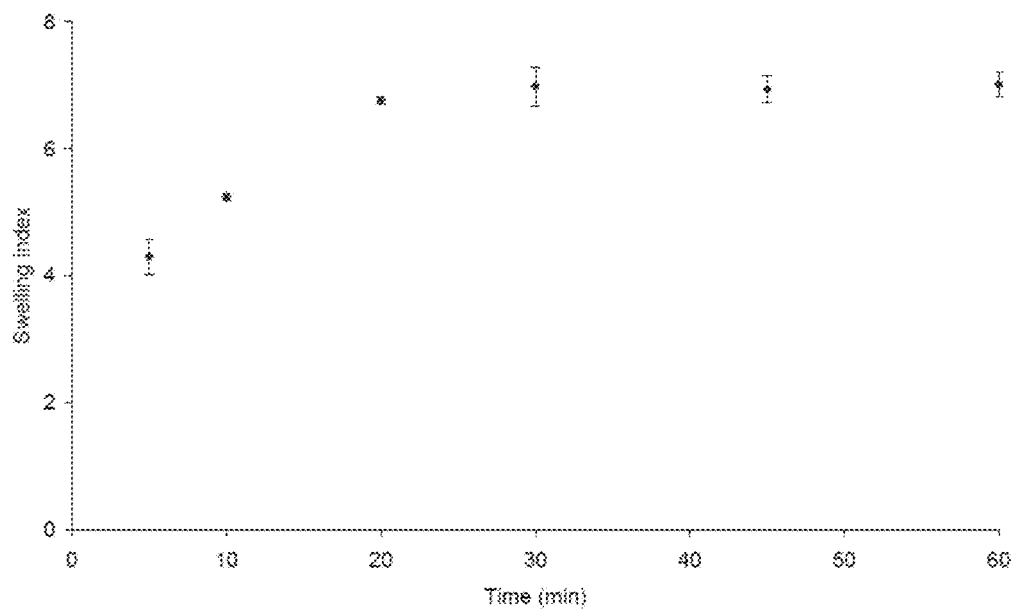
FIG. 15 is a chart depicting swelling properties of a polymer.
Figure 16:
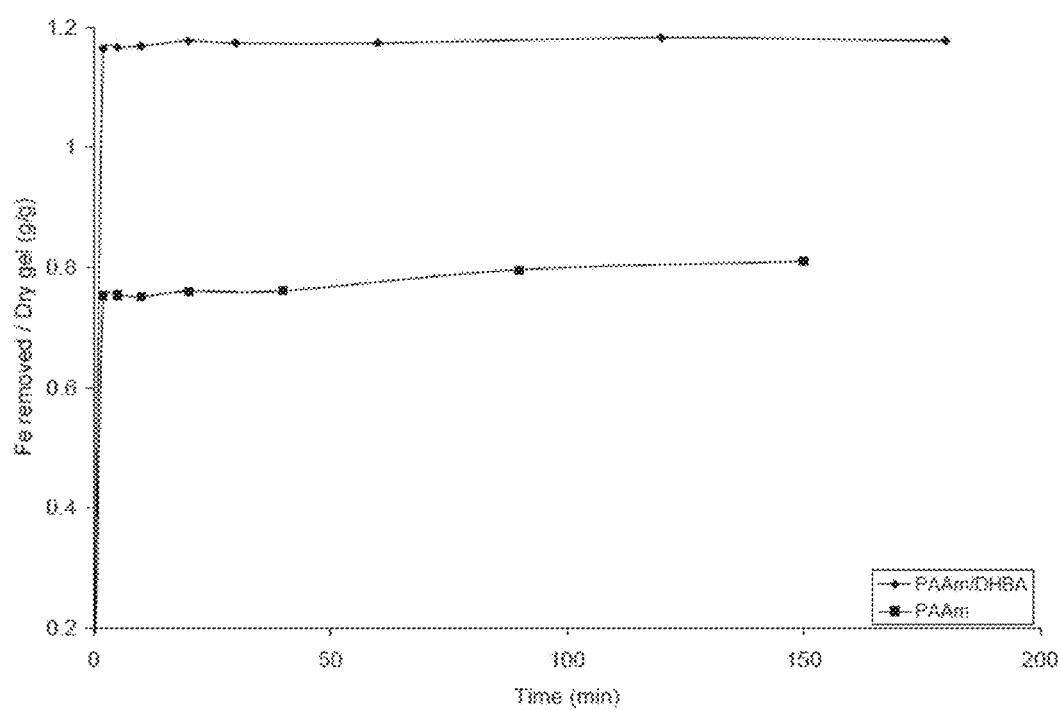
FIG. 16 is a chart depicting swelling properties of a polymer.

In certain embodiments, the crosslinked forms of siderophore mimetic polymers will not be absorbed when orally given. These materials may demonstrate rapid iron binding with high affinity and selectivity. FIG. 2 depicts an iron chelating gel of the present invention before and after exposure to iron. In some embodiments, the pM values for iron binding the materials disclosed herein are estimated to be at least ten times higher than any of the existing therapeutic chelators. The design of these polymers can mitigate the systemic side effects and toxicity of current drugs. Siderophore mimetic polymers are anticipated to selectively and effectively bind iron in the GI tract if administered orally or from the bloodstream if administered parenterally. Several polymers have been synthesized with side chains that mimic the iron binding domain of siderophores. The orally administered Siderophore Mimetic Gel (SiMiG-01) and the injectable Siderophore Mimetic Polymer (SiMiP-01) exhibit binding coefficients at least ten times higher than existing therapeutics.

In one embodiment, the polymeric chelators can be incorporated into textiles, fabrics, absorbent members, gauze, wipes, bandages, or the like. Further applications of the polymeric chelators can be used for metal chelation in a wide range of consumer products and processes. An example of one process that the polymeric chelator can be useful is in oil well treatments, such as those treatments for descaling or inhibiting the formation of scales.

To facilitate a better understanding of the present invention, the following examples of specific embodiments are given. In no way should the following examples be read to limit or define the entire scope of the invention.

EXAMPLES

Example 1

A non-absorbable polymer hydrogel was prepared. Briefly, conjugation of DHBA to PVA and PAA was achieved through formation of amide bonds. Both PVAm and PAAm are polycation hydrogels that have reactive primary amine side groups that can be coupled to 2,3 DHBA. 2,3 DHBA acid is a fraction of the well known natural iron chelator Enterobactin (Log K=52) which is a high affinity siderophore that acquires iron for microbial systems. Cross-linked PVAm hydrogel was synthesized by hydrolyzing a precursor polymer, PNVF, in a basic medium. Cross-linked PAAm hydrogel was synthesized by cross-linking the precursor PAAm chains.

The PVA-DHBA and PAA-DHBA polymers exhibited high iron binding affinity and iron selectivity. Both PVA-DHBA (i.e., PVAm_DHBA) and PAA-DABA (i.e., PAAm_DHBA) demonstrated an almost instant iron absorbance when equilibrated in ferric solution. Both chelating polymers were hydrogels that demonstrated a high affinity and selectivity for iron at pHs similar to the GI tract and the time required for equilibration of swelling response of the polymer to gel varied in different pHs, as shown in FIGS. 3-34.

Example 2

Immobilization of 2,3 dihydroxybenzoic acid, a portion of the metal chelating domain of Enterobactin, on organic polymers was found to be an effective method to mimic the structure of this naturally occurring siderophore. The effect of cross-linker concentration in hydrogel characterization and the yield of the reaction were studied. Table 1 below shows the results of these studies.

TABLE 1

| Reaction conditions and swelling behavior of hydrogel at pH = 6. | | | |
|---|---|---|---|
| PAAm (mg) | Cross-linker (mg) | Swelling index | Yield (%) |
| 123.6 | 21.2 | 8.0 | 79.6 |
| 124.3 | 33.9 | 7.1 | 75.7 |
| 126.4 | 45.8 | 5.0 | 76.8 |
| 124.9 | 58.9 | 4.6 | 68.0 |

Over this cross-linker concentration range, the swelling behavior of the final hydrogel is appropriate for application as an oral therapeutic, as shown in FIG. 35A. The material is expected to swell no more than 20 fold after exposure to GI fluids. Moreover, acidic pH values showed a higher swelling index, as shown in FIG. 35B. Complete swelling occurred over about 20 minutes regardless of the pH value studies, as shown in FIG. 35C. These studies were not conducted for siderophore mimetic polypeptides, which are completely soluble.

Several different concentrations of the chelating moiety may be conjugated to the soluble (polypeptide) and insoluble (crosslinked hydrogel) polymers to optimize the selectivity and affinity for iron. Briefly, dihydroxybenzoic acid (DHBA) may be reacted to polyvinyl amine (PVAAm) or polyallylamine (PAAm) or poly-L-lysine (PLL; for water soluble polymer injections). These reactions may produce structure similar to Enterobactin, as shown in FIG. 1A. HPLC may be used to determine the concentration of the conjugated moiety as a means to calculate the exact number of iron coordination sides. In this manner, a variety of well-defined polymers may be synthesized for oral administration or injection.

Both orally and parenterally administered iron chelator agents must have high selectivity and affinity for iron. Moreover, parenterally administered iron chelator agents should be non-toxic with a relatively long plasma half-life.

The iron binding affinity of siderophore mimetic gels was at least ten times greater than any of the current therapeutics. In addition, a multi-solute system was used to evaluate the metal selectivity of siderophore mimetic gels at different pHs. At an equal concentration of all metals (2 mg/mL), siderophore mimetic polymer gels (i.e. modified with DHBA) absorbed almost 80% of the iron in the media, the highest of any metal present, as shown in FIGS. 36A-D. Siderophore mimetic polymers were highly selective for iron and nickel over essential elements zinc and calcium, as desired. The ratio was similar across a wide range of pHs. Much less selectivity was observed for polyamines (PVAAm and PAAm), which also tended to absorb zinc and calcium.

The kinetics of metal binding was also monitored in a 2 mg/mL $FeCl_3$ solution. The equilibrium binding was found to be 1180 mg/g for iron chelating gel, as shown in FIG. 37. More importantly, about 80% of total absorption was attained in <5 min. This near instantaneous iron absorption behavior may be highly desired for treatment of acute iron overload.

The rate constant and binding capacity of this polymer gel was derived by curve fitting the kinetic data, as shown below in Table 2.

TABLE 2

Kinetic parameters for ferric binding by PAAm/DHBA at pH = 2.

| Kinetic model | Rate constant | Ion | $R^2$ |
|---|---|---|---|
| Pseudo-first order | 0.24 | ferric | 0.9988 |
| Pseudo-second order | 0.23 | ferric | 1 |

The iron binding capacity was determined at different pH values and different isotherm models were used to fit the data. At low pH, the metal ion uptake was relatively high. Increasing the pH lowered the values of the metal ion uptake, as expected. The respective isotherm curves of ferric and ferrous solutions were obtained at different pH values and fit using well known models of solute absorption; Freundlich, Langmuir or Temkin, as shown below in Table 3.

TABLE 3

Isotherm parameters for ferric and ferrous binding by siderophore mimetic gels.

| | pH | | | | | |
|---|---|---|---|---|---|---|
| | 2-3 | 5-6 | 7.4 | 2-3 | 5-6 | 7.4 |
| Isotherm model | Ferric | | | Ferrous | | |
| Freundlich | | | | | | |
| $K_F$ | 775.53 | 3454.62 | N/A | 3133.29 | 2229.46 | 4384.30 |
| n | 3.68 | 1.51 | N/A | 2.77 | 1.58 | 2.15 |
| $R^2$ | 0.99 | 0.99 | N/A | 0.99 | 0.89 | 0.99 |
| Langmuir | | | | | | |
| $q_{max}$ | 526.31 | 1428.50 | N/A | 2000.00 | 2500.00 | 1428.50 |
| $K_L$ | 63.33 | 17.50 | N/A | 25.00 | 2.00 | 87.50 |
| $R^2$ | 0.99 | 0.84 | N/A | 0.96 | 0.82 | 0.95 |
| Temkin | | | | | | |
| A | 331.67 | 1.00 | N/A | 199.29 | 19.20 | 635.73 |
| b | 21.06 | 6.19 | N/A | 5.13 | 4.08 | 7.77 |
| $R^2$ | 0.96 | 1.00 | N/A | 0.96 | 0.94 | 0.96 |

These data are tremendously useful for making quantitative comparisons between the polymeric chelators and currently approved chelators.

The stability constant or 'binding coefficient' of gel chelators may be measured using an historic ligand competition assay. Competitive chelation of iron by polymeric chelators in equilibrium with a water-soluble chelator (ethylenediaminetetraacetic acid: EDTA) may be used to determine the stability constant of iron-ligand complexes of the polymers. Briefly, to a 1.5 ml of 10 mM EDTA solution may be added 2 mL of 5 mM of $FeCl_3$ solution and 21.5 mL PBS and a known mass of gel. The mixture may be rotated at 20° C. for 3 days and the concentration of the soluble iron complex may be determined by inductively coupled plasma mass spectroscopy (ICP-MS). The stability constant of the gel may be determined following the procedure reported in literature. Stability constants may also be determined by means of potentiometric titration to confirm results.

High throughput cell viability assays may be completed using standard procedures. Cytotoxicity of polymers may be determined by the CellTiter 96® Aqueous Cell Proliferation Assay (Promega). HUVEC cells may be cultured and incubated with polymers for ~24 h. The media may then be removed and replaced with a mixture of 100 µL fresh culture media and 20 µL MTS reagent solution. The cells may be incubated for 3 hours at 37° C. in a 5% $CO_2$ incubator. The absorbance of each well may then be measured at 490 nm using a microtiter plate reader (SpectraMax, M25, Molecular Devices Corp.) to determine relative cell viability. A similar study may be conducted on polymer gels for oral delivery using Caco-2 cells (colon epithelium).

Female Sprague-Dawley rats, ~6 weeks old may be used to assess treatment effects on iron load. The initial iron level in the blood of rats may be measured before starting the experiment after animals have equilibrated to diet and environment at KU. Rats may be divided into ten groups of eight animals, as shown in Table 4, and some may be treated with iron nitrate (150 ppm of iron in drinking water).

TABLE 4

Iron chelation therapy treatment and control roups.

| Iron exposure in water | Treatment (n = 8) |
|---|---|
| None | None (negative control) |
| None | SiMiG-01 (oral polymer gel) |
| None | SiMiP-01 (injected polypeptide) |
| 150 ppm | None (positive control) |
| 150 ppm | Deferasirox (40 mg/kg daily; oral) |
| 150 ppm | Deferoxamine (25 mg/kg; S.C injection) |
| 150 ppm | SiMiG-01 (40 mg/kg daily; oral) |
| 150 ppm | SiMiP-01 (25 mg/kg; S.C injection) |
| 150 ppm | SiMiG-02 (40 mg/kg daily; oral) |
| 150 ppm | SiMiP-02 (25 mg/kg; S.C injection) |

The animals may be fed 25 mg/kg of the gel-containing diet for 4 days, which may provide adequate time to allow clearance of untreated intestinal contents. Urine, fecal, and blood samples may then be collected from each animal on days 5 and 10. Animals receiving the injected chelators Deferoxamine (DFO), SiMiP-01 or SiMiP-02 may be treated with subcutaneous injections of 40 mg/kg every 2 days during a 10 day period (e.g. injections on day 2, 4, 6, etc). High molecular weight polymer (>25 kDa) may not be well absorbed; therefore, tail vein injections may be used in lieu of subcutaneous injections if larger polymers are identified as better iron chelators. The iron level in the blood, feces, and urine may be measured using ICP-MS. Animals may be continually monitored for distress and blood samples from animals receiving injected chelators may be analyzed for aspartate aminotransferase, alanine transamidase, total bilirubin, alkaline phosphatase and/or urea nitrogen and serum creatinine to monitor liver and kidney function, respectively. The experimental protocol may involve healthy animals and moderate doses of iron; therefore, animal health is not expected to be compromised. SiMiG-03 and SiMiP-03 may also be tested if another suitable polymer is identified.

Example 3

Materials

Poly(allylamine hydrochloride) (PAAm) with an average molecular weight of 56 kDa and analytical grade reagent N,N'-methylenebisacrylamide (MBA) were obtained from Sigma-Aldrich and used without further modification. 2,3 dihydroxybenzoic acid, N,N,N-triethylamine (TEA), dimethylformamide (DMF), and all metal chlorides were purchased from Fisher Scientific and used as received. Dicyclohexylcarbodiimide (DCC) and N-hydroxysuccinimide (NHS) were purchased from Thermo Scientific and used without further modification. Deionized water (DI) was obtained from a Barnstead EasyPure water purifier.

Preparation of PAAm Hydrogel.

Briefly, a 20% w/v polymer solution containing a predetermined amount of MBA was prepared. The cross-linker was dissolved in deionized water (flushed with nitrogen for 5 min) and then added to the polyallylamine polymer. TEA, the cross-linking catalyst (300 µL), was then added to the solutions and mixed thoroughly. Next, the precursors were transferred by micropipet into a small plastic cuvette and subsequently covered with parafilm. The cuvettes were held at ambient temperature for 1 hour and then cooled to ca. 3° C. and held there for an additional 24 hours. After this time, hydrogels were removed from the cuvettes and washed with 0.05 M sodium chloride for several days.

2,3 Dihydroxybenzoic Acid Modification of Hydrogel.

A solution of 2,3 DHBA and NHS in 5 mL of DMF was mixed with a solution of DCC in 5 mL of DMF. The mixture was stirred at low temperature for 6 hours to give a white precipitate. The precipitate was filtered, and the filtrate was added directly to a dry gel with known weight. Several ratios of PAAm:DHBA (0.001, 0.005, 0.05, 0.01) were investigated in this study to optimize the selectivity and iron binding affinity of the final hydrogel, as shown below in Table 5.

TABLE 5

| Molar ratio | % conjugation | Log K |
|---|---|---|
| 0.001 | 95 | 27.04 |
| 0.005 | 73 | 27.01 |
| 0.05 | 83 | 26.6 |
| 0.01 | 69 | 26.4 |

The reaction mixture was held at room temperature for 3 days. PAAm conjugate hydrogel was then washed with water for several days.

Quantification of Amine Functional Groups.

Primary amine groups were quantified by potentiometric titration. After grinding to a powder, 40 mg of PAAm and each PAAm-DHBA hydrogel were suspended in 35 mL of 0.2 M aqueous KCl solution. Next, 140 µL of 8 M KOH aqueous solution was added to polymer suspensions to raise the pH to ~12. Standard 0.1 M HCl was used to titrate the suspension. HCl was added until the pH was about 2.5 in both polymer suspensions. Free amine groups were quantified from potentiometric data following reported procedures.

Polymer-Iron Stability Constant Determination.

The stability constant of gel chelators was measured using an historic ligand competition assay. The competitive chelation of iron by polymeric chelator in equilibrium with a water-soluble chelator (ethylenediaminetetraacetic acid: EDTA) was used to determine the stability constant of iron-ligand complexes of PLL/DHBA hydrogel. Briefly, to a 1.5 ml of 10 mM EDTA solution was added 2 mL of 5 mM of $FeCl_3$ solution and 21.5 mL PBS and a known mass of gel. The mixture rotated at 20° C. for 3 days and the concentration of the soluble iron complex was determined by inductively coupled plasma mass spectroscopy (ICP-MS). The stability constant of the gel was determined following the procedure reported in literature. The same procedure was repeated for all the different PAAm:DHBA ratios.

Selectivity Study.

The selectivity for Fe by PAAm-DHBA in the presence of several heavy metals such as copper, zinc, manganese, calcium, and potassium was studied. Metal solution (10 mL) containing all metal components was prepared. The upper tolerable intake level of each metal was used as an initial concentration in the solution. These concentrations were chosen on the basis of the U.S. recommended daily allowance (RDA) data on the daily dietary uptake of these metal ions present in a normal meal. The solution mixture was then adjusted to pH 2.5 and held at room temperature for 2 hours after adding a known mass of PAAm-DHBA dry gel. The selectivity study was carried out for all different PAAm-DHBA ratios.

Metal Analysis.

Mono- and multi-elemental analysis of samples was quantified by Inductively Coupled Plasma Optical Emission Spectrometry (ICP-OES) (Optima 2000 DV, PerkinElmer, USA) fitted with an AS 93plus autosampler (PerkinElmer, USA). A Cross-Flow nebulizer and a Scott spray chamber were used. The RF Power was 1300 W and nebulizer and auxiliary flows were 0.8 and 0.2 L/min, respectively. Sample flow was set at 1.5 mL/min. ICP-OES data was processed using Winlab 32 (Ver. 3.0, PerkinElmer, USA). The analytical curves used for sample analysis had coefficients of correlation >0.999.

Results and Discussion

Synthesis and Characterization of PAAm-DHBA Hydrogels.

Poly(allylamine hydrochloride) was cross-linked with N,N-methylenebisacrylamide (MBA) by a Michael-type addition reaction. The ratio of monomer to cross-linker was selected based on recommendations from the literature. The DCC/NHS coupling chemistry was adopted to react the free amine side chains of the hydrogel with the carboxylic end of the 2,3 DHBA. Since the concentration of 2,3 DHBA hydroxyl groups may be critical for enhanced binding of iron, the choice of appropriate PAAm:DHBA ratio was important for obtaining hydrogels with high iron affinity. To optimize the binding affinity and selectivity of the final product, several ratios of PAAm:DHBA were investigated, as shown in Table 5. Potentiometric titration data were used to calculate the degree of conjugation. The conjugation efficiency varied from 75%-95% depending on the initial concentration of 2,3 DHBA.

Conditional Stability Constant of Fe(III)-Hydrogel.

The ligand competition method is widely used for the determination of stability constants of both soluble iron(III)-ligand complexes and cross-linked polymeric chelators. The stability constants (log K) of PAAm-DHBA-iron complexes were considerably higher (×10) than of those similarly synthesized hydrogels, as shown in Table 5 A decrease in the concentration of DHBA resulted in a decrease of the conditional stability constant. As the concentration of functional groups incorporated in hydrogels decreased, the binding capacity of the hydrogel decreased as well, as shown in FIGS. 38 and 39. Chelating properties of a polymeric chelator have also been shown to be affected by steric hindrance between the ligand and the polymeric matrix, but in the case of PAAm-DHBA hydrogels there may be little inference by the polymer backbone in the iron chelation process based on the binding capacities observed.

It has been reported the synthesis of a range of iron binding dendrimers terminated with hexadentate ligands formed from hydroxypyridinone, hydroxypyranone, and catechol moieties. The stability constant of these dendrimers were similar to those reported in this study. In another study, a series of polymeric iron chelators have been introduced by the synthesis of 3-hydroxypyridin-4-1 hexadentate ligand incorporated into polymers via co-polymerization with N,N dimethylacrylamide, and N,N'-ethylene-bis-acrylamide. The Fe(III) chelation capacity of this polymer reached 80% within 1 h, and the stability constant (log K') for iron(III) was determined to be 26.55, slightly lower than reported here.

Selectivity of the PAAm-DHBA Hydrogels.

Since PAAm-DHBA hydrogels possessed a high affinity for Fe(III), it was anticipated that these hydrogels may also possess an improved selectivity for Fe(III) over other metal ions. Copper(II), zinc(II), and manganese(II) are all present in biological tissues and in food. As these three metals are essential for life, it is important that the hydrogels designed in this study possess much lower affinities for this group of divalent cations. In competition studies, iron(III) was shown to be selectively bound to the hydrogels in the presence of competing metals, i.e. Zn2+, Mn2+, and Cu2+, as shown below in Table 6.

TABLE 6

| | % absorbed/mg of dry gel | | | |
|---|---|---|---|---|
| Gel MR* | Zn | Fe | Mn | Cu |
| 0.001 | 3.65 | 11.04 | 4.09 | 0.00 |
| 0.005 | 0.38 | 7.05 | 0.45 | 0.65 |
| 0.05 | 0.27 | 1.59 | 0.50 | 1.74 |
| 0.01 | 0.90 | 1.35 | 0.45 | 0.63 |
| 0 | 1.63 | 2.33 | 2.11 | 1.64 |

*Theoretical molar ratio of DHBA to amine sites.

In all these cases, iron concentrations were decreased significantly after incubation with hydrogel, whereas the concentrations of the competing bivalent metals remained almost unchanged. In comparison, it has been reported a Fe(III) hydrogel chelator composed of a relatively high stability constant; however, the selectivity studies revealed that the binding capacity for both Fe(III) and Cu(II) were almost identical, indicating the lack of selectivity toward Fe(III).

Example 4

Materials.

Poly(allylamine hydrochloride) (PAAm) with an average molecular weight of 56 kDa and analytical grade reagent N,N'-methylenebisacrylamide (MBA) were obtained from Sigma-Aldrich and used without further modification. 2,3 dihydroxybenzoic acid, N,N,N-triethylamine, dimethylformamide (DMF), citric acid, potassium phosphate and all metal chlorides were purchased from Fisher Scientific and used as received. Dicyclohexylcarbodiimide (DCC) and N-hydroxysuccinimide (NHS) were purchased from Thermo Scientific and used without further modification. Deionized water (DI) was obtained from a Barnstead EasyPure water purifier.

Preparation of PAAm Hydrogel.

PAAm was cross-linked with MBA by a Michael-type addition reaction. This cross-linking procedure was developed to synthesize PAAm and poly(α-L-lysine hydrobromide) hydrogels. Briefly, a 20% w/v polymer solution containing a predetermined amount of MBA was prepared. The cross-linker was dissolved in deionized water (flushed with nitrogen for 5 minutes) and then added to the polyallylamine polymer. Several different molar ratios of cross-linking agent to PAAm were investigated. TEA, the cross-linking catalyst (300 μL), was then added to the solutions and mixed thoroughly. Next, the precursors were transferred by micropipet into small plastic cuvettes and subsequently covered with parafilm. The cuvettes were held at ambient temperature for 1 hour and then cooled to ca. 3° C. and held there for an additional 24 hours. After this time, hydrogels were removed from the cuvettes and washed with 0.05 M sodium chloride for several days. Multiple synthesis conditions were employed to prepare the hydrogel investigated in this study, as shown below in (Table 7).

TABLE 7

Reaction conditions and swelling behavior of hydrogel at pH = 6.

| PAAm (mg) | Cross-linker (mg) | A/B* | Swelling index** | Yield (%) |
|---|---|---|---|---|
| 123.6 | 21.2 | 0.1 | 8.0 | 79.6 |
| 124.3 | 33.9 | 0.2 | 7.1 | 75.7 |
| 126.4 | 45.8 | 0.3 | 5.0 | 76.8 |
| 124.9 | 58.9 | 0.4 | 4.6 | 68.0 |

*mole ratio of crosslinker double bonds to polymer amines.
**swelling index of PAAm/DHBA hydrogel.

Synthesis at various crosslinker:polymer ratios facilitated identification of an acceptable range of swelling indices for biomedical applications while maintaining an acceptable reaction yield. These values are known to provide sufficient mechanical integrity and chemical stability after oral administration, based upon research reports and on data for the FDA-approved product, Renagel®.

Swelling Studies.

The swelling behavior of hydrogels was studied using buffered solutions (sodium hydroxide as a buffering agent) with fixed ionic strength (0.5 M). A historic protocol was used for making buffer solution with a known ionic strength. Dried samples with known weights were placed in a solution of defined pH at room temperature. Samples were taken from the solution after reaching equilibrium. The swelling indexes (SI) were calculated using the following equation:

$$SI = \frac{w_s - w_d}{w_d}$$

where $W_s$ is the weight of the swollen hydrogel at an equilibrium state, and $W_d$ is the weight of the dried hydrogel.

2,3 Dihydroxybenzoic Acid Modification of Hydrogel.

A solution of 2,3 DHBA (100 mg, 0.65 mmol) and NHS (74 mg, 0.65 mmol) in 5 mL of DMF was mixed with a solution of DCC (67 mg, 0.325 mmol) in 5 mL of DMF. The mixture was stirred at low temperature for 6 hours to give a white precipitate. The precipitate was filtered, and the filtrate was added directly to a dry gel with known weight (25 mg). The reaction mixture was held at room temperature for 3 days. PAAm conjugate hydrogel was then washed with water for several days Quantification of Amine Functional Groups.

Primary amine groups were quantified by potentiometric titration. After grinding to a powder, 40 mg of PAAm and PAAm/DHBA polymer were suspended in 35 mL of 0.2 M aqueous KCl solution. Next, 140 μL of 8 M KOH aqueous solution was added to polymer suspensions to raise the pH to ~12. Standard 0.1 M HCl was used to titrate the suspension. HCl was added until the pH was about 2.5 in both polymer suspensions. Free amine groups were quantified from potentiometric data Binding Kinetics Study.

Ferric chloride solution (2 mg/mL) was adjusted to pH 6.5 using NaOH while purging with $N_2$. The solution was kept at room temperature for kinetic studies. Samples were taken from the media at different time intervals to determine the rate of iron binding by PAAm/DHBA.

Binding Experiments.

Known concentrations of ferric chloride and ferrous chloride solutions (0.25, 0.5, 1, 2, 2.5) mg/mL were prepared. Binding experiments were carried out by taking 20 mL of metal solutions in 125 mL volumetric flasks, solutions were adjusted to the desired pH while maintaining iron concentration. Next, a known mass of PAAm/DHBA hydrogel was added to the mixture and was held at room temperature for 2 hours or until equilibrium was reached. The solutions were then filtered and the filtrates were analyzed for metal concentration.

Selectivity Study.

The selectivity for Fe by PAAm/DHBA in the presence of several heavy metals such as copper, zinc, manganese, calcium, and potassium was studied. Metal solutions (10 mL) containing a 1:1 (wt) mixture of iron and heavy metals were prepared (2 mg/mL). The solution mixtures were then adjusted to pH 2.5, 4, 5, and 7 and held at room temperature for 2 hours after adding a known mass of PAAm/DHBA dry gel.

Metal Analysis.

Mono- and multi-elemental analysis of samples was quantified by Inductively Coupled Plasma Optical Emission Spectrometry (ICP-OES) (Optima 2000 DV, PerkinElmer, USA) fitted with an AS 93plus autosampler (PerkinElmer, USA). A Cross-Flow nebulizer and a Scott spray chamber were used. The RF Power was 1300 W and nebulizer and auxiliary flows were 0.8 and 0.2 L/min, respectively. Sample flow was set at 1.5 mL/min. ICP-OES data was processed using Winlab 32 (Ver. 3.0, PerkinElmer, USA). The analytical curves used for samples analysis had coefficients of correlation >0.999.

Adsorption Isotherms.

Different isotherm models were employed to determine how the metal molecules distributed between the liquid phase and the solid hydrogel phase when the adsorption process reached equilibrium state. Langmuir, Freundlich, and Temkin isotherm models were applied to the data. Adsorption parameters of ferric and ferrous ions were calculated at different pHs. The accuracy of the isotherm models was evaluated by linear correlation coefficient ($R^2$) values.

Langmuir Isotherm.

Langmuir isotherms assume monolayer adsorption onto a surface containing a finite number of adsorption sites. The linear form of the Langmuir isotherm equation is given as:

$$\frac{C_e}{q_e} = \frac{1}{q_{max} K_L} + \frac{C_e}{q_{max}}$$

where $C_e$ is the equilibrium concentration of the metal ion (mg/L), $q_e$ is the amount of metal ion adsorbed per unit mass of hydrogel (mg/g), $K_L$ and $q_{max}$ are Langmuir constants related to the adsorption/desorption energy and adsorption capacity, respectively. When $C_e/q_e$ was plotted against $C_e$, a straight line with slope of $1/q_{max}$ was obtained. The $R^2$ values are summarized in Table 8. The Langmuir constants $K_L$, and $q_{max}$ were calculated from Eq. (2) and their values are shown in Table 8.

TABLE 8

Isotherm parameters for ferric and ferrous binding by PAAm/DHBA. Gels were equilibrated in 2 mg/mL iron solutions.

| | pH | | | | | |
|---|---|---|---|---|---|---|
| | 2.2 | 5.4 | 7.4 | 2.2 | 5.4 | 7.4 |
| Isotherm model | Ferric | | | Ferrous | | |
| Freundlich | | | | | | |
| $K_F$ | $77.53*10^{+1}$ | $34.55*10^{+2}$ | | $31.33*10^{+2}$ | $22.29*10^{+2}$ | $43.84*10^{+2}$ |
| n | 3.680 | 1.510 | | 2.770 | 1.580 | 2.150 |
| $R^2$ | 0.9884 | 0.9902 | | 0.9927 | 0.9233 | 0.9895 |
| sen | $1.826*10^{-2}$ | $3.289*10^{-2}$ | | $1.545*10^{-2}$ | $9.546*10^{-2}$ | $2.395*10^{-2}$ |
| sey | $1.610*10^{-2}$ | $2.821*10^{-2}$ | | $1.504*10^{-2}$ | $2.928*10^{-2}$ | $2.573*10^{-2}$ |
| Langmuir | | | | | | |
| $q_{max}$ | $52.63*10^{+1}$ | $14.28*10^{+2}$ | | $20.00*10^{+2}$ | $25.00*10^{+2}$ | $14.28*10^{+2}$ |
| $K_L$ | 63.33 | 17.50 | | 25.00 | 2.000 | 87.50 |
| $R^2$ | 0.9998 | 0.9823 | | 0.9581 | 0.8216 | 0.9840 |
| sen | $3.100*10^{-7}$ | $4.431*10^{-6}$ | | $1.901*10^{-6}$ | $2.135*10^{-5}$ | $5.699*10^{-7}$ |
| sey | $1.126*10^{-5}$ | $1.713*10^{-4}$ | | $6.645*10^{-5}$ | $6.150*10^{-5}$ | $1.253*10^{-4}$ |
| Temkin | | | | | | |
| A | 331.70 | 1.000 | | 199.3 | 19.20 | 635.7 |
| b | 21.06 | 6.190 | | 5.130 | 4.080 | 7.770 |
| $R^2$ | 0.9637 | 0.9646 | | 0.9639 | 0.9380 | 0.9612 |
| sen | 4.691 | 37.78 | | $4.669*10^{-2}$ | $7.805*10^{-2}$ | $3.054*10^{-2}$ |
| sey | 9.522 | 74.62 | | 0.1046 | $5.512*10^{-2}$ | $7.556*10^{-2}$ |

Freundlich Isotherm.

Freundlich isotherms assume heterogeneous surface energies, in which the energy term in the Langmuir equation varies as a function of the surface coverage. The linear form of the Freundlich isotherm is given by the following equation:

$$\ln q_e = \ln K_F + \frac{1}{n}\ln C_e$$

where $C_e$ is the equilibrium concentration of the metal ion (mg/L), $q_e$ is the amount of metal ion adsorbed per unit mass of hydrogel (mg/g), $K_F$ (mg/g (l/mg)l/n) and n are Freundlich constants with n giving an indication of how favorable the absorption process is. The plot of $\ln q_e$ versus $\ln C_e$ gave a straight line with slope of l/n. Freundlich constants $K_F$ and n were also calculated and are listed in Table 8.

Temkin Isotherm.

Temkin and Pyzhev considered the effects of indirect adsorbate/adsorbent interactions on adsorption isotherms. The heat of adsorption of all the molecules in the layer would decrease linearly with coverage due to adsorbate/adsorbent interactions. The Temkin isotherm has been used in the form as follows:

$$q_e = \left(\frac{RT}{b}\right)\ln(AC_e).$$

A plot of $q_e$ versus $\ln C_e$ yielded a straight line. The constants A and b together with the $R^2$ values are shown in Table 2.

Synthesis and Characterization.

Poly(allylamine hydrochloride) was cross-linked with N,N-methylenebisacrylamide (MBA) by a Michael-type addition reaction. The reaction was performed in water using several monomer to cross-linker ratios. An acceptable hydrogel yield was obtained for various reaction conditions, as shown in Table 7. Although cross-linking was done by linking the primary amine groups, there were still a considerable number of reactive amino sites available for further modification of the PAAm hydrogel. 2,3 DHBA was covalently linked to the PAAm hydrogel via DCC/NHC conjugation chemistry.

Swelling Studies.

The swelling kinetics of PAAm and PAAm/DHBA were studied to determine the time to reach equilibrium. Hydrogel swelling increased with time; however, it eventually plateaued, thus, allowing calculation of the equilibrium swelling percentage. PAAm hydrogel reached equilibrium in 10 hours whereas PAAm/DBHA reached equilibrium in less than 1 hours, as shown in FIGS. 40A and 40B.

The cross-linker concentration was varied and the swelling behaviors of the final PAAm hydrogels were determined. Table 7 includes swelling indexes of PAAm hydrogels with different PAAm: cross-linker ratios. A 2.7 ratio was selected because the swelling index for this ratio is within an acceptable range for either chemical or biomedical applications. Next, the swelling behaviors of the hydrogels were further investigated as a function of pH by immersing the gels in buffered solutions at pH 1, 2, 4, 5, and 7.4 at room temperature (~25° C.). The swelling behavior of PAAm was determined after equilibrating at different pHs, as shown in FIG. 41A. The swelling of the PAAm hydrogel is higher at low pH values, with the maximum swelling observed at a pH of 2.2. This could be attributed to the complete protonation of the amine groups of PAAm at low pH. The $pK_a$ of primary amines in PAAm is ~9.67; therefore, the behavior observed resulted from the ionized amines of the polymer as expected. Osmotic pressure results from counterions to the protonated primary amines and is a probable cause of swelling. When immersed in electrolyte solutions, ion exchange takes place in these types of hydrogels during the swelling process and can exert a considerable effect on the water absorption.

The same experiment was carried out for PAAm conjugate hydrogels and the swelling behavior of the 2,3 DHBA modified gels were studied at different pH values, as shown in FIG. 41B. Because many of the amine groups were occupied via amide linkage, the ionizable groups within the hydrogel were diminished. Almost no significant changes in the swelling behavior were observed for PAAm/DHBA at different pHs.

Figure 42:
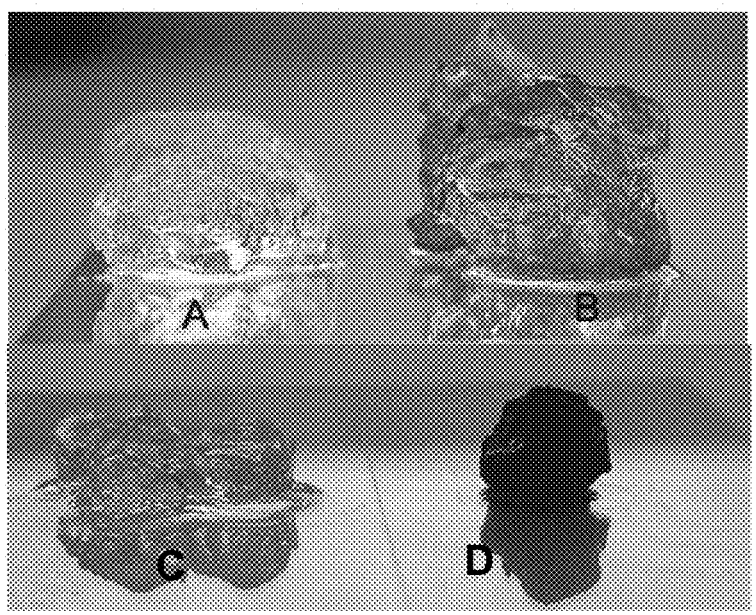

Images of equal weights of the different hydrogels also illustrated the vast difference in swelling. PAAm hydrogels showed a significant reduction in swelling after modification by 2,3 DHBA, as shown in FIGS. 42A and 42B. The occupation of ionizable amine groups after conjugation of DHBA greatly reduced water uptake and presumably reduced the uptake of counterions. Moreover, PAAm/DHBA hydrogel further collapsed after immersion in a 2 mg/mL solution of ferric chloride, as shown in FIG. 42C. Hydroxyl groups along with oxygen molecules bearing a negative charge (due to the partial double bond characteristic of the amide linkage) provided probable coordination sites for Fe. Moreover, as evident from potentiometric data, some protonated amine groups may also contribute to the coordination of Fe. The potentiometric data obtained for PAAm and PAAm/DHBA indicated that Ca. 23% of amine groups were occupied after conjugation reaction. Further collapse of PAAm/DHBA hydrogel in the ferric solution may be explained by multiple DHBA coordination of Fe.

Binding Kinetics.

Determination of the kinetics of metal absorption is critical in elucidating the reactivity of PAAm/DHBA and evaluating its potential for chemical and biomedical applications. The kinetics of metal binding was monitored using a known initial concentration of metal solution (2 mg/mL, $FeCl_3$) in the presence of a known mass of dry hydrogels. The equilibrium binding was found to be 1180 and 810 mg Fe/g Gel for PAAm/DHBA and PAAm, respectively, as shown in FIG. 43. About 80% of the total iron absorption was attained in less than 5 minutes for the PAAm/DHBA hydrogel. This rapid absorption behavior is important in biomedical application especially for treatment of acute metal poisoning. To derive the rate constant and binding capacity, the kinetic data were modeled with pseudo-first-order (Lagergren model) and pseudo-second-order (Ho model) kinetic models which are expressed in their linear forms as:

$$\log(q_e - q_t) = \log(q_e) - \frac{k_1}{2.303}t$$

$$\frac{t}{q_2} = \frac{1}{q_e^2 k_2} + \frac{t}{q_e}$$

where $k_1$ (L/min) and $k_2$ (g/mg·min) are pseudo-first-order and pseudo-second-order rate constants, respectively. Fitted kinetic models are shown in FIG. 44, and the model variables obtained by linear regression were compared, as shown below in Table 9.

TABLE 9

Kinetic parameters for ferric binding by PAAm/DHBA at pH = 2.

| Kinetic model | Rate constant | Ion | $R^2$ |
|---|---|---|---|
| Pseudo-first order | 0.24 | ferric | 0.9988 |
| Pseudo-second order | 0.23 | ferric | 1 |

The pseudo-second order reaction model showed the best fit for ferric ions because its $R^2$ was ~1.

Binding Isotherms.

The metal ion binding capacity was determined at different pH values and different isotherm models were used to fit the data. At low pH, the metal ion uptake was relatively high. This could be due to the presence of protonated primary amine groups along with iron coordination sites, which together may improve the binding capacity of the hydrogel for iron. Increasing the pH decreased the ionization of the remaining primary amine groups, and in turn lower values for the metal ion uptake were observed. The respective isotherm curves of ferric and ferrous solutions were obtained at different pH values, as shown in FIGS. 45 and 46.

Modeling of isotherm data is vital for deriving meaningful information of binding characteristics, such as maximum binding capacity and binding constant. Therefore, several theoretical isotherm equations, including those of Freundlich, Langmuir, and Temkin, were employed to evaluate which could best describe the experimental data. Generally, the Freundlich and Temkin models are applicable to heterogeneous systems, while the Langmuir model is based on a homogeneous monolayer adsorption. Among the three models, both Freundlich and Temkin models provided accurate ferric and ferrous isotherms at low implying the heterogeneous nature of adsorption, as shown in FIGS. 45 and 46. $R^2$ values obtained for these models were close to unity compared to the Langmuir model, as shown in Table 8. The data may allow speculation that more than one type of binding site with different affinities may be involved in iron binding by PAAm/DHBA. This hypothesis will require further studies to confirm or refute.

The removal of iron from different systems using Sepharose-desferrioxamine B gels has previously been reported. The effect of the immobilization of other iron chelators like 1-(fl-aminoethyl)-3-hydroxy-2-methyl-4-pyridinone (HP) and L-mimosine onto Sepharose have also been studied. However, the effectiveness of the immobilized DFO was low. Even though gels had a high affinity for Fe(III) and were used for removing iron from milk, wine, whey and lactoferrin, they were not very stable mainly due to hydrolysis of their isourea bonds. The iron binding parameters of hydroxamic acid-containing hydrogels derived from derived from cross-linked polymeric acid chloride precursor and polymeric hydroxyethyl ester precursor have also been studied. The maximum iron(III) binding capacities of these hydrogels were 0.81 and 0.45 mmol/g respectively. The maximum iron(III) binding capacity of PAAm/DHBA hydrogel varies between 9.3-25.5 mmol/g depending on the pH of the solution.

Selectivity Studies Effect of Essential Metals.

One of the important features of metal chelating hydrogels is their ability to specifically target the metal of interest and remove it from the media. Selectivity is especially important if the desired application of the hydrogel is in the treatment of metal poisoning. The hydrogel selectivity may affect the bioavailability of some other essential metal ions such as $Cu^{2+}$, $Zn^{2+}$, $Ca^{2+}$, $Mn^{2+}$, $Ni^{2+}$, or $K^+$. Selective absorption of essential metals could cause serious damage to vital organs. The influence of essential metals on the binding of ferric ions was investigated using a multi-solute system to evaluate the metal selectivity of PAAm/DHBA at different pHs. At an equal concentration of all metals (2 mg/mL), PAAm/DHBA absorbed almost 80% of the iron present in the media while typically the absorption for essential metals (e.g. Ca, Zn) was less than 50%, as shown in FIG. 47. The ratio was similar across a wide range of pHs. The selectivity of 3-hydroxypyridin-4-one hexadentate ligand-containing copolymers (DMAA) for iron in the presence of some essential metals has previously been studied. Even though the DMAA hydrogel showed high affinity for iron it still bound $Cu^{2+}$ efficiently (more than 53%). Comparatively, PAAm/DHBA showed a higher selectivity toward Fe in the presence of other metals, implying the greater stability of the Fe-PAAm/DHBA complex.

Example 5

Materials.

Poly(allylamine hydrochloride) (PAAm) with an average molecular weight of 56 kDa and analytical grade reagent N,N'-methylenebisacrylamide (MBA) were obtained from Sigma-Aldrich and used without further modification. 2,3 dihydroxybenzoic acid, thioglycolic acid (TGA), N,N,N-triethylamine (TEA), dimethylformamide (DMF), and all metal chlorides were purchased from Fisher Scientific and used as received. Dicyclohexylcarbodiimide (DCC) and N-hydroxysuccinimide (NHS) were purchased from Thermo Scientific and used without further modification. Deionized water (DI) was obtained from a Barnstead EasyPure water purifier.

Preparation of PAAm Hydrogel.

Briefly, a 20% w/v polymer solution containing a predetermined amount of MBA was prepared. The cross-linker was dissolved in deionized water (flushed with nitrogen for 5 minutes) and then added to the polyallylamine polymer. TEA, the cross-linking catalyst (300 µL), was then added to the solutions and mixed thoroughly. Next, the precursors were transferred by micropipet into small vials. The vials were held at ambient temperature for 1 hour and then cooled to ca. 3° C. and held there for an additional 24 hours. After this time, hydrogels were removed from the vial and washed with 0.05 M sodium chloride for several days.

Functionalization of Hydrogel.

A solution of TGA and NHS in 5 mL of DMF was mixed with a solution of DCC in 5 mL of DMF. The mixture was stirred at low temperature for 6 hour to give a white precipitate. The precipitate was filtered, and the filtrate was added directly to a dry gel with known weight. The reaction mixture was held at room temperature for 3 days. PAAm conjugate hydrogel was then washed with water for several days. The same procedure was done for the conjugation of 1:1 molar ratio of TGA/DHBA.

Quantification of Amine Functional Groups

Primary amine groups were quantified by potentiometric titration. After grinding to a powder, 40 mg of functionalized hydrogels were suspended in 35 mL of 0.2 M aqueous KCl solution. Next, 140 µL of 8 M KOH aqueous solution was added to polymer suspensions to raise the pH to ~12. Standard 0.1 M HCl was used to titrate the suspension. HCl was added until the pH was about 2.5 in all polymer suspensions. Free amine groups were quantified from potentiometric data following reported procedures.

Binding Kinetics Study

Metal chloride solutions (2 mg/mL) were adjusted to pH 2.5 with ionic strength in the range of 0.02 M to 0.04 M and kept at room temperature for kinetic studies. Samples were taken from the media at different time intervals to determine the rate of metal binding by functionalized hydrogel.

Binding Experiments

Known concentrations of metal chloride solutions (0.25, 0.5, 1, 2, 2.5) mg/mL were prepared. Binding experiments were carried out by taking 20 mL of metal solution in 125 mL volumetric flasks. Solutions were adjusted to pH=2.5 while maintaining metal concentration. Ionic strength of all solutions was between 0.02 M to 0.04 M. Next, a known mass of functionalized hydrogel was added to the mixture and was held at room temperature for 2 hours or until equilibrium was reached. The solutions were then filtered and the filtrates were analyzed for metal concentration.

Adsorption Isotherms.

Different isotherm models were employed to determine how the metal molecules distributed between the liquid phase and the hydrogel phase when the adsorption process reached equilibrium. Langmuir, Freundlich, and Temkin isotherm models were applied to the data. Adsorption parameters for each metal ion were calculated at a pH value of 2.5. The constants for each isotherm model were calculated and the accuracy of the isotherm models were evaluated using linear correlation coefficient ($R2$) values, as shown in Table 12.

Selectivity Study

The selectivity for Pb, Cd, and As by functionalized PAAm in the presence of competing metals was studied. A metal solution (10 mL, 2 mg/mL) containing all metal components was prepared. The solution mixture was then adjusted to pH 2.5 and held at room temperature for 2 hours after adding a known mass of functionalized dry gel. Ionic strength of all solutions was between 0.02 M to 0.04 M.

Metal Analysis

Mono- and multi-elemental analysis of samples was quantified by Inductively Coupled Plasma Optical Emission Spectrometry (ICP-OES) (Optima 2000 DV, PerkinElmer, USA) fitted with an AS 93plus autosampler (PerkinElmer, USA). A Cross-Flow nebulizer and a Scott spray chamber were used. The RF Power was 1300 W and nebulizer and auxiliary flows were 0.8 and 0.2 L/min, respectively. Sample flow was set at 1.5 mL/min. ICP-OES data was processed using Winlab 32 (Ver. 3.0, PerkinElmer, USA). The analytical curves used for sample analysis had coefficients of correlation >0.999.

Synthesis and Characterization

Poly(allylamine hydrochloride) was cross-linked following a previously reported method. Here, an optimized reaction yield was chosen from the previously reported data. 2,3 DHBA and TGA were covalently linked to the available amino sites of PAAm hydrogel via DCC/NHC conjugation chemistry. Moreover, potentiometric titration data were used to calculate the degree of conjugation using the following equation:

$$\bar{n} = \frac{C_{HCL} = (H^+) + (OH^-)}{C_H}$$

Here, $C_H$ is the concentration of hydrogel. The conjugation efficiency was 47% and 67% for PAAm/TGA and PAAm/TGA/DHBA hydrogels, respectively.

Binding Kinetics.

Determination of the kinetics of metal absorption is critical for elucidating the performance of hydrogels and for evaluating its potential for chemical and biomedical applications. The kinetics of metal binding was monitored by adding a known mass of dry hydrogels to a known initial concentration of metal solution (2 mg/mL, metal chloride). The concentration of metal in solution was monitored over time. About 40%-50% of the total metal absorption was attained in less than 5 min for all functionalized hydrogels, as shown in FIG. 49. The absorption was fastest for As in the presence of the different functionalized hydrogels and slowest for Cd. This might be due to the smaller atomic radius of As compared to Pb and Cd. Previously; composite hydrogels were synthesized with magnetic properties and studied for the removal of toxic metal ions from aqueous environments. In all the case studies, less than 40% of the total metal was absorbed after 2 hours. In most studies the minimum required time to reach ~50% of the total removal is about 15-30 minutes. The rapid absorption behavior of hydrogels reported here may offer an important advantage, especially in biomedical applications such as the treatment of acute metal poisoning.

The equilibrium binding values were systematically higher for PAAm/TGA hydrogels compared to PAAm/TGA/DHBA, as shown in Table 10.

TABLE 10

Maximum binding capacity of hydrogels at pH = 2.5 when ionic strength varied between 0.02M and 0.04M.

| | Chelating hydrogel | |
|---|---|---|
| Metal ion | PAAm/TGA | PAAm/TGA/DHBA |
| As | 568 | 520 |
| Pb | 345 | 291 |
| Cd | 452 | 294 |

This might be because of a high density of thiol groups available for coordinating with toxic metals. A systematic study on Cd and Pb absorption and kinetic binding for a metal-binding material produced by introducing sulphydryl functional groups into natural hemp fibers was previously conducted. The absorption capacity of modified hemp was reported to be 14.0 and 23.0 mg/g of fibers for cadmium and lead ions, respectively at room temperature. In comparison, hydrogels reported here achieved 452.6 and 294.9 mg/g of hydrogel for Cd and 354.7 and 291.8 mg/g of hydrogel for Pb with PAAm/TGA and PAAm/TGA/DHBA gels, respectively.

To derive the rate constant and binding capacity, the kinetic data were modeled with pseudo-first-order (Lagergren model) and pseudo-second-order (Ho model) kinetic models which are expressed in their linear forms as shown in equations 5 and 6, where $k_1$ (L/min) and $k_2$ (g/mg·min) are pseudo-first-order and pseudo-second-order rate constants, respectively. The model variables obtained by linear regression were compared, as shown in Table 11.

TABLE 11

Kinetic parameters for metal binding by functionalized hydrogels at pH = 2.5. Ionic strength values ranged from 0.02M to 0.04M.

| | | Chelating hydrogel | | | |
|---|---|---|---|---|---|
| | | Ho model | | Lagregern model | |
| Metal ion | | PAAm/TGA | PAAm/TGA/DHBA | PAAm/TGA | PAAm/TGA/DHBA |
| $R^2$ | As | 0.999 | 1 | 0.864 | 0.0466 |
| K | | 14.7 | 13.4 | 0.0100 | N/A |
| $R^2$ | Pb | 0.997 | 0.999 | 0.986 | 0.939 |
| K | | 16.0 | 5.46 | 0.0100 | 0.0203 |
| $R^2$ | Cd | 0.996 | 0.999 | 0.00360 | 0.521 |
| K | | 0.00380 | 1.079 | N/A | N/A |

The pseudo-second order reaction model showed the best fit since it had a $R^2$ value close to unity in each of these cases.

Binding Isotherms.

The metal ion binding capacity was determined and different isotherm models were used to fit the data. A low pH was selected for these studies because of the potential application of these hydrogels in acute metal poisoning (stomach pH ~2.5). The metal ion uptake was relatively high. This could be due to the presence of protonated primary amine groups along with thiol functional groups which together provided excellent coordination sites for metal binding.

Several theoretical isotherm equations, including those of Freundlich, Langmuir, and Temkin, were employed to evaluate which could best describe the experimental data. None of the three adsorption models provided an accurate fit for data reported in this study as low correlation coefficient values were observed, as shown in Table 12.

TABLE 12

Isotherm parameters for metal binding by functionalized hydrogels at pH = 2.5. Ionic strength values ranged from 0.02M to 0.04M.

| | Hydrogel | | | | | |
|---|---|---|---|---|---|---|
| Isotherm model | TGA Pb | DHBA/TGA Pb | TGA Cd | DHBA-TGA Cd | TGA As | DHBA/TGA As |
| Freundlich | | | | | | |
| $K_F$ | NA | 1.027 | NA | NA | $1.060*10^7$ | $16.7*10^2$ |
| n | NA | −2.16 | NA | NA | 2.40 | −0.516 |
| $R^2$ | 0.141 | 0.778 | 0.455 | 0.228 | 0.875 | 0.926 |
| sen | NA | 0.122 | NA | NA | 0.0784 | 0.273 |
| sey | NA | 0.142 | NA | NA | 0.216 | 0.476 |
| Langmuir | | | | | | |
| $q_{max}$ | NA | $0.890*10^2$ | NA | 81.7 | 664.5 | −4.51 |
| $K_L$ | NA | −5.10 | NA | −2.79 | 32.2 | 62.9 |
| $R^2$ | 0.0215 | 0.644 | 0.321 | 0.793 | 0.952 | 0.863 |
| sen | NA | $8.16*10^{-4}$ | NA | 0.00111 | $5.20*10^{-6}$ | $6.98*10^{-4}$ |
| sey | NA | 0.00301 | NA | 0.00215 | $4.057*10^{-4}$ | 0.00204 |
| Temkin | | | | | | |
| A | NA | 0.0814 | NA | NA | $25.3*10^1$ | NA |
| b | NA | −33.5 | NA | NA | 16.1 | NA |
| $R^2$ | 0.101 | 0.611 | 0.176 | 0.356 | 0.695 | 0.365 |
| sen | NA | 29.4 | NA | NA | 50.6 | NA |
| sey | NA | 78.7 | NA | NA | $13.9*10^1$ | NA |

In most cases, a reciprocal plot of the data gave a straight line fit for Langmuir isotherms but negative intercept values suggested that simple Langmuir adsorption did not occur. The Freundlich model assumes that there are many types of sites acting simultaneously, each with a different free energy of absorption, and that there is a large number of available sites. The negative cooperativity factor (n) below unity in this study is an indicator of heterogeneous absorption due to the negative lateral interaction between absorbed metal and/or non-uniform binding affinities of hydrogel sites. The Temkin isotherm assumes that a decrease in the heat of adsorption is linear and that the absorption is characterized by a uniform distribution of binding energies. This model did not fit data either, suggesting that multiple, complex binding mechanism may be involved in metal absorption.

Selectivity Study

An important feature of metal chelating hydrogels is the ability to specifically target the metal of interest and remove it from the media. The metal selectivity of PAAm/TGA and PAAm/TGA/DHBA hydrogels was investigated using a multi-solute system. At an equal concentration of all toxic metals (i.e. Pb, Cd, As at 2 mg/mL), PAAm/TGA absorbed almost 100% of the lead present in the media while in the same experiment and in the presence of other competing metals such as Fe and Zn this value decreased to ~70%, as shown in FIG. 50. The tendency of PAAm/TGA hydrogel for absorption of metals followed the order of Pb>As>Cd>Zn>Fe. This trend was similar for PAAm/TGA/DHBA. Previously a high Pb removal capacity using magnetic hydrogels (130 mg/g) was reported. The Pb removal capacity with PAAm/TGA and PAAm/TGA/DHBA was 345.6 and 291.7 mg/g, respectively. All data suggested that these hydrogels may have excellent potential in waste water treatment and probable application in acute metal poisoning.

Example 6

Materials.

Poly-L-lysine hydrobromide (PLL) with an average molecular weight of 1530 kDa was obtained from Sigma-Aldrich and used without further modification. 2,3 dihydroxybenzoic acid (2,3 DHBA), N,N,N-triethylamine (TEA), dimethylformamide (DMF), potassium phosphate and all metal chlorides were purchased from Fisher Scientific and used as received. Dicyclohexylcarbodiimide (DCC) and Nhydroxysuccinimide (NHS) were purchased from Thermo Scientific and used without further modification. Deionized water (DI) was obtained from a Barnstead EasyPure water purifier.

2,3 Dihydroxybenzoic Acid Modification of Polymer.

A solution of 2,3 DHBA (64 mg, 0.42 mmol) and NHS (47.48 mg, 0.4 mmol) in 5 mL of DMF was mixed with a solution of DCC (42.5 mg, 0.2 mmol) in 5 mL of DMF. The mixture was stirred at low temperature for 6 hr to give a white precipitate. The precipitate was filtered, and the filtrate was added directly to a solution of PLL (15 mg/mL, 2 mL). The reaction mixture was held at room temperature for 6 hours. Next, DMF was evaporated using rotovap and sample was kept at vacuum oven over night to ensure the complete evaporation of DMF. PLL conjugate polymer was dissolved in water and was washed against water for several days.

Binding Kinetics Study.

Ferric chloride solution (2 mg/mL) was adjusted to pH 6.5 and kept at room temperature for kinetic studies. Samples were taken from the media at different time intervals to determine the rate of iron binding by PLL/DHBA.

Selectivity Study.

The selectivity for Fe by PLL/DHBA in the presence of several heavy metals such as copper, zinc, manganese, calcium, and potassium was studied. Metal solutions (10 mL) containing a 1:1 (wt) mixture of iron and heavy metals were prepared (2 mg/mL). The solution mixtures were then adjusted to pH 2.5 and held at room temperature. PLL/DHBA (6 mg/mL, 10 mL) was transferred to the dialysis bag and immersed into the above solution. Samples were taken from the solution after 2 hours to study the metal concentration.

Cytotoxity of Polymeric Iron Chelator.

High throughput cell viability assays were completed using standard procedures. Cytotoxicity of polymers was determined by the CellTiter 96® Aqueous Cell Proliferation Assay (Promega). A549 and HUVEC cells were cultured and incubated with polymers for ~24 hours. Next, the media was removed and replaced with a mixture of 100 µL fresh culture media and 20 µL MTS reagent solution and cells were incubated for 3 hours at 37° C. in a 5% $CO_2$ incubator. The absorbance of each well was then measured at 490 nm using a microtiter plate reader (SpectraMax, M25, Molecular Devices Corp.) to determine relative cell viability.

In Vitro Hemolysis Assay of the Polymer.

Hemolysis assay was performed using fresh mice blood. The erythrocytes were collected by centrifugation at 1500 rpm for 15 min, and then washed three times with 35 mL of Phosphate buffered saline (PBS) buffer at pH 7.4. The stock solution was prepared by mixing 2 mL of centrifuged erythrocytes into 45 mL of PBS. The PLL/DHBA solutions were prepared in PBS buffer with four different concentrations (1 mg/mL, 100 µg/mL, 10 µg/mL, and 1 µg/mL). One hundred microliter of sample solution was added to 1 mL of the stock solution in a 96-well plate. The solutions were incubated for 1 hour at 37° C. in an Incubator. The percentage of hemolysis was measured by UV-vis analysis of the supernatant at 570 nm absorbance after centrifugation at 3000 rpm for 1 hr. One milliliter of saline was used as the negative control.

Result.

The kinetics of metal binding was monitored in a 2 mg/mL FeCb solution. The equilibrium binding was found to be 1303.7 mg/g for iron chelating polymer. More importantly, about 80% of total absorption was attained in <5 min, as shown in FIG. 51 and Table 13, which reports iron content as determined from direct quantification from inside the dialysis bag or as calculated from unabsorbed iron (out side the dialysis bag).

TABLE 13

| Measured | % absorbed |
| --- | --- |
| Bag | 85.85 |
| Out side the bag | 76.98 |

This near instantaneous iron absorption behavior may be highly desired for treatment of acute iron overload.

A multi-solute system was used to evaluate the metal selectivity of siderophore mimetic polymer. At an equal concentration of all metals (2 mg/mL), siderophore mimetic polymer (i.e. modified with DHBA) absorbed almost 75% of the iron in the media, the highest of any metal present except Ni which normally has a lower initial concentration comparing to the initial concentration used in this study, as shown in FIG. 52. In a realistic study selectivity may be found while using upper tolerable intake level of each metal as an initial concentration in a media. Siderophore-mimetic polymers were highly selective for iron and nickel over essential elements zinc and calcium, as desired.

MTS cytotoxicity assay was used to study the toxic effect of PLL/DHBA on HUVEC and A549 cells. DFO, an FDA approved drug which is currently on the market and is used for the treatment of iron overload disease, was used as a control. PLL/DHBA showed almost no toxic effect on HUVEC cells while DFO was considerably toxic even at concentration as low as 10 µg/mL, as shown in FIG. 53. Both PLL/DHBA and DFO had no toxic effect of A549 cells, as shown in FIG. 54.

When the siderophore-mimetic polymer is injected into the blood for detoxification, detrimental interaction of this polymer with the blood constituents must be avoided. Although the concentration of the polymer solutions was relatively high, PLL/DHBA solution did not show any observational hemolytic activities in the red blood cell in the experimental range, as shown in FIG. 55.

Example 7

Materials.

All the chemicals were obtained from Sigma-Aldrich and used as received.

Preparation of the Iron Chelation Hydrogel.

NHS activated DHBA was first synthesized before preparing the hydrogel. A solution of DHBA (770 mg, 5 mmol) and NHS (690 mg, 6 mmol) in 5 mL of DMF was mixed with a solution of EDC (1200 mg, 6 mmol) in 5 mL of DMF. The mixture was stirred at room temperature for 6 h and used for the next step without any purification. The PAAm crosslinking and DHBA conjugation were conducted in a single step. Briefly, a 15% w/w polyallylamine hydrochloride (56 K) solution containing a predetermined amount of BMA (5%, molar ratio of cross-linker to total amines) was prepared. Then the NHS activated DHBA solution with a desired DHBA/amine molar ratio (5-40%) was added to the solution. After sonicated for 2 min, triethylamine (TEA) was added to the solutions and mixed thoroughly. The precursor was transferred into a microtube and incubated at room temperature for 48 h. The formed gels were cut into several tablets and washed with 0.1M sodium hydroxide for several days, and then lyophilized.

Table 14 shows various parameters for one-step preparation of PAAm-DHBA gels with various DHBA content.

TABLE 14

| Sample | Cross-linking Density[a] | Feed DHBA/amine[b] | Found DHBA/amine[c] | Swelling index | |
| --- | --- | --- | --- | --- | --- |
| | | | | pH 2.0 | pH 7.4 |
| G5 | 0.05 | 0.05 | 0.0311 | 18.8 | 11.8 |
| G10 | 0.05 | 0.10 | 0.0700 | 12.9 | 8.2 |
| G15 | 0.05 | 0.15 | 0.1117 | 9.3 | 6.9 |
| G20 | 0.05 | 0.20 | 0.1488 | 8.8 | 5.6 |
| G25 | 0.05 | 0.25 | 0.1743 | 8.4 | 5.4 |
| G30 | 0.05 | 0.30 | 0.2216 | 7.4 | 5.3 |
| G35 | 0.05 | 0.35 | — | — | — |
| G40 | 0.05 | 0.40 | — | — | — |

[a]Feed molar ratio of cross-linker to total amines
[b]Feed molar ratio of DHBA to total amines
[c]Found molar ratio of DHBA to total amines by NMR analysis Swelling Studies.

The swelling behavior of hydrogels was studied using buffered solutions at various pH values with fixed ionic strength (0.5M) according to an historic protocol. Dried samples with predetermined weights were placed in a solution of defined pH at room temperature. Samples were taken from the solution at different time points. The swelling indices (SI) were calculated using the following equation:

$$\pi = \frac{W_a - W_d}{W_d}$$

Where Ws is the weight of the swollen hydrogel at a certain time point and Wd is the weight of the dried hydrogel. As shown in FIG. 56, the gels swell rapidly in both pH 2 and pH 7.4 buffers and increasing DHBA reduces swelling.

Determination of the Iron Stability Constant.

The stability constant of gel chelators was measured using an historic ligand competition assay. The competitive chelation of iron by polymeric chelator in equilibrium with a water-soluble chelator (ethylenediaminetetraacetic acid: EDTA) was used to determine the stability constant of iron-ligand complexes of hydrogel. Briefly, to a 1.5 ml of 10 mM EDTA solution was added 2 mL of 5 mM of $FeCl_3$ solution and 21.5 mL PBS and a known mass of gel. The mixture rotated at 25 C for 5 days and the concentration of the soluble iron complex was determined by inductively coupled plasma optical mission spectrometry (ICP-OES). The stability constant of the gel was determined following the procedure reported in literature.

Kinetic Study of Iron Adsorption.

A known mass of gel was incubated in a 5 mM $FeCl_3$ solution. 1 ml of the solution was taken out at each time point, and determined by ICP-OES for the remaining iron concentration.

As shown in FIGS. 60 and 61, Ground PAAm-DHBA gel adsorbs $Fe^{3+}$ faster than the gel tablet. The ground powders only take less than 10 min to reach 50% of maximum iron adsorption; while the tablet takes about 15 h.

Determination of the Iron Chelation Capacity.

A known mass of gel was incubated in a 5 mM $FeCl_3$ solution at 25 C for a week. Then the remaining iron concentration was determined by ICP-OES.

As shown in FIG. 62, all samples show higher iron binding constants than Deferoxamien. FIGS. 63 and 64 show that all the PPAAm-DHBA gels tested showed excellent selectivity for Fe over other metals.

Table 15 shows the results for determining the iron biding capacity of various samples. This may be used to calculate a dose for removal of iron.

Table 15

| Sample | Found DHBA/amine[a] | Theoretical Fe Binding Capacity[b] (mg Fe/g Gel) | Experimental Fe Binding Capacity[c] (mg Fe/g Gel) | Ratio[d] |
|---|---|---|---|---|
| G5  | 0.0311 | 8.786  | 9.858 ± 2.962  | 112.20 ± 33.71% |
| G10 | 0.0700 | 18.301 | 16.152 ± 3.052 | 88.26 ± 16.68% |
| G15 | 0.1117 | 27.074 | 20.283 ± 1.236 | 74.92 ± 4.56% |
| G20 | 0.1488 | 33.833 | 20.782 ± 0.328 | 61.42 ± 0.97% |
| G25 | 0.1743 | 38.030 | 19.122 ± 1.449 | 50.28 ± 3.81% |
| G30 | 0.2216 | 44.967 | 16.923 ± 3.077 | 37.63 ± 6.84% |

[a]Found molar ratio of DHBA to total amines
[b]Calculated based on the found molar ratio of DHBA to total amines
[c]Fe concentration detected by ICP-OES
[d]Ratio of experimental Fe binding capacity to theoretical Fe binding capacity The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope. All references recited herein are incorporated herein by specific reference.

What is claimed is:

1. A composition comprising:
   a polymeric chelator comprising a plurality of polyamine polymer backbone chains and one or more chelators, wherein the polyamine polymer backbone chains are polyallylamine or polylysine;
   wherein the one or more chelators are covalently coupled to one or more primary amines, respectively, of at least one of the plurality of polyamine polymer backbone chains through one or more amide bonds, respectively, wherein each of the one or more chelators has a benzene ring with more than one hydroxyl group at any position that is free; and
   wherein the plurality of polyamine polymer backbone chains are cross-linked to one another independent of any cross-linking that may result from interactions with the one or more chelators.

2. The composition of claim 1, wherein the polymeric chelator is injectable.

3. The composition of claim 1, wherein the polymeric chelator is a hydrogel.

4. The composition of claim 1, wherein the polymeric chelator is ingestible.

5. The composition of claim 1, wherein the one or more chelators are capable of chelating a metal.

6. The composition of claim 1, wherein the one or more chelators are capable of chelating a heavy metal.

7. The composition of claim 1, wherein the one or more chelators are capable of chelating aluminum, arsenic, cadmium, chromium, copper, iron, lead, manganese, mercury, or combination thereof.

8. The composition of claim 1, wherein the one or more chelators are a derivative of a metal chelator.

9. The composition of claim 1 wherein each of the one or more chelators is derived from 2,3 dihydroxybenzoic acid.

10. The composition of claim 1 wherein the molar ratio of A to B is from about 0.07 to about 0.17, wherein A is chelators covalently coupled to primary amines, and wherein B is total amines of the polymeric chelator.

11. The composition of claim 1 wherein the molar ratio of A to B is from about 0.03 to about 0.22, wherein A is chelators covalently coupled to primary amines, and wherein B is total amines of the polymeric chelator.

* * * * *